(12) United States Patent
Ramsay et al.

(10) Patent No.: US 11,935,215 B2
(45) Date of Patent: Mar. 19, 2024

(54) SYSTEM AND METHOD FOR THE VISUALIZATION AND CHARACTERIZATION OF OBJECTS IN IMAGES

(71) Applicant: Imago Systems, Inc., Summit, NJ (US)

(72) Inventors: Thomas E. Ramsay, Leesburg, VA (US); Eugene B. Ramsay, Tucson, AZ (US)

(73) Assignee: Imago Systems, Inc., Summit, NJ (US)

( * ) Notice: Subject to any disclaimer, the term of this patent is extended or adjusted under 35 U.S.C. 154(b) by 29 days.

(21) Appl. No.: 16/784,821

(22) PCT Filed: Aug. 7, 2018

(86) PCT No.: PCT/US2018/045567
§ 371 (c)(1),
(2) Date: Feb. 7, 2020

(87) PCT Pub. No.: WO2019/032558
PCT Pub. Date: Feb. 14, 2019

(65) Prior Publication Data
US 2020/0219237 A1 Jul. 9, 2020

Related U.S. Application Data

(60) Provisional application No. 62/541,989, filed on Aug. 7, 2017.

(51) Int. Cl.
*G06T 5/00* (2006.01)
*G06T 5/50* (2006.01)
(Continued)

(52) U.S. Cl.
CPC ............. *G06T 5/008* (2013.01); *G06T 5/50* (2013.01); *G06T 7/0012* (2013.01); *G16H 30/40* (2018.01);
(Continued)

(58) Field of Classification Search
None
See application file for complete search history.

(56) References Cited

U.S. PATENT DOCUMENTS

2006/0078926 A1 4/2006 Marcelpoil et al.
2007/0230788 A1* 10/2007 Lei .................... G06T 5/40
382/186
(Continued)

FOREIGN PATENT DOCUMENTS

WO 2008157843 A1 12/2008

OTHER PUBLICATIONS

Baecker "Image processing and analysis with ImageJ and MRI Cell Image Analyzer." In: Montpellier RIO Imaging, Oct. 20, 2008., [online] [retrieved on Oct. 4, 2018 45), 52 (Oct. 4, 2018)] Retrieved from the Internet <URL:https://www.unige.ch/medecine/bioimaging/files/5714/1208/5898/Basics.pdf>, entire document, especially Abstract; p. 9-16, 27, 30-40, 50-55, 66.
(Continued)

*Primary Examiner* — Jiangeng Sun
(74) *Attorney, Agent, or Firm* — Morgan, Lewis & Bockius LLP

(57) ABSTRACT

A method of visualization, characterization, and detection of objects within an image by applying a local micro-contrast convergence algorithm to a first image to produce a second image that is different from the first image, wherein all like objects converge into similar patterns or colors in the second image.

21 Claims, 56 Drawing Sheets

Mammogram with pathology-validated cancer

Local micro-contrast processed images showing visualizations of the malignant lesion, defining its irregular boundaries

(51) Int. Cl.
*G06T 7/00* (2017.01)
*G16H 30/40* (2018.01)

(52) U.S. Cl.
CPC .............. *G06T 2207/10024* (2013.01); *G06T 2207/10048* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20221* (2013.01); *G06T 2207/30068* (2013.01); *G06T 2207/30096* (2013.01)

(56) References Cited

U.S. PATENT DOCUMENTS

| | | | | |
|---|---|---|---|---|
| 2008/0143739 | A1* | 6/2008 | Harris | G09G 5/377 345/604 |
| 2008/0304741 | A1* | 12/2008 | Brunner | G06K 9/3208 382/168 |
| 2009/0092298 | A1 | 4/2009 | Xu et al. | |
| 2009/0141320 | A1* | 6/2009 | Minamino | H04N 1/3875 358/512 |
| 2010/0141802 | A1* | 6/2010 | Knight | H04N 5/2254 348/240.3 |
| 2010/0201868 | A1* | 8/2010 | Che | H04N 5/142 348/448 |
| 2010/0208985 | A1* | 8/2010 | Lee | H04N 1/40012 382/163 |
| 2010/0246896 | A1* | 9/2010 | Saito | G06K 9/00798 382/106 |
| 2010/0266179 | A1 | 10/2010 | Ramsay et al. | |
| 2011/0026789 | A1 | 2/2011 | Hsu et al. | |
| 2011/0057943 | A1* | 3/2011 | Ivashin | H04N 9/3147 345/582 |
| 2014/0086382 | A1 | 3/2014 | Flohr et al. | |
| 2015/0023580 | A1 | 1/2015 | Wehnes et al. | |

OTHER PUBLICATIONS

International Search Report dated Oct. 5, 2018 for International Patent Application No. PCT/US2018/045567, 3 pages.
Written Opinion dated Oct. 5, 2018 for International Patent Application No. PCT/US2018/045567, 10 pages.
Shiaofen Fang et al.: Image-based transfer function design for data exploration in volume visualization11 , Visualization '98. Proceedings Research Triangle Park, NC, USA Oct. 18-23, 1998, Piscataway, NJ, USA, IEEE, US, Jan. 1, 1998 (Jan. 1, 1998), pp. 319-326.
Extended European Search Report dated Mar. 22, 2021 for European Patent Application No. 18844081.2, 12 pages.

* cited by examiner

Mammogram with pathology-validated cancer

Local micro-contrast processed images showing visualizations of the malignant lesion, defining its irregular boundaries

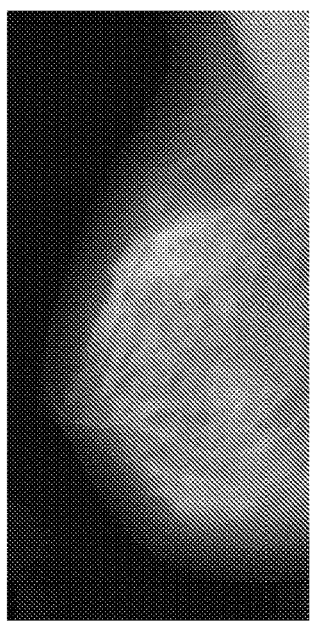
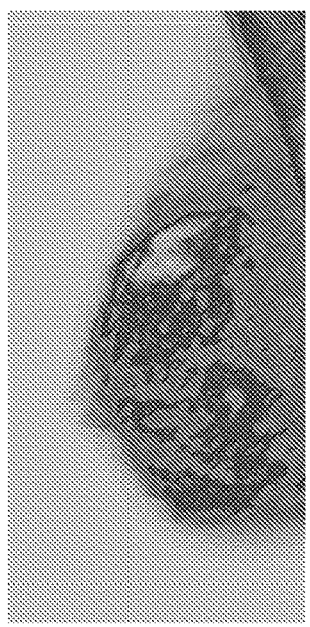
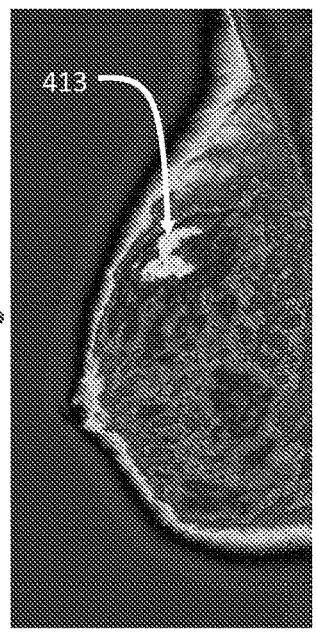
Figure 4a
Original Mammogram
Figure 4b
Resultant image after invert and CI PLUT 1
Figure 4c
Resultant image after CI PLUT 2
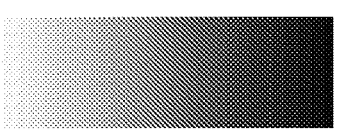
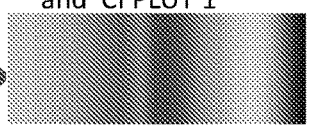
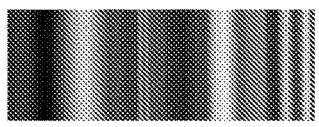
Figure 4d
Grayscale gradient
Figure 4e
Gradient after invert and CI PLUT 1
Figure 4f
Gradient after CI PLUT 2
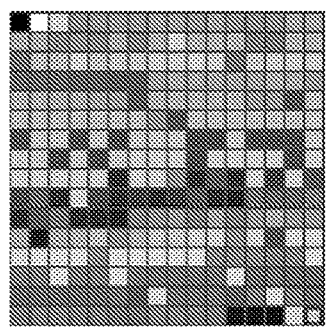
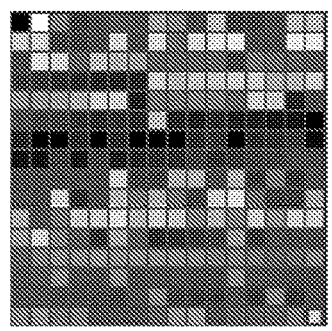
Figure 4g
CI PLUT 1 lookup table
Figure 4h
CI PLUT 2 lookup table
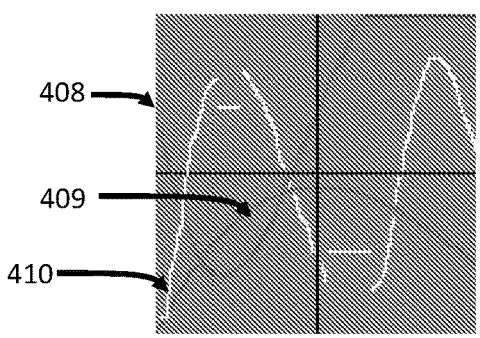
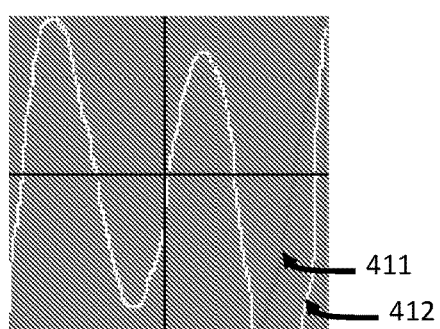
Figure 4i
CI PLUT 1 lookup table plot
Figure 4j
CI PLUT 2 lookup table plot Original Mammogram Resultant image after LD PLUT 1

Resultant image
after LD HLS adjustment

Grayscale gradient

Gradient after LD PLUT 1

Gradient after LD HLS adjustment

LD PLUT 1 lookup table

LD PLUT 1 lookup table plot

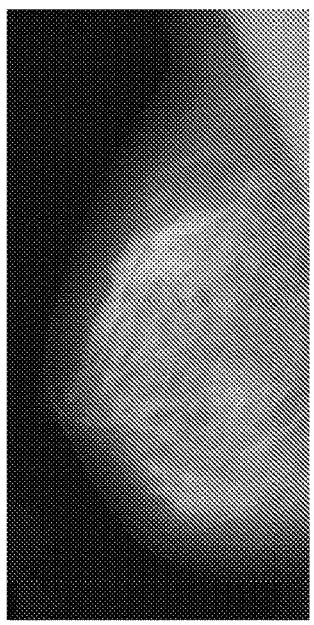
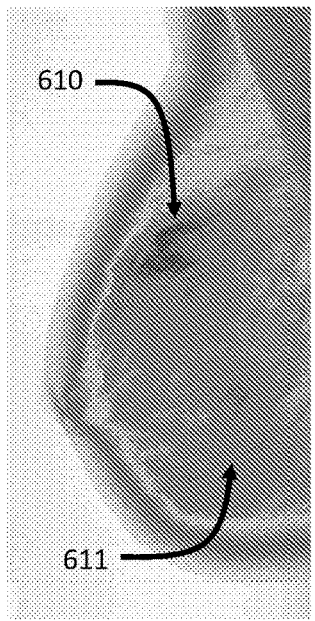
Figure 6a
Original Mammogram
Figure 6b Resultant
image after HD PLUT 1
Figure 6c Resultant image
after conversion to grayscale
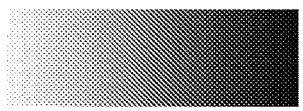
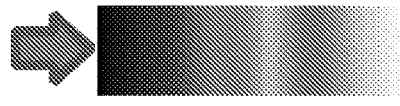
Figure 6d
Grayscale gradient
Figure 6e
Gradient after HD PLUT 1
Figure 6f
Gradient after conversion
to grayscale
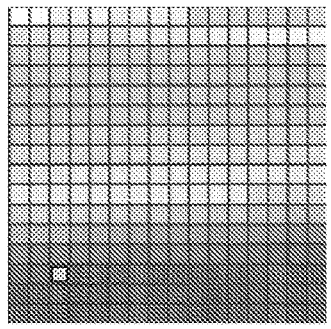
Figure 6g
HD PLUT 1 lookup table
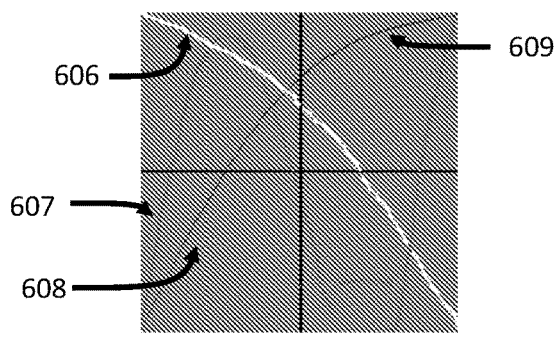
Figure 6h
HD PLUT 1 lookup table plot

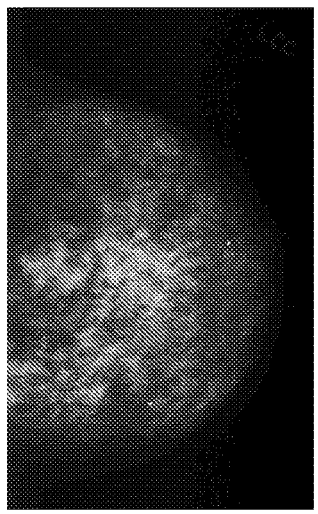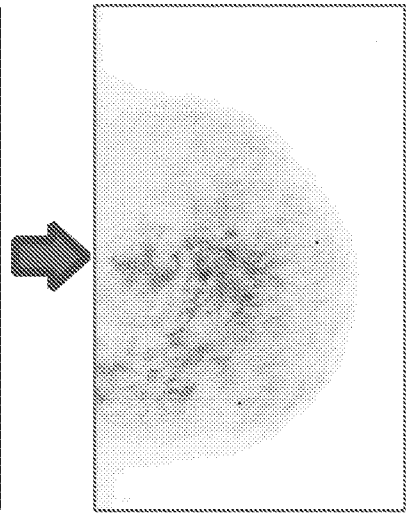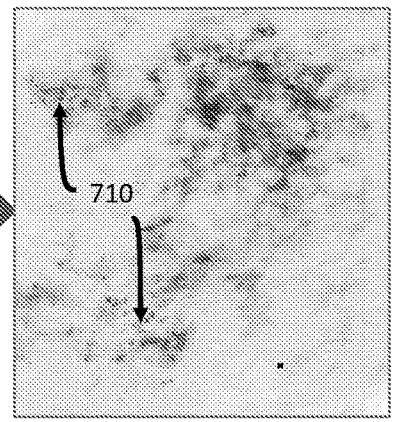
Figure 7a
Original Mammogram
Figure 7b
Resultant
image after MC PLUT 1
Figure 7c
Resultant image
close up after conversion
to grayscale
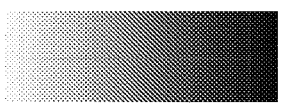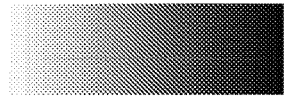
Figure 7d
Grayscale gradient
Figure 7e
Gradient after MC PLUT 1
Figure 7f Gradient
after conversion to grayscale
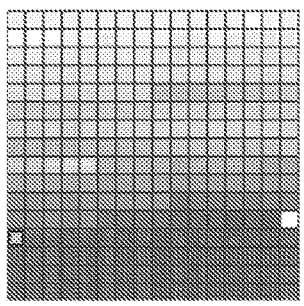
Figure 7h
MC PLUT 1 lookup table
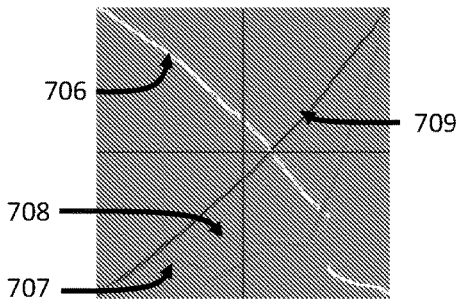
Figure 7i
MC PLUT 1 lookup table plot

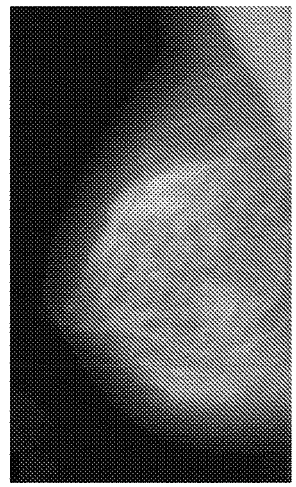
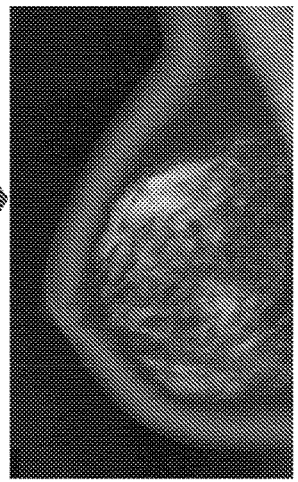
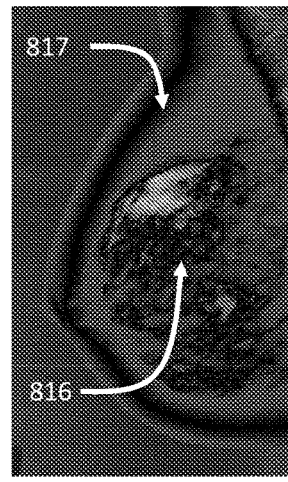
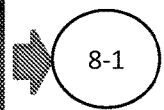
Figure 8a
Original Mammogram
Figure 8b
Resultant
image after RF PLUT 1
Figure 8c
Resultant
image after RF PLUT 2
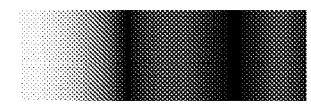
Figure 8d
Grayscale gradient
Figure 8e
Gradient after RF PLUT 1
Figure 8f
Gradient after RF PLUT 2
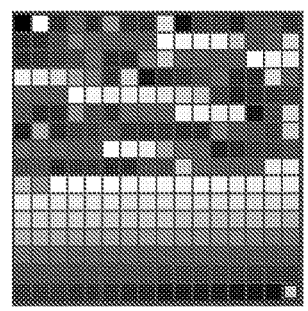
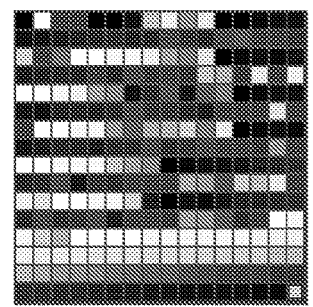
Figure 8g
RF PLUT 1 lookup table
Figure 8h
RF PLUT 2 lookup table
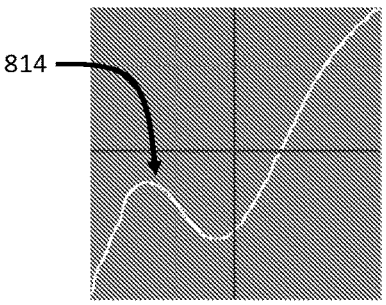
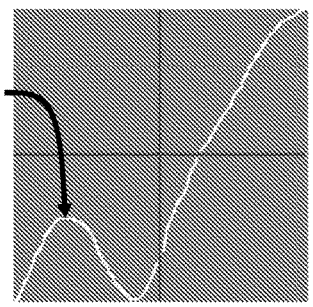
Figure 8i RF PLUT 1
lookup table plot
Figure 8j RF PLUT 2
lookup table plot

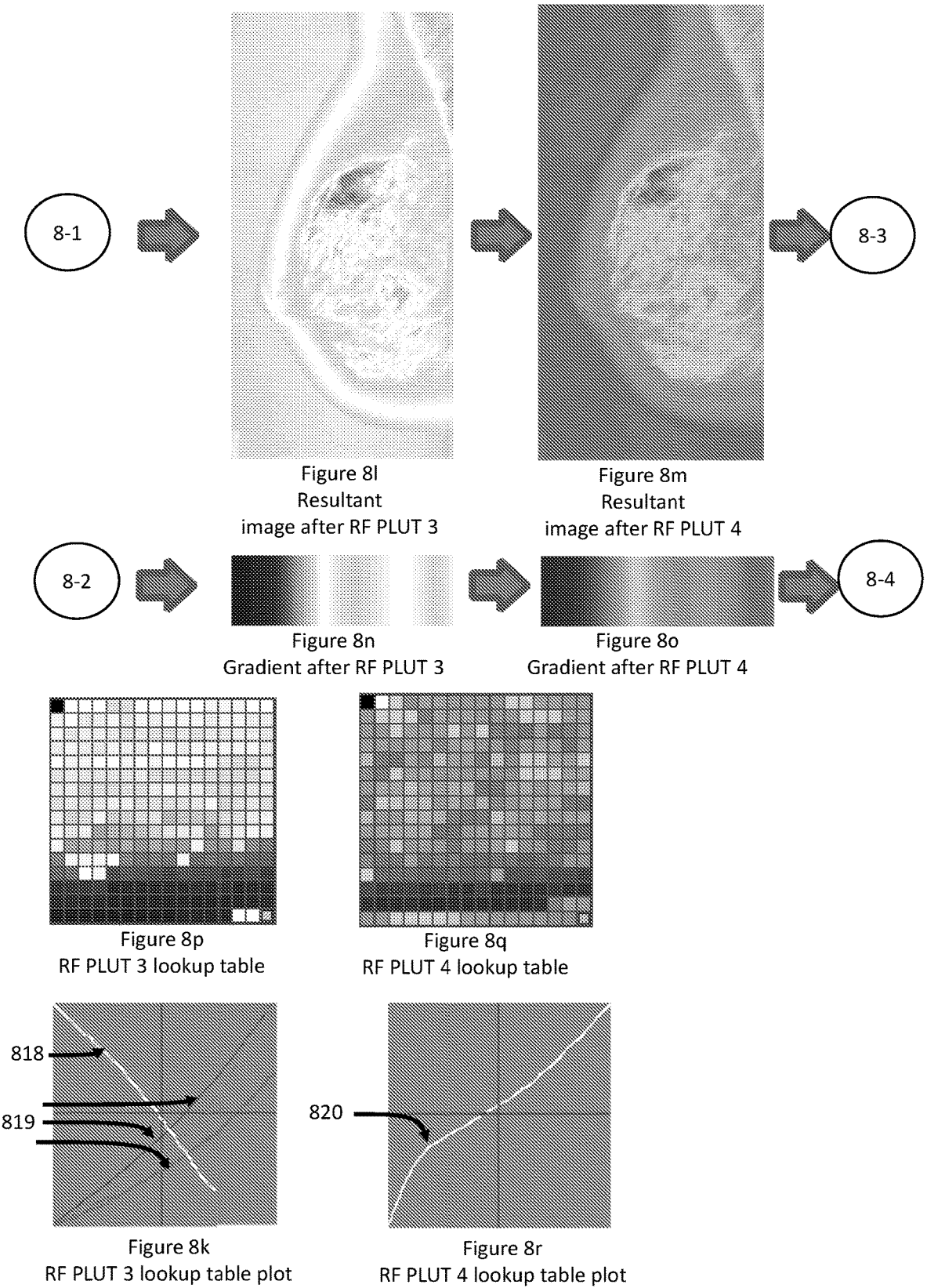

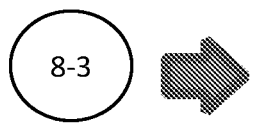 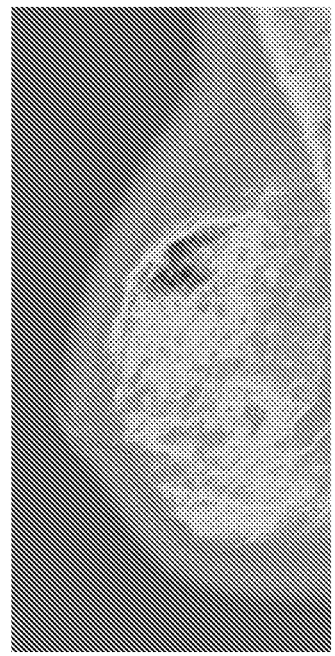
Figure 8s Resultant
image after RF blend and grayscale conversion
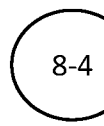 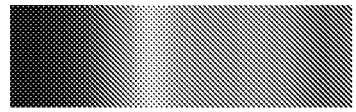
Figure 8t
Gradient after RF blend and grayscale conversion

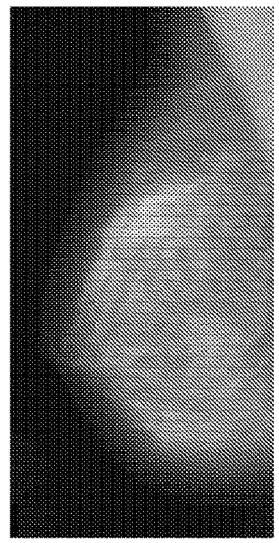
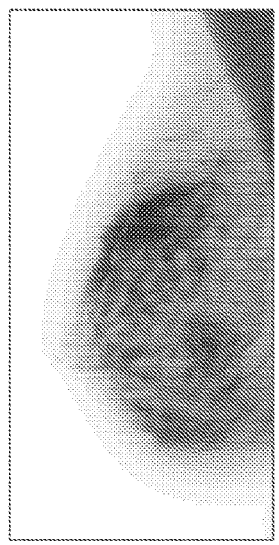
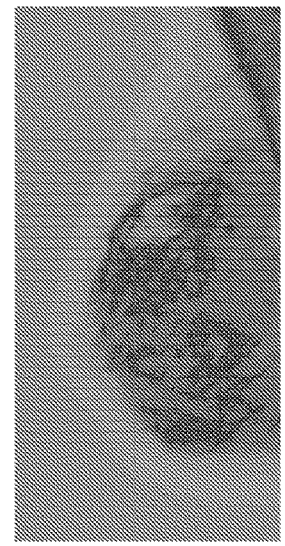
Figure 9a
Original Mammogram
Figure 9b
Resultant
image after GI PLUT 1
Figure 9c
Resultant
image after GI PLUT 2
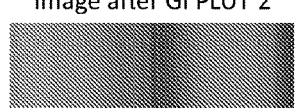
Figure 9d
Grayscale gradient
Figure 9e
Gradient after GI PLUT 1
Figure 9f
Gradient after GI PLUT 2
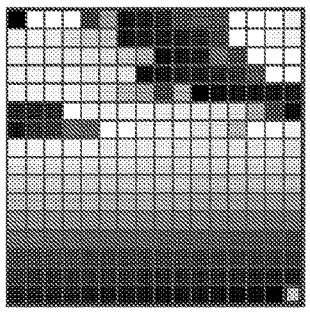
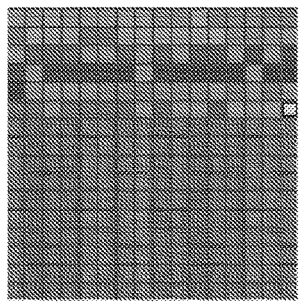
Figure 9g
GI PLUT 1 lookup table
Figure 9h
GI PLUT 2 lookup table
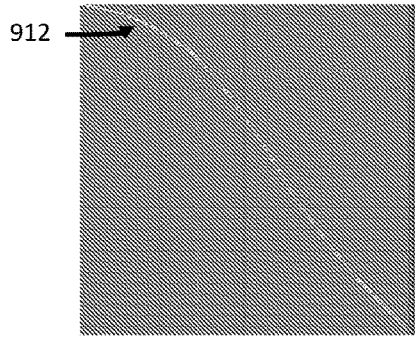
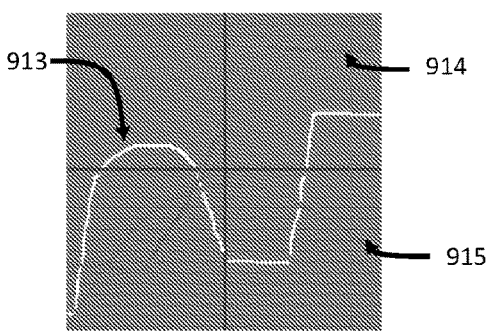
Figure 9i
GI PLUT 1 lookup table plot
Figure 9j
GI PLUT 2 lookup table plot

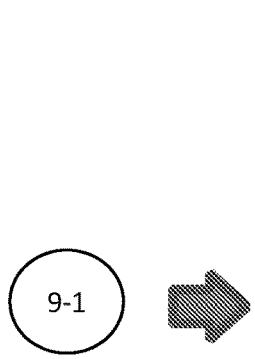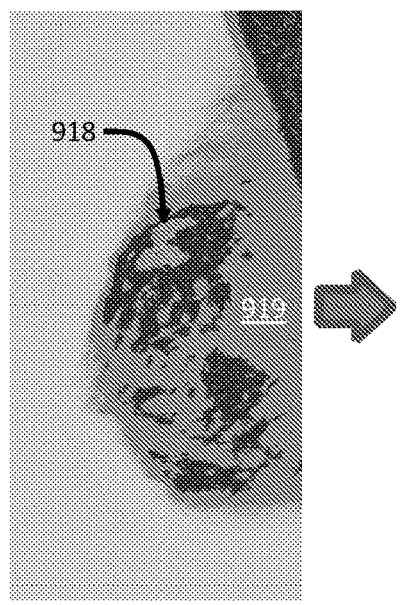
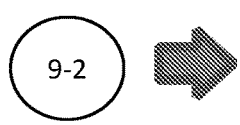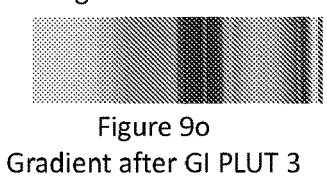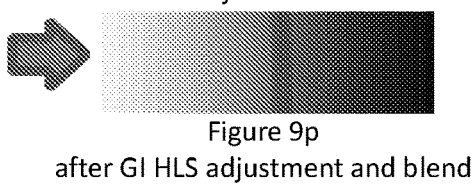
Figure 9m
Resultant
image after GI PLUT 3
Figure 9n
Resultant image
after GI HLS adjustment and blend
Figure 9o
Gradient after GI PLUT 3
Figure 9p
after GI HLS adjustment and blend
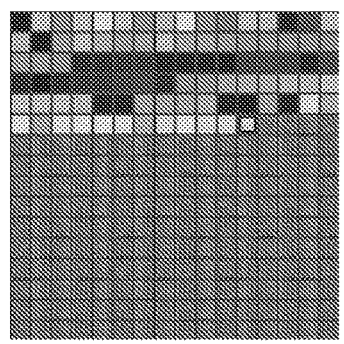
Figure 9k
GI PLUT 3 lookup table
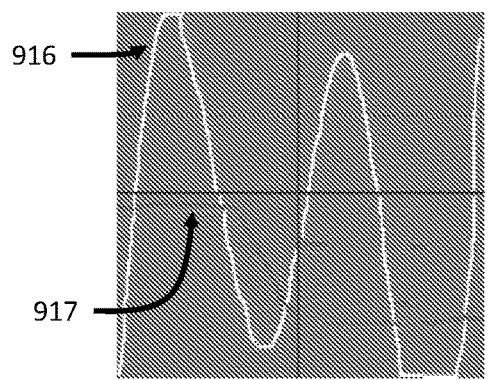
Figure 9l
GI PLUT 3 lookup table plot

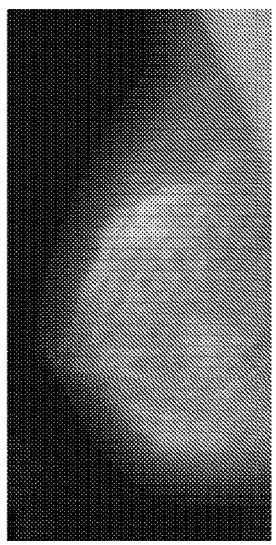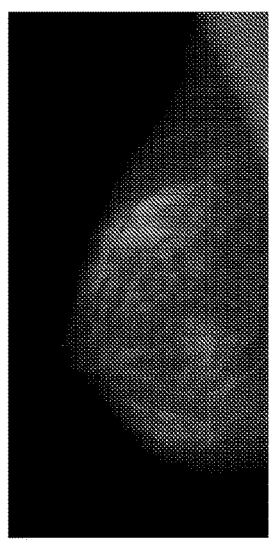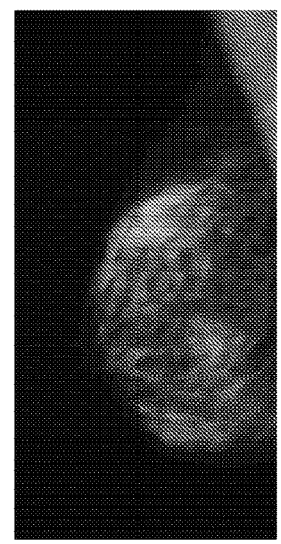
Figure 10a
Original Mammogram
Figure 10b
Resultant image after RB PLUT 1
Figure 10c
Resultant image after RB PLUT 2
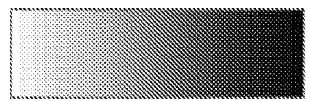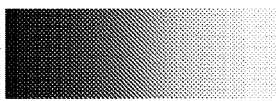
Figure 10d
Grayscale gradient
Figure 10e
Gradient after RB PLUT 1
Figure 10f
Gradient after RB PLUT 2
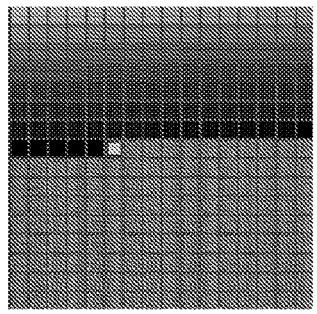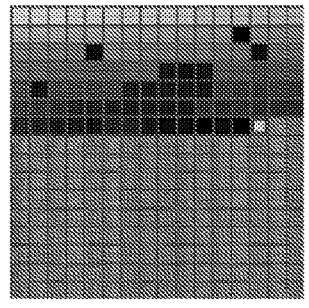
Figure 10g
RB PLUT 1 lookup table
Figure 10h
RB PLUT 2 lookup table
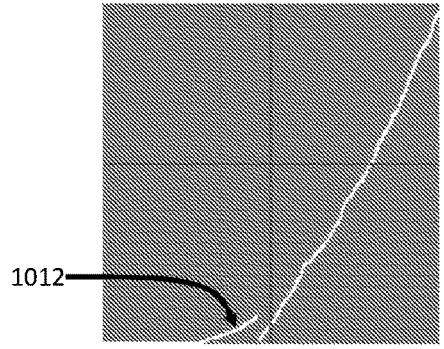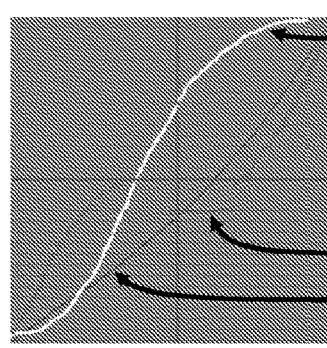
Figure 10i
RB PLUT 1 lookup table plot
Figure 10j
RB PLUT 2 lookup table plot

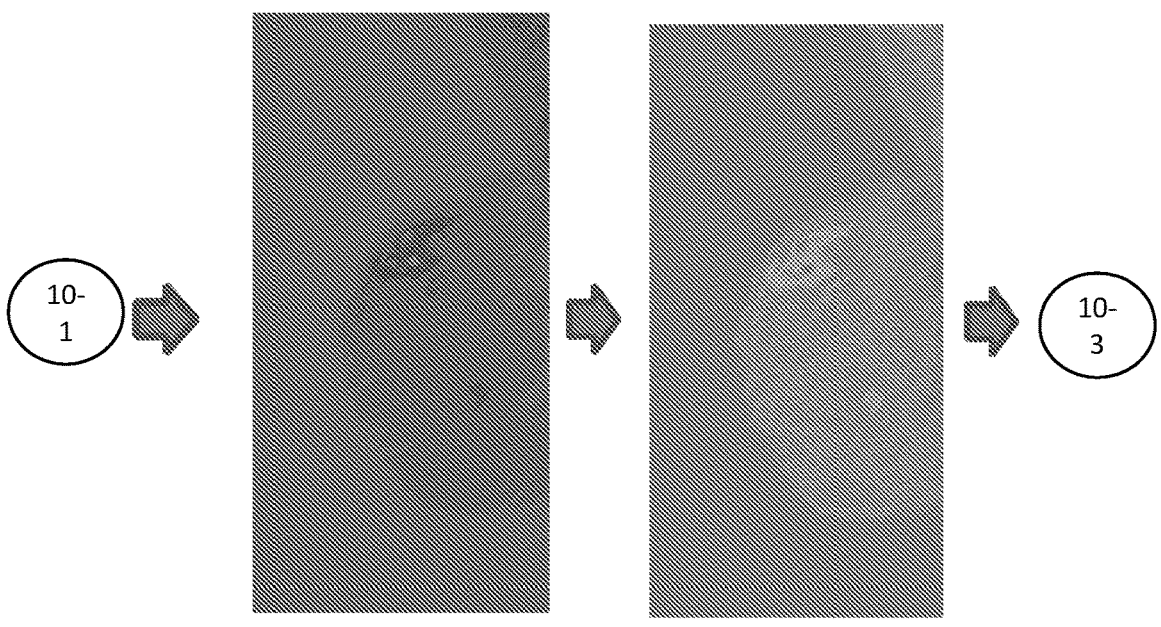
Figure 10m
Resultant image after RB PLUT 3
Figure 10n
Resultant image after Invert
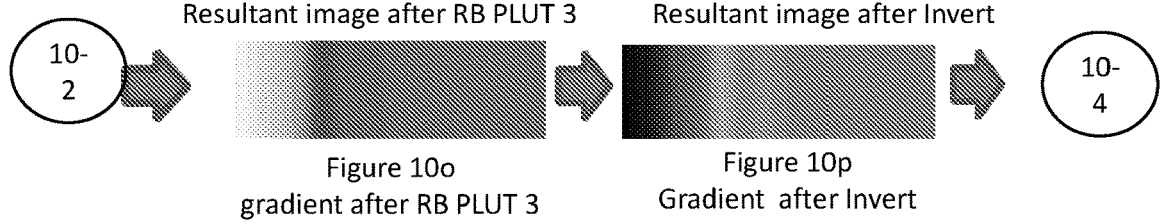
Figure 10o
gradient after RB PLUT 3
Figure 10p
Gradient after Invert
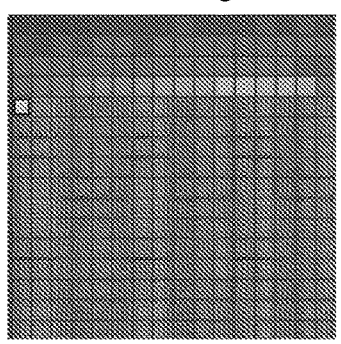
Figure 10k
RB PLUT 3 lookup table
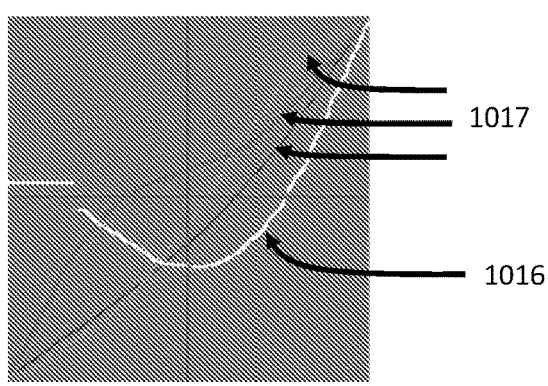
Figure 10l
RB PLUT 3 lookup table plot

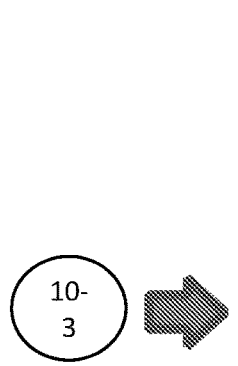
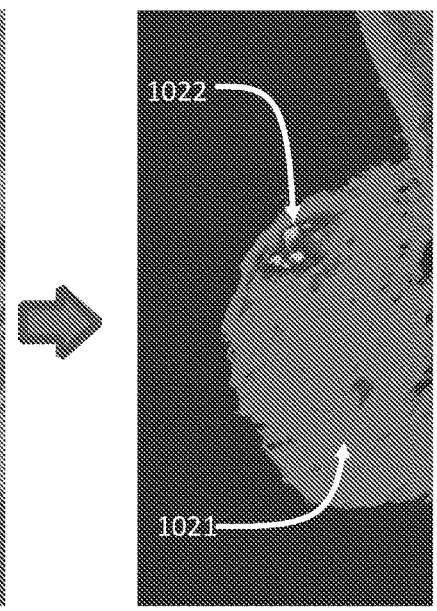
Figure 10s
Resultant image after RB PLUT 4
Figure 10t
Image after HLS adjustment
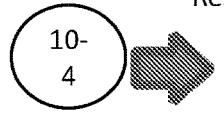
Figure 10u Gradient after RB PLUT 4
Figure 10v
Gradient after HLS adjustment
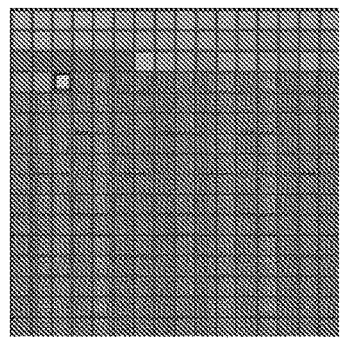
Figure 10q
RB PLUT 4 lookup table
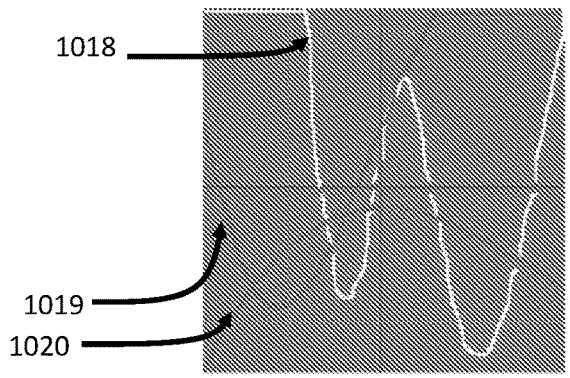
Figure 10r
RB PLUT 4 lookup table plot

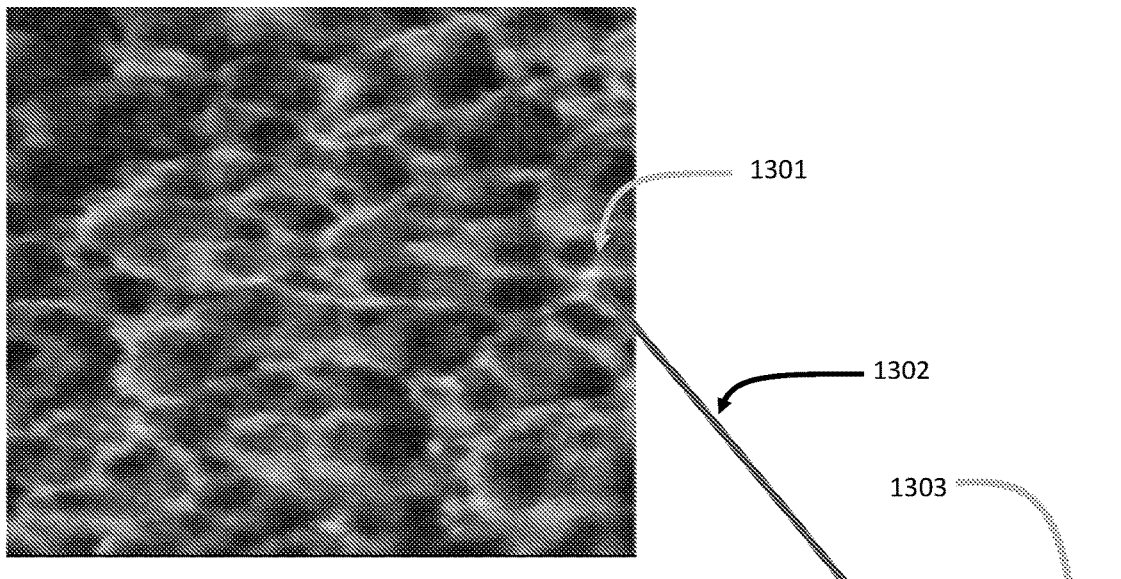
Figure 13a
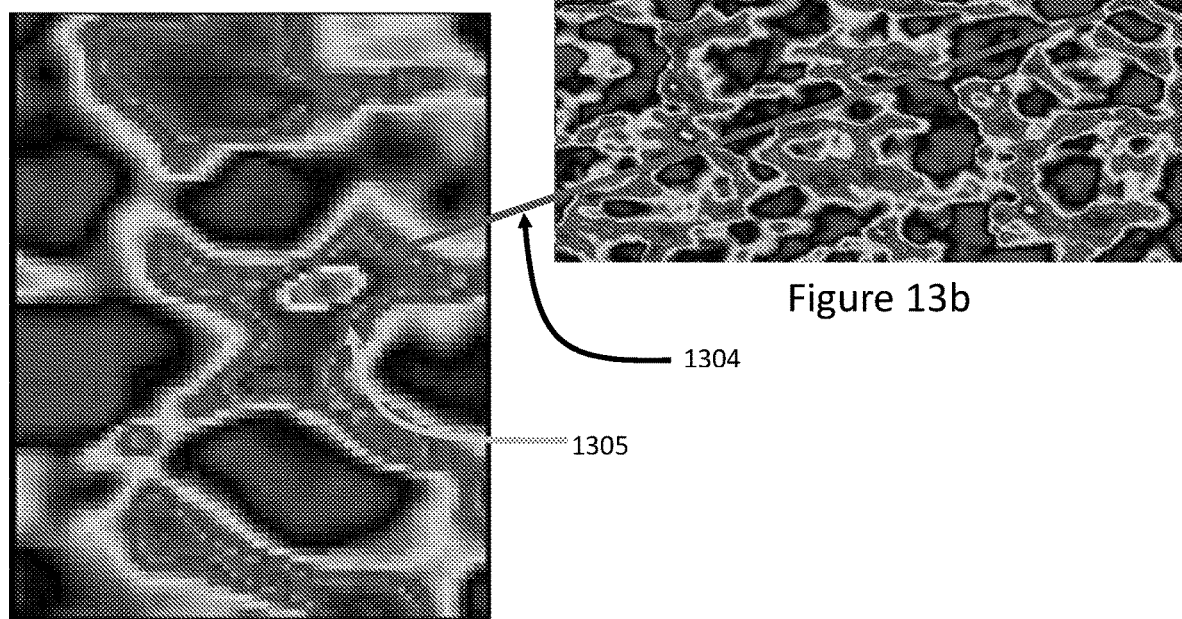
Figure 13c
Figure 13b

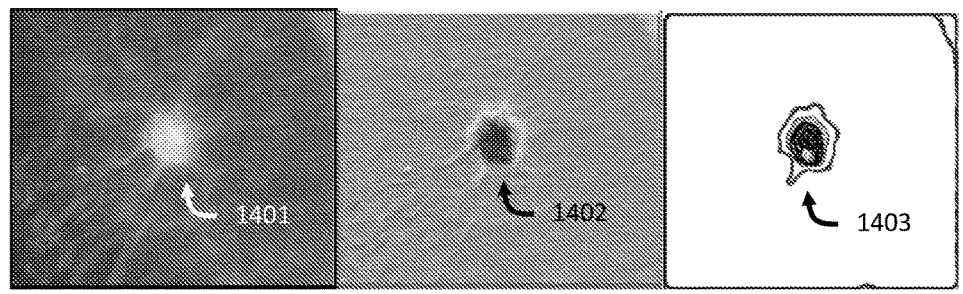
Figure 14a   Figure 14b   Figure 14c
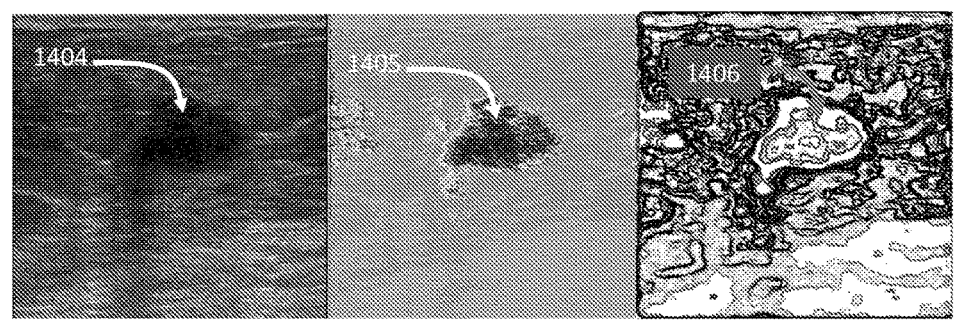
Figure 14d   Figure 14e   Figure 14f
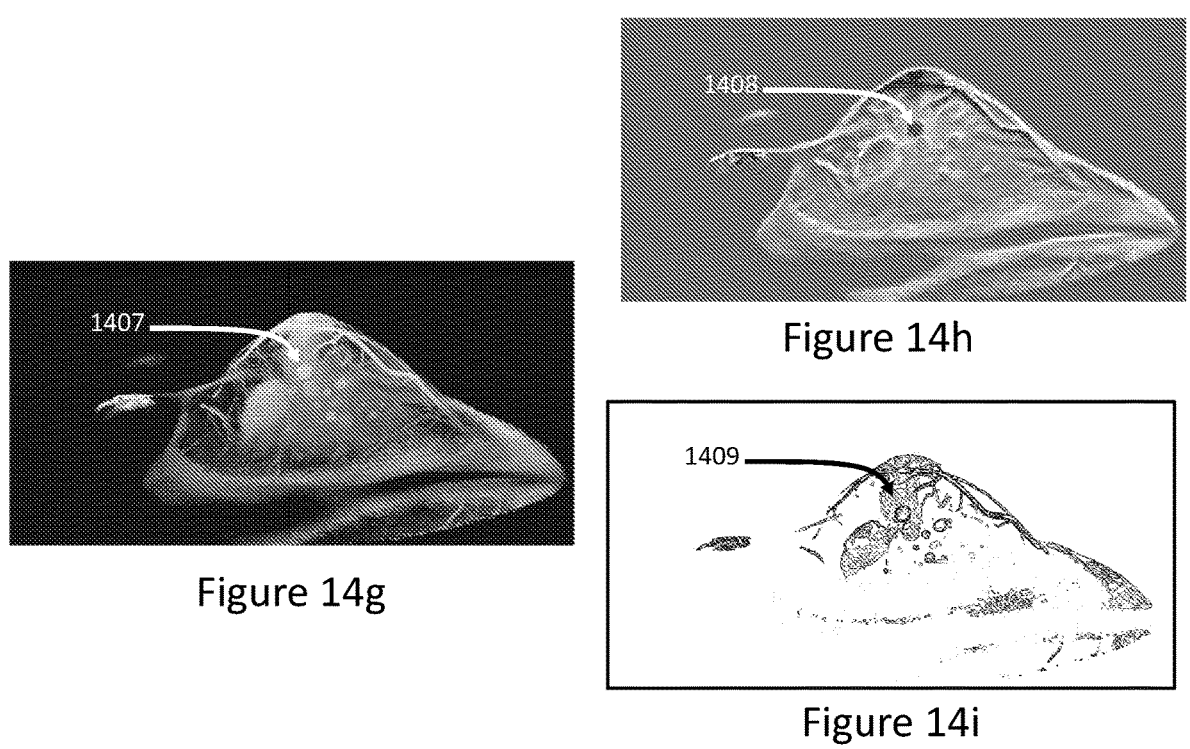
Figure 14g
Figure 14h
Figure 14i

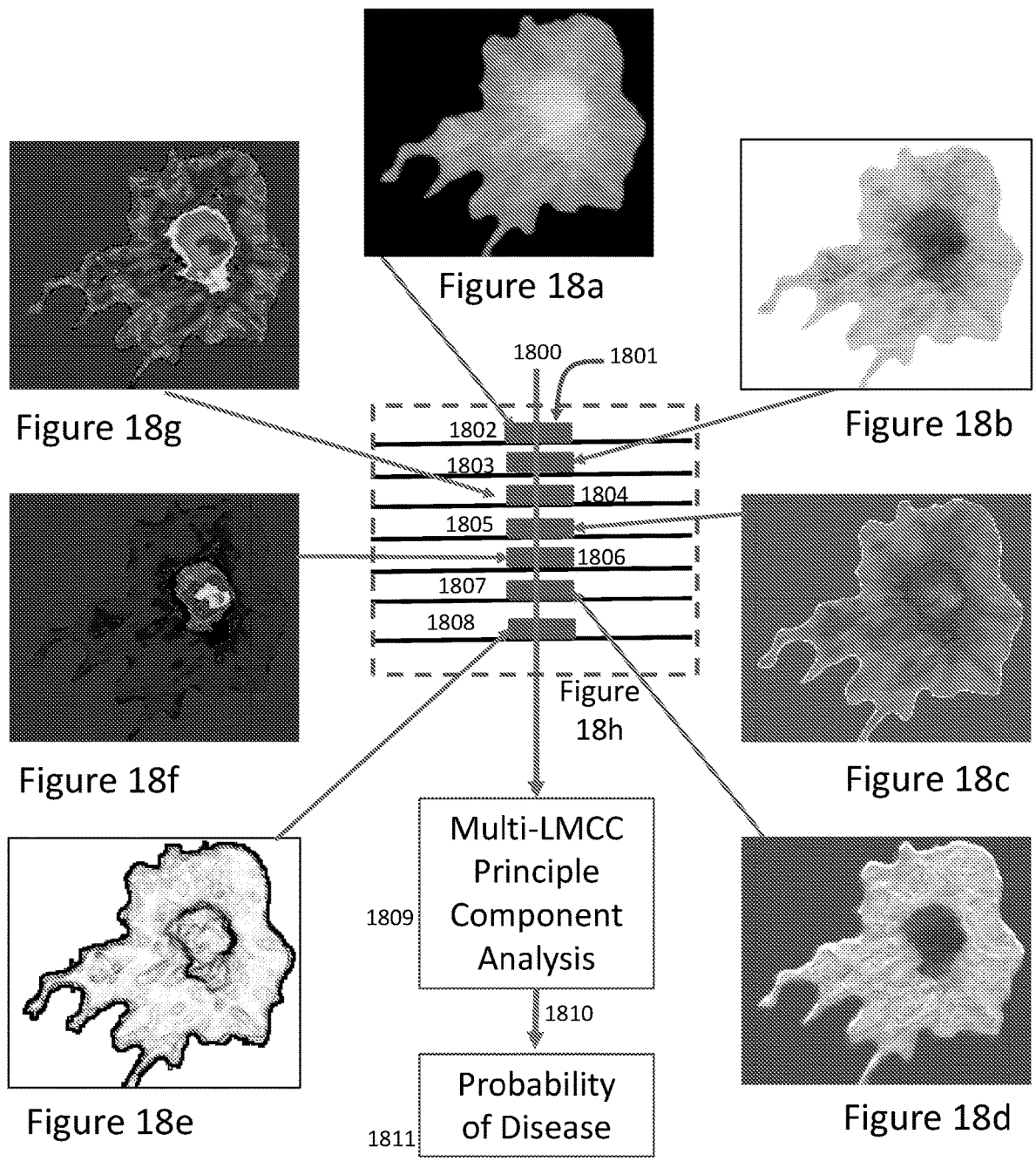

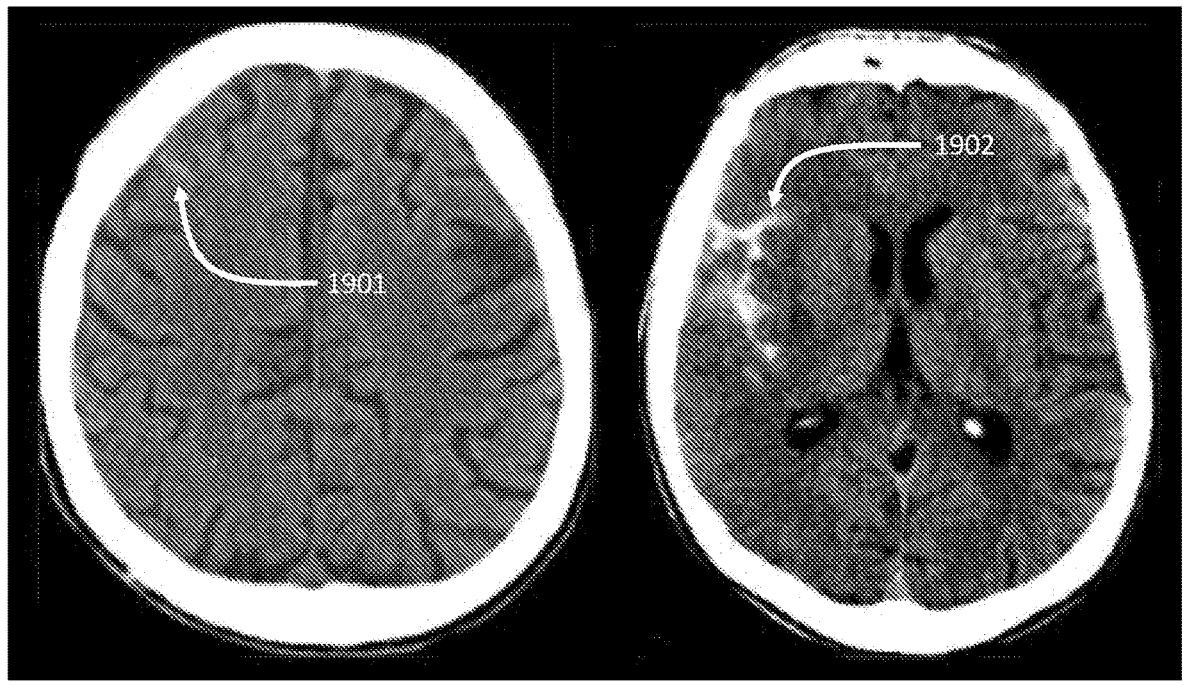
Figure 19a                   Figure 19b
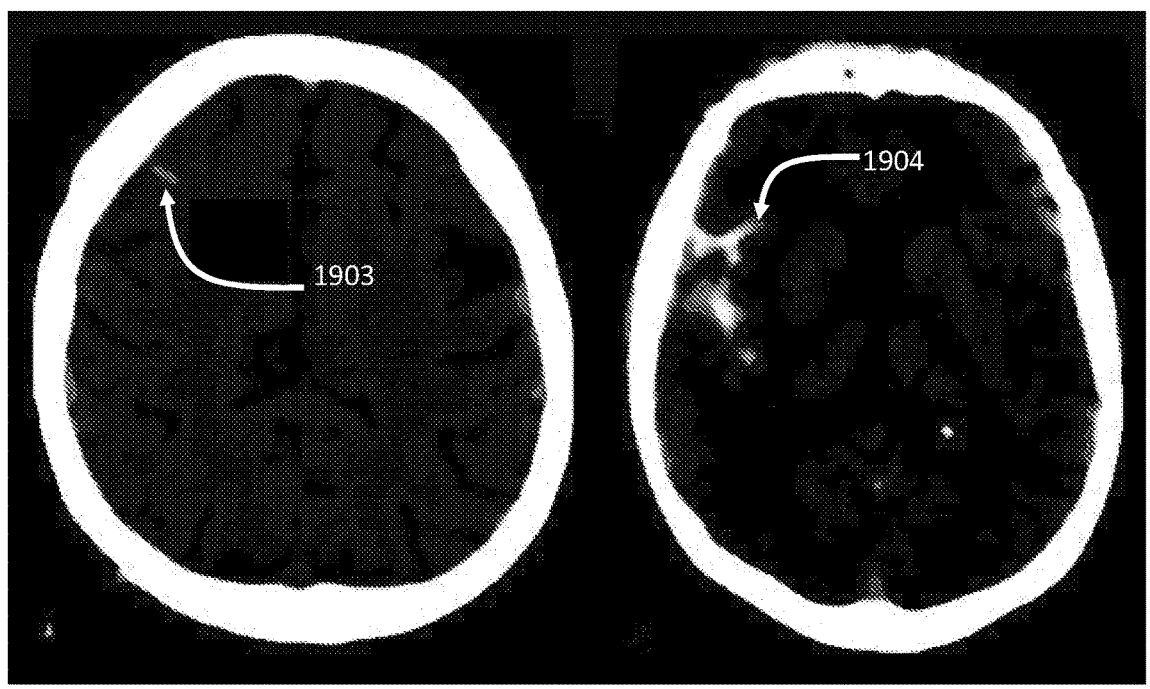
Figure 19c                   Figure 19d

 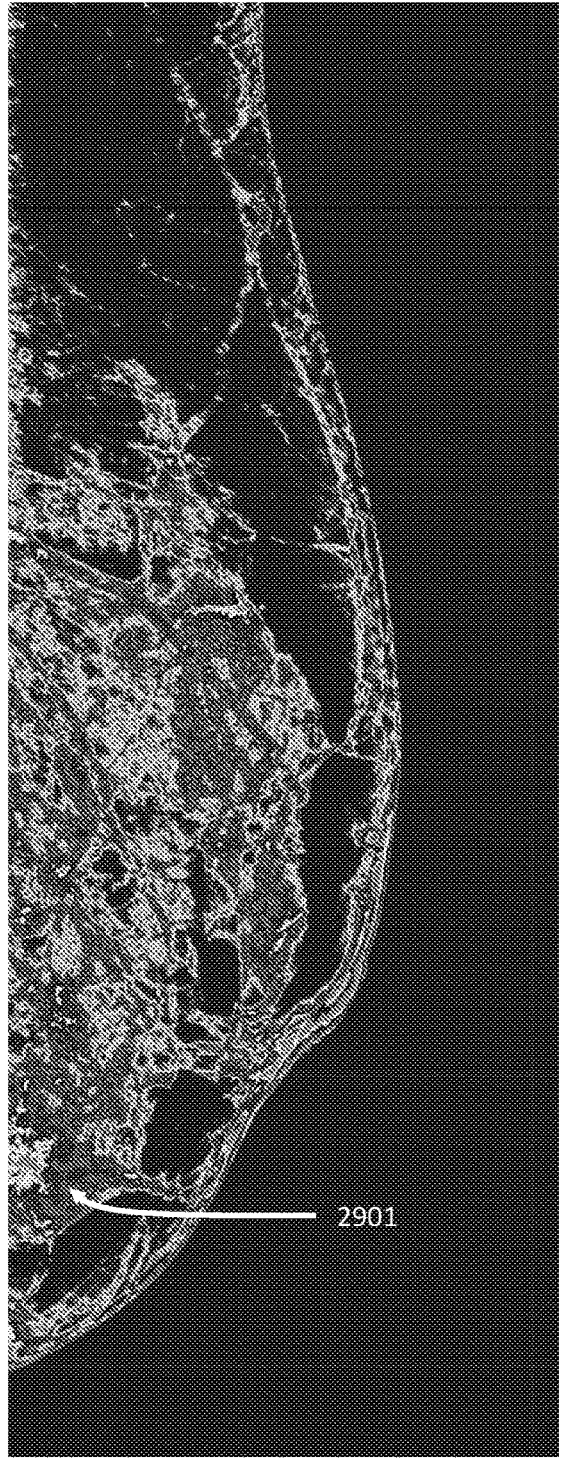
Figure 29a                                Figure 29b

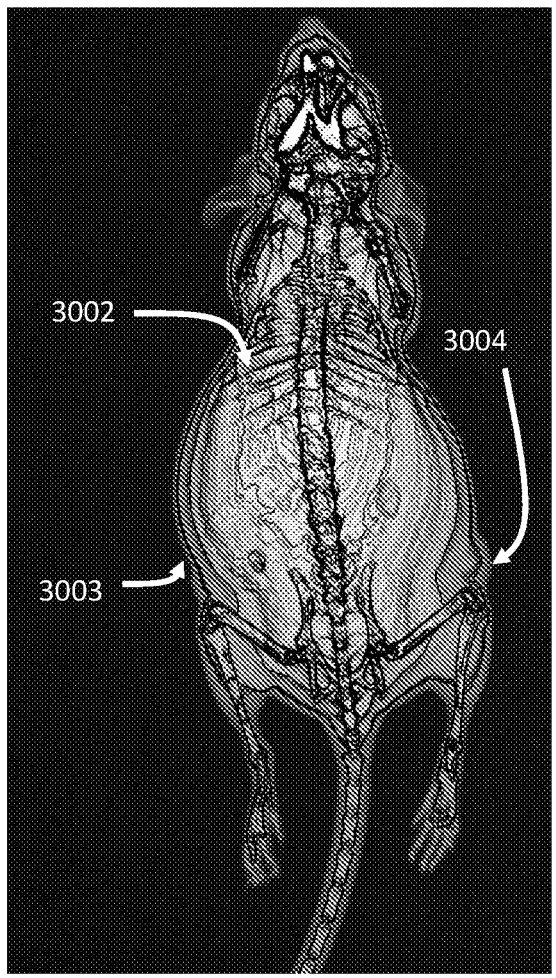
Figure 30c
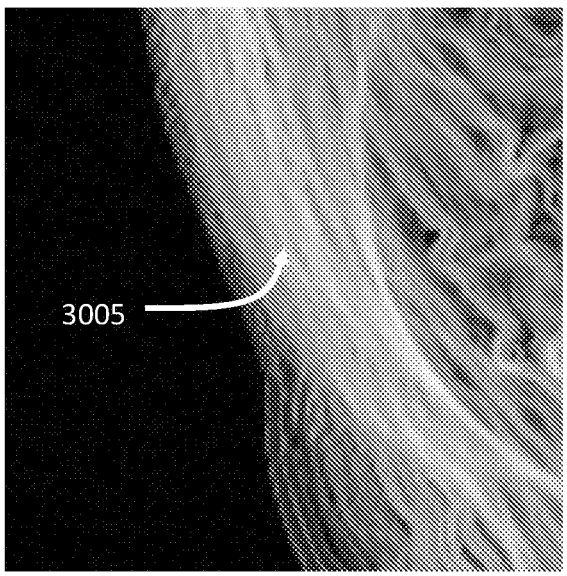 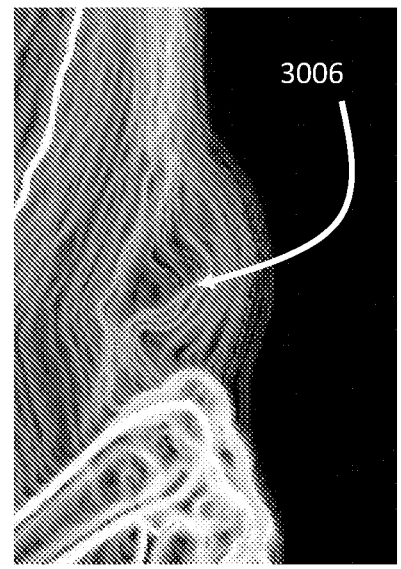
Figure 30d  Figure 30e

SYSTEM AND METHOD FOR THE VISUALIZATION AND CHARACTERIZATION OF OBJECTS IN IMAGES

CROSS REFERENCE TO RELATED APPLICATIONS

This application is a U.S. National Stage Entry of International Patent Application PCT/US2018/045567, filed Aug. 7, 2018, which claims priority to U.S. Provisional Patent Application No. 62/541,989 filed on Aug. 7, 2017, the contents of which are incorporated herein in their entireties.

BACKGROUND

The present invention generally relates to image processing and, more particularly, to a convergence-based system and method for the visualization and characterization of objects in images.

SUMMARY

In some embodiments, the convergence-based system may be known as local micro-contrast convergence (LMCC). LMCC algorithms may utilize an iterative approach that causes all tissues/materials in a digital image to express their structures in a way that is unique to each and every type of tissue.

Embodiments of the invention, described herein, may include methods that utilize an iterative approach that causes all tissues/materials in a digital image to express their structures in a way that is unique to each and every type of tissue.

Benoit B. Mandelbrot, in his book titled "The Fractal Geometry of Nature", revealed that Fractal Geometry (as compared with Euclidean Geometry) best expresses the irregular patterns of nature and biological growth. Fractal patterns often have the following properties: Non-integer dimensions, self-similarity, properties associated with symmetry and scalability.

LMCC mathematically deconvolves already existing fractal-like patterns of natural systems in digital images through an Iterated Function Model. Iteration of polynomials can create fractal patterns in a computer. Iteration of functions applied to digital images by LMCC algorithms causes local patterns of pixel neighborhoods to converge into characteristic patterns, independently of their luminance or color values. The convergence-based sequencing visualizes the complex (geometric/fractal-based) patterns into meaningful visual patterns for the characterization and analysis of those patterns for machine learning.

While some components of Imago's LMCC algorithmic sequences can distinctly express and differentiate tissue characteristics based on topology, others express fractal dimensions which can be expressed in non-integer values. Practically, this means that there are distinct "linear" patterns that reflect different tissue types. In one embodiment there is a convergence-based method of visualizing and characterizing all features in a first grayscale image, such that the first image is duplicated into at least two channels with identical luminance values, then applying a local micro-contrast convergence (LMCC) algorithm that transforms at least some of the input values of each duplicate channel so that the output pixel values of each duplicate channel are different from both its input pixel values and those of every other duplicate channel's output pixel values, then using a look-up table to map values for each vector in each channel that, as a process, collectively produces a second image that is different from the first image.

Channels may be created as grayscale, alpha, color information channels, or a combination of the three.

In a further embodiment, applying a second local micro-contrast convergence algorithm, separate and distinct from the first local micro-contrast convergence algorithm, to the second image to produce a third image that is separate and distinct from the first image and separate and distinct from the second image.

In a further embodiment, altering the third image by sequentially applying one or more additional local micro-contrast convergence algorithms to generate a fourth image.

In a further embodiment, combining one or more of the first, second, third or fourth images to produce a fifth image that is separate and distinct from the first, second, third or fourth images.

In a further embodiment, a local micro-contrast convergence algorithmic sequence may include one or more of the preceding types of multi-dimensional (multi-channel) image transformations.

In a further embodiment, multi-dimensional image transformations may be expressed as a profile look-up table (PLUT) in a digital file format as hexadecimal code or text.

In a further embodiment, multi-dimensional image transformations may be stored as a PLUT in a digital file format as one or more matrices.

In a further embodiment, local micro-contrast convergence algorithms define and can process a sequence of transformations utilizing metrics specified in PLUTs that translate image input pixel values representing specific material types to image output pixel values to cause relationships among neighboring pixel groups to aggregate into predictable color and luminosity patterns consistent with the material's structure and relationship to its imaging modality; each material is uniquely characterized and can be visually differentiated.

In a further embodiment, local micro-contrast convergence, multi-dimensional image transformations may be stored as a PLUT in a digital file format where a set of two-dimensional input functions $F_1(x,y,i)$, $F_2(x,y,i)$ ..., $F_N(x,y,i)$ is mapped to a set of two-dimensional output functions $G_1(x,y,i)$, $G_2(x,y,i)$ ..., $G_N(x,y,i)$ with space variables $(x, y)$ and luminance variable $(i)$.

In a further embodiment, multi-dimensional image transformations may be stored as a PLUT in a digital file format where a set of two-dimensional input functions $F_1(x,y,i)$, $F_2(x,y,i)$ ..., $F_N(x,y,i)$ is mapped to a set of more than two-dimensional output functions in the form of sub-matrices $G_1(x,y,i,j,k,l)$, $G_2(x,y,i,j,k,l)$ ..., $G_N(x,y,i,j,k,l)$ with space variables $(x,y)$, a luminance variable $(i)$, and alpha or color channels $(j,k,l)$.

In a further embodiment, a first grayscale image may be replicated into a first multi-dimensional space where each layer dimension of the multi-dimensional space is a replicate of the first image.

In a further embodiment, the number of dimensions in a multi-dimensional space equals two or more.

In a further embodiment, the number of dimensions in a multi-dimensional space equals four including luminance and the color components red, green, and blue.

In a further embodiment, the number of dimensions in a multi-dimensional space may equal N dimensions of color spaces such as Red, Green and Blue (RGB) (the RGB color model is an additive color model in which red, green and blue light are added together in various ways to reproduce a broad array of colors), Hue, Saturation, and Lightness (HSL), CIE XYZ (the International Commission on Illumination or CIE, which is the abbreviation for its French name, Commission internationale de l'eclairage, established the first system for scientifically defining light colors or additive colors.), and Cyan, Magenta, Yellow, and Black (CMYK is a combination of cyan, magenta, yellow and black.).

In a further embodiment, converting a multi-dimensional color space image that was created by a local micro-contrast convergence algorithmic sequence into a single channel [dimension] grayscale image.

In a further embodiment, converting a multi-dimensional color space image into a single channel grayscale image by differentially altering the luminance values of colors in the first image as they are expressed in the grayscale (desaturated) image.

In a further embodiment, the functions utilized within a local micro-contrast convergence algorithmic sequence can include superposition additive or differential operators utilizing two or more resultant images from two different local micro-contrast algorithmic sequences.

In a further embodiment, one or more local micro-contrast convergence algorithmic sequences may employ finite area convolution filters with an M×M (e.g., 3×3/5×5 . . . pixel arrays) impulse response array for either sharpening or reducing noise in an image.

In a further embodiment, the resulting features that are visualized and characterized can be expressed in the context of a given first grayscale image wherein each object or material type converges to similar patterns or colors characteristic of its type, thereby expressing unique characteristics in response to the algorithmic sequence.

In a further embodiment, different local micro-contrast convergence algorithmic sequences can be utilized for the same given first grayscale image to express different convergent visualizations and characterizations of materials within that image by causing all like materials to converge into similar patterns or colors.

In a further embodiment, different algorithmic sequences may be created and applied to optimize the characterization of distinct material properties in an image, such as object boundaries, textures, fine structures, and changes within objects.

In a further embodiment, the first image is an image generated by x-ray, ultrasound, infra-red, ultra-violet, Magnetic Resonance Imaging (MM), Computerized Axial Tomography (CAT or CT scans), Positron-Emission Tomography (PET) scans, grayscale, color, visible light, millimeter wave, or laser scan.

In a further embodiment, a cancer, cyst or any abnormality of the breast tissue the breast, prostate, kidney, liver, bone, lung, brain, or skin of either a human or animal can be visualized and characterized within the context and patterns of all other structures in an image.

In a further embodiment, a biomarker for cardiovascular disease, Alzheimer's disease, diseases of the eye, or multiple sclerosis lesion can be visualized and characterized within the context and patterns of all other structures in the image.

In a further embodiment, a chemical marker for solid or liquid organic compounds, such as explosives in an X-ray image, can be visualized and characterized within the context and patterns of all other structures in an image.

In a further embodiment, a structural defect or anomaly can be visualized and characterized within the context and patterns of all other structures in an image.

In one embodiment, there is a system of reducing the false positive error rate for visually or digitally expressing the presence of a feature in an image according to any of the methods described herein. In medical testing, and more generally in binary classification, a false positive is an error in data reporting in which a test result improperly indicates presence of a condition, such as a disease (the result is positive), when in reality it is not present.

In one embodiment, there is a method of reducing the false negative error rate for visually or digitally expressing the presence of a feature in an image comprising: applying a local micro-contrast tissue convergence algorithm to a first image to produce a second image that is different from the first image. In medical testing, a false negative is an error in which a test result improperly indicates no presence of a condition (the result is negative), when in reality it is present.

In a further embodiment, the first image is an image generated by x-ray, ultrasound, infra-red, ultra-violet, MRI, CT scans, PET scans, grayscale, color, visible light, millimeter wave, or laser scan.

In a further embodiment, a cancer, cyst or any abnormality of the breast tissue the breast, prostate, kidney, liver, bone, lung, brain, or skin of either a human or animal can be visualized and characterized within the context and patterns of all other tissue structures in an image.

In a further embodiment, a biomarker for cardiovascular disease, Alzheimer's disease, diseases of the eye, or multiple sclerosis lesion can be visualized and characterized within the context and patterns of all other structures in the image.

In a further embodiment, a chemical marker for a solid or liquid organic compound can be visualized and characterized within the context and patterns of all other structures in an image.

In a further embodiment, a structural defect or anomaly can be visualized and characterized within the context and patterns of all other structures in an image.

In a further embodiment, the false negative rate for breast cancer detected or visualized by a radiologist in the second (i.e., subsequent) image is less than 16% for normal breasts and less than 60% for breasts having a portion of dense tissue.

In one embodiment, there is a system of reducing the false negative error rate of detecting or revealing a feature in an image according to any of the methods described herein.

In one embodiment there is a system comprising: one or more memory units each operable to store at least one program; and at least one processor communicatively coupled to the one or more memory units, in which the at least one program, when executed by the at least one processor, causes the at least one processor to perform the steps of: receiving an image; mapping pixel values of the image to an initial multi-dimensional color space; applying one or more local micro-contrast convergence transfer functions to the image's initial multi-dimensional color space to cause local micro-contrast convergence and to create a processed image with a multi-dimensional color space; and displaying that image visualization based on the processed multi-dimensional color space.

In a further embodiment, converting the processed multi-dimensional color space image to a single channel grayscale image.

In a further embodiment, the multi-dimensional color space image includes a luminance dimension having luminance values.

In a further embodiment, converting the processed multi-dimensional color space to a single channel grayscale image by differentially altering the luminance values of colors in the first image as they are expressed in the grayscale (desaturated) image for purposes of image display or analysis.

In a further embodiment, the multi-dimensional color space is an RGB color space.

In some embodiments, the multi-dimensional color space may be one of: HSV (Hue, Saturation, Value), HSL, HSB (hue, saturation, brightness), CMYK, CIE XYZ or CIELAB (The CIELAB color space, also known as CIE L*a*b* or sometimes abbreviated as simply "Lab" color space is a color space defined by the International Commission on Illumination,CIE). It expresses color as three numerical values, L* for the lightness and a* and b* for the green-red and blue-yellow color components).

In a further embodiment, the system further comprising the processing of a breast image (mammogram, CT, MRI, or ultrasound): applying a median filter to the initial multi-dimensional color space; and wherein applying the one or more PLUTs to the initial multi-dimensional color space includes: applying a first set of PLUT functions to attenuate low density fatty breast tissue (as defined by the American College of Radiology (ACR) density classification system); applying a second set of PLUT functions to cause fatty breast tissue to appear as a first color and to differentiate the denser breast tissue (as defined by the American College of Radiology (ACR) density classification system) using other colors; applying a third set of PLUT functions to amplify low pixel values and attenuate high pixel values in the color space layer associated with the first color; and applying a fourth set of PLUT functions to change the background of the image, when displayed, to black or other desired luminance or color value.

In a further embodiment, the system further comprising: receiving a second image, the second image being substantially similar to the first image; mapping pixel values of the second image to a second initial multi-dimensional color space; applying a median filter and a convolution filter to the initial multi-dimensional color space to create a second processed multi-dimensional color space; and displaying an image visualization based on the processed multi-dimensional color space associated with the first image and the second processed multi-dimensional color space associated with the second image, and wherein the applying the one or more PLUT functions to the initial multi-dimensional color space associated with the first image includes: applying a first set of PLUT functions to elevate darker values of the image and attenuate mid tones; applying a second set of PLUT functions to the multi-dimensional color space to add subtle color hues; and applying a third set of PLUT functions to expand the tonal values associated with cancer.

In a further embodiment, the system further comprising: adjusting gamma levels of the multi-dimensional color space to adjust the contrast of the first image and highlight structural details, and wherein the applying the one or more PLUT functions to the initial multi-dimensional color space associated with the first image includes: applying a first set of PLUT functions to diminish the luminance levels slightly; and applying a second set of PLUT functions to invert values of the initial multi-dimensional color space associated with luminance.

In a further embodiment, the first image is a mammogram that includes dense tissue and fatty tissue (as defined by the American College of Radiology (ACR) density classification system), and applying a first local micro-contrast convergence algorithm to a first image to produce a second image that is separate and distinct from the first image includes: mapping pixel values of the first image to a first multi-dimensional color space; applying a median filter to the first multi-dimensional color space to produce a second multi-dimensional color space; inverting the second multi-dimensional color space to produce a third multi-dimensional color space; applying a first set of one or more non-linear transfer functions to the third multi-dimensional color space to produce a fourth multi-dimensional color space and to cause fatty breast tissue to appear as one color and to differentiate the denser breast tissue using other colors; applying a second set of one or more transfer functions to the fourth multi-dimensional color space to produce a fifth multi-dimensional color space and to amplify high pixel values and attenuate low pixel values and to highlight the breast area structures; and displaying an image visualization based on the fifth multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause fatty breast tissue to appear as one color and to differentiate the denser breast tissue using other colors; converting the second multi-dimensional color space to a third multi-dimensional color space in an HLS color space; and displaying an image visualization based on the third multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause fatty breast tissue to appear as one color and to differentiate and reveal detailed structures in the denser breast tissue using other colors; and displaying an image visualization based on the second multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause fatty breast tissue to appear translucent and to differentiate denser breast tissue (as defined by the American College of Radiology (ACR) density classification system) using other colors, and to distinguish small dot-like structures; and displaying an image visualization based on the second multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying median filter to the first multi-dimensional color space to produce a second multi-dimensional color space; applying a convolution filter to the second multi-dimensional color space to produce a third multi-dimensional color space; importing a duplicate first image; mapping image pixel values to a fourth multi-dimensional color space; applying a first set of one or more transfer functions to the fourth multi-dimensional color space to produce a fifth multi-dimensional color space and to build contrast and darken fatty tissue; applying a second set of one or more transfer functions to the fifth multi-dimensional color space to produce a sixth multi-dimensional color space and to build contrast and darken fatty tissue; applying a third set of one or more transfer functions to the sixth multi-dimensional color space to produce a seventh multi-dimensional color space and to invert fatty breast tissue luminance to appear as one color and to differentiate and reveal detailed structures in the denser breast tissue using other colors; applying a fourth set of one or more transfer functions to the seventh multi-dimensional color space to produce an eighth multi-dimensional color space and to define the breast boundary; merging the third multi-dimensional color space with the eighth multi-dimensional color space to produce a ninth multi-dimensional color space; converting the ninth multi-dimensional color space to grayscale values and displaying an image representative of the ninth multi-dimensional color space.

In a further embodiment, the first image is a mammogram that includes dense tissue and fatty tissue, and wherein applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause the image pixel values to invert non-linearly; applying a second set of one or more transfer functions to the second multi-dimensional color space to produce a third multi-dimensional color space and to cause fatty breast tissue to appear as one color and to differentiate and reveal detailed structures in the denser breast tissue using other colors; applying a third set of one or more transfer functions to the third multi-dimensional color space to produce a fourth multi-dimensional color space and to cause fatty breast tissue to appear as one color and to differentiate and reveal detailed structures in denser breast tissue using other colors; converting the fourth multi-dimensional color space to a fifth multi-dimensional color space in an HLS color space; merging the fifth multi-dimensional color space with the first multi-dimensional color space by employing a darken blend to produce a sixth multi-dimensional color space; adjusting the opacity of the sixth multi-dimensional color space to produce a seventh multi-dimensional color space; and converting the seventh multi-dimensional color space to grayscale values and displaying an image representative of the seventh multi-dimensional color space.

In a further embodiment, the first image is a mammogram that includes dense tissue and fatty tissue, and wherein applying a first local micro-contrast convergence algorithm to a first image to produce a second image that is separate and distinct from the first image includes: mapping pixel values of the first image to a first multi-dimensional color space; applying median filter to the first multi-dimensional color space to produce a second multi-dimensional color space; applying a first set of one or more transfer functions to the second multi-dimensional color space to produce a third multi-dimensional color space and to alter the contrast and reduce luminosity of fatty tissue; applying a second set of one or more transfer functions to the third multi-dimensional color space to produce a fourth multi-dimensional color space and to colorize all breast tissue except those of the higher density; applying a third set of one or more transfer functions to the fourth multi-dimensional color space to produce a fifth multidimensional color space and to reduce the fatty tissue to an almost solid color; inverting the colors of the fifth multi-dimensional color space to produce a sixth multi-dimensional color space; applying a fourth set of one or more transfer functions to the sixth multi-dimensional color space to produce a seventh multi-dimensional color space and to differentiate the breast from outside its boundary; converting a seventh multi-dimensional color space to an eighth multi-dimensional color space in an HLS color space and adjust HLS properties of the eighth multi-dimensional color space to produce a ninth multi-dimensional color space; displaying an image visualization based on the ninth multi-dimensional color space.

In one embodiment, there is a method performed by the system described herein.

BRIEF DESCRIPTION OF THE SEVERAL VIEWS OF THE DRAWINGS

The foregoing summary, as well as the following detailed description of embodiments of the invention, will be better understood when read in conjunction with the appended drawings of an exemplary embodiment. It should be understood, however, that the invention is not limited to the precise arrangements and instrumentalities shown.

In the drawings:

FIGS. 4a to 4k is an exemplary local micro-contrast convergence algorithmic sequence to process mammographic images to reveal breast abnormalities in resultant color images, in accordance with an exemplary embodiment of the present invention;

FIGS. 6a to 6i is an exemplary local micro-contrast convergence algorithmic sequence to process mammographic images to reveal details in dense breast tissues in resultant grayscale images. in accordance with an exemplary embodiment of the present invention;

FIGS. 7a to 7j is an exemplary local micro-contrast convergence algorithmic sequence to process mammographic images to reveal the presence of microcalcifications in dense breast tissues in resultant grayscale images, in accordance with an exemplary embodiment of the present invention;

FIGS. 8a to 8u are an exemplary local micro-contrast convergence algorithmic sequence to process mammographic images to reveal details of very fine breast tissue structures in resultant grayscale images, in accordance with an exemplary embodiment of the present invention;

FIGS. 9a to 9q is an exemplary local micro-contrast convergence algorithmic sequence to process mammographic images to reveal breast abnormalities in resultant grayscale images, in accordance with an exemplary embodiment of the present invention;

FIGS. 10a to 10w are an exemplary local micro-contrast convergence algorithmic sequence to process mammographic images to isolate breast abnormalities in resultant grayscale images, in accordance with an exemplary embodiment of the present invention;

FIG. 13a is an original image revealing the surface of a cancer cell, in accordance with an exemplary embodiment of the present invention;

FIG. 13b depicts the results after applying an exemplary local micro-contrast convergence algorithmic sequence to the image in FIG. 13a in accordance with an exemplary embodiment of the present invention;

FIG. 13c depicts a close-up of on area of FIG. 13b, in accordance with an exemplary embodiment of the present invention;

FIGS. 14a to 14i are an exemplary local micro-contrast convergence algorithmic sequence to process breast images generated from different imaging modalities, in accordance with an exemplary embodiment of the present invention;

FIG. 18a-18g is an exemplary methodology for correlating metrics from each of a plurality of processed images, in accordance with an exemplary embodiment of the present invention;

FIGS. 19a and 19b are original CT scans of a patient who had had a concussion, in accordance with an exemplary embodiment of the present invention;

FIGS. 19c and 19d depict the results after applying an exemplary local micro-contrast convergence algorithmic sequence to the original images in FIGS. 19a and 19b respectively, in accordance with an exemplary embodiment of the present invention;

FIG. 29a is an original X-ray mammographic image, in accordance with at least one embodiment of the present invention;

FIG. 29b shows the results after applying an exemplary local micro-contrast convergence algorithmic sequence to the original mammogram in FIG. 29a in accordance with at least one embodiment of the present invention;

FIG. 30c shows the results after applying an edge detection filter to the exemplary local micro-contrast convergence algorithmic image in FIG. 30b, in accordance with at least one embodiment of the present invention;

FIG. 30d is a close up of the left side of the X-ray of the mouse in FIG. 30c, in accordance with at least one embodiment of the present invention;

FIG. 30e is a close up of the right side of the mouse in FIG. 30c, in accordance with at least one embodiment of the present invention;

DETAILED DESCRIPTION

Figure 1A:
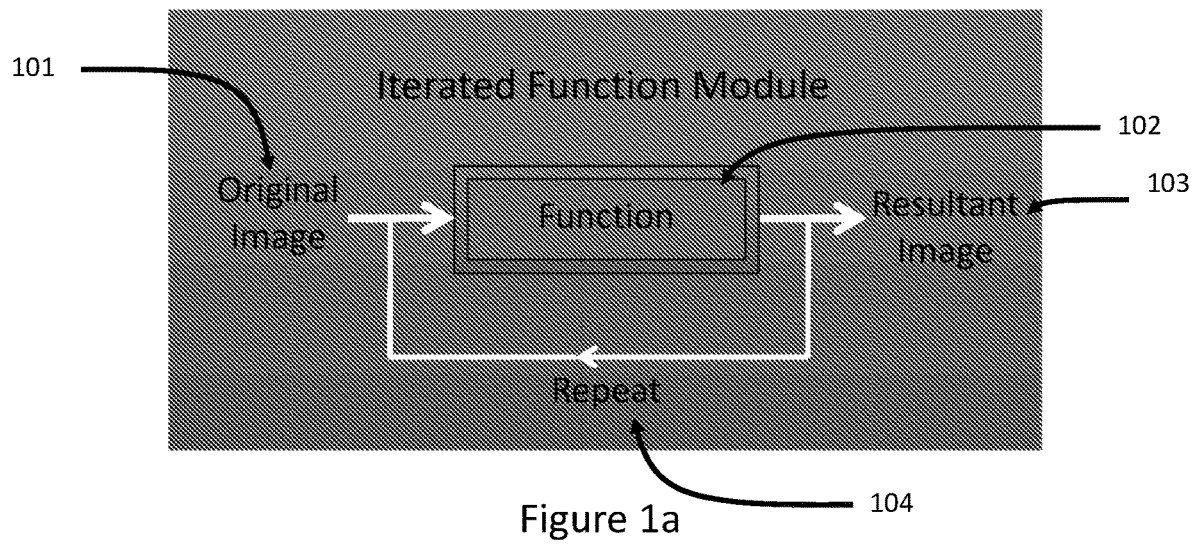
FIG. 1a depicts a diagram illustrating the elements of an Iterated Function Module in accordance with an exemplary embodiment of the present invention.

Referring to the drawings in detail, wherein like reference numerals indicate like elements throughout, there is shown in FIGS. 1a-36b systems, devices and methods, generally designated, in accordance with exemplary embodiments of the present invention.

Introduction

Most image processing and analysis methodologies in medicine, for example, are designed to cause areas within an image to diverge, bifurcate, or be isolated as areas of interest (AOIs). In these processes, the AOIs may become isolated by applying one or more sequences of segmentation algorithms. Many image processing and analysis methodologies, known as computer aided detection (CAD) processes, may be designed to be used for identifying the presence of breast cancer in mammograms, other diseases in other modalities, and for applications outside of medicine. Results of studies have shown that, the CAD processes used in breast image analysis have false positive rates of up to 5,000 to 1. The false positive rate is the ratio between the number of negative events wrongly categorized as positive (false positives), and the total number of actual negative events.

It is the process of visual or data segmentation of objects of interest, the bifurcating of objects in an image, and/or the subsequent isolation from other tissues of the image (divergence), that greatly limits the effectiveness of such techniques to clinicians. Because bifurcating/segmenting processes remove the context of surrounding objects/tissues from any larger context in which the AOIs occur, the diagnostic value of such processes to doctors are greatly limited since the location of disease or abnormality within the breast and its surrounding tissues limits its use in making improved clinical decisions on possible outcomes and treatments.

Many mathematical approaches have been devised to examine original grayscale images by utilizing local properties within the image such as luminance values, running mean filters, rubber-band straightening transforms, measurements of circularity at a suspected region of interest, texture, gradient histogram, and gray level increment analysis. Many of these approaches fail to produce acceptable results in areas of the image where the objects to be detected are very similar to the values of the surrounding neighborhood values. A cancer may be detected, but its margins (boundaries) may not be clearly established. Still others, utilize machine learning where an atlas of known pathology is compared with an image being processed for determining a probability of likelihood based on similarities between the atlas and the unknown set of image metrics in the image being analyzed.

In addition, many CAD methodologies may not improve visualization and characterization of objects in the processed image as an aid to the radiologist to visually confirm the extent of the abnormalities or distinguish characteristics of abnormalities from normal tissue. Instead, CAD approaches may simply place a location marker within an original mammogram image. This further provides a dilemma for a radiologist in that no additional discriminating visual information is available to assess the validity of the marker. Using CAD methodologies, the radiologist must not only assess the original image for the presence of cancer or other abnormalities as defined by the American College of Radiology (ACR), but also assess the validity of a given marker, while being aware of the very high false positive rate associated with the CAD process. Similar deficiencies may exist in a broad spectrum of fields that use CAD methodologies or image segmentation algorithmic approaches.

Thus, there is a need in the art to improve image-processing techniques beyond those of CAD, bifurcating, or divergence-based processes.

Breast Cancer Imaging Domain Application

Mammography is the use of X-ray radiographs to generate an image of a person's breast to detect the possible presence of breast cancer or other abnormalities. While the use of mammograms is currently the best methodology available for screening to detect breast cancer, between 10% and 30% of women with cancer are reported as negative (i.e., cancer free). This may be due in part to the very complex, and often very subtle nature of detecting cancer in mammographic images and is especially a serious issue for women with dense breast tissue (as defined by the American College of Radiology (ACR) density classification system) who have a higher potential of getting breast cancer. Cancer in mammograms appears white, yet the breast contains non-cancerous elements that also appear white (e.g., dense breast tissue) and dark (e.g., fatty breast tissue). Radiologists more easily observe cancers in fatty tissue, yet cancers occurring in dense breast tissue are very difficult to distinguish from surrounding tissue. Almost 40% of women have breasts that contain at least a portion of dense tissue; consequently, there is a significant need to be able to distinguish cancerous lesions regardless of the level or relative amount of density in a woman's breast tissue.

Moreover, when a radiologist determines that breast cancer may be present in a mammogram several possible follow-up procedures may be employed. These may include the use of ultrasound, MRI with contrast, breast CT scans, and biopsies. These follow-up procedures are expensive, are frequently emotionally traumatic to the patient and their family and, in some instances, can cause physical trauma. The positive predictive value of ultrasound, when indicating the need for a biopsy, is only 9%. Clinically, 91% of patients who have biopsies following ultrasound are confirmed by pathology as not having cancer. Similarly, 60% of patients having an MM and going on to biopsy do not have cancer. As used herein, positive predictive values refer to the probability that subjects with a positive screening test have the disease. As used herein, negative predictive value may refer to the probability that subjects with a negative screening test do not have the disease.

Ultrasound patients who have indications of possible disease in a mammogram may be sent to have an ultrasound or have an MM exam with contrast. When ultrasound is performed, and a radiologist determines from the ultrasound image that a cancer might be present, a biopsy is often recommended. Of those patients that had a follow-up biopsy, based on an ultrasound, 91% did not have cancer.

An approach that can reveal cancer with a high degree of sensitivity and specificity and utilizing only standard screening and inexpensive imaging (e.g., mammograms) will provide a breakthrough in today's cancer detection environment. Approximately 90% of breast cancers arise in the cells lining the ducts of breast tissue. Early detection of breast cancer may rely on a clinical capability to distinguish such changes as might be present in an image. Again, the presence of local or general dense breast tissue makes this a very challenging task. As a function of breast density, dense breasts can be understood to include 5% to 95% dense breast tissue. Typically, densities vary throughout the breast volume with some local regions having greater or lesser density than other (e.g., different or nearby) regions. Overall, there may be specific regions in a woman's breast is very high density and other areas of very low density containing fatty tissue. In some women, the entire breast may be extremely dense, while in others there are only spots where high density occurs. Regardless of the amount of density that is high as a percentage of a woman's breast, any cancer occurring within a high-density area is subject to being misdiagnosed because breast cancer appears white in a mammogram as does dense breast tissue often leading to a radiologist inability to discriminate between the high density and the cancer itself.

Breast cancer may develop from normal tissues in one or more different progressions of change. Abnormal tissue development may progress from being normal to Hyperplasia to Atypical Hyperplasia to ductal carcinoma in situ (DCIS) to invasive DCIS. Tissues can evolve from being normal to being an invasive carcinoma with no intervening steps. Once the tumor has grown beyond the duct, it is called an invasive carcinoma.

Currently, only 1% of breast cancers are capable of being detected when the lesion is 1 mm in size or less.

The challenges of using computer aided detection and machine-learning techniques to detect cancer in images showing local or general variation densities of tissue are compounded by the variability associated with the dynamic structure changes that can occur in living tissues. Segmentation of disease involving this number of possible combinations makes it very difficult to train computers to consistently detect cancer while maintaining a low number of false positives.

Techniques such as standard machine learning protocols, the use of segmentation algorithms, and processes for causing only pixels associated with disease to be isolated (i.e., segmented or bifurcated) in images have the issue of having too many combinations as possibilities to correctly identify the disease. These processes function best when there is a SINGLE object that has unique boundaries associated with the object of interest. For example, identifying bacteria in an image generated through a microscope is aided because bacteria have definite shapes and sizes and the cell boundaries limit other possible combinations. As the name implies, bifurcation of images results in abrupt changes that lead to binary (yes/no) results and does not allow for subtle differences at boundaries within a given domain of image content.

In contrast, breast cancer, as well as other diseases and abnormalities, has diffuse boundaries. The cancer is most often amorphous and multi-patterned. Tissues may also be in a variety of transition states. A lesion may have cells that are in the Atypical Hyperplasia state as well as being Ductal Carcinoma in Situ, and becoming invasive. Additionally, both normal and abnormal breast conditions may include or be affected by:

Presence of spiculations and calcifications
Presence of necrotic tissue
Abundance of dense fibroglandular tissue associated with embedded cancer
Prior surgeries, biopsies, or weigh gain
Changes to a woman during her menstrual cycle or from menopause.

Conventional CAD approaches

In general, radiographic findings related to breast cancer generally involve identifying the presence of two different types of structures, masses and microcalcifications. Microcalcifications related to pathology generally occur in ducts and in association with neoplasms. Masses are most often correlated with abnormalities and can either be benign or cancerous. Fibroglandular tissues within the breast can obscure masses, making detection difficult in unprocessed images.

In mammography, two mammographic views are generally created for each breast (cranial/caudal CC and medial lateral oblique MLO), to assure that all breast parenchyma are included in the views. This further complicates the task of cancer detection and quantification in that it is hard to correlate the presence and dimensionality of structures between the two different views.

Existing computerized diagnostic methodologies typically employ the following sequence of processing: suspect lesion>lesion extraction>feature extraction>classification >predict probability of malignancy>report probability.

In these methodologies, it is important to segment or extract (e.g., cause to divide) areas of concern to be able to analyze the areas for possible malignancy. For example, applying equalization or divergence processes to the image differentiate fatty tissue from dense tissue. The equalization process is limited in that it is a linear process and has no specific thresholding that is optimal for all mammograms. While divergence-type segmentation algorithms may be used in separating fatty from dense tissue, it does not effectively support differentiation of white cancer areas within white dense breast tissue.

Binary processes are typically designed to look for specific diseases, but do not address other diagnostically important features in mammographic or other medical images such as architectural distortions of the breast, degree of asymmetry between breasts, nipple retractions, dilated ducts, and skin lesions as defined by the American College of Radiology (ACR). While not being cancerous, these features are still of importance to the clinician and their patients. While segmentation and bifurcating divergence algorithmic approaches focus on cancer, they are not designed to address the overall structures of all tissues in the image.

These segmentation techniques often use analysis of gray level increments in pixels, to define the boundaries of a possible lesion. Other techniques use probabilistic interpolation of pixel data but the interpolation method is limited again by the extreme similarities between lesions and dense tissue.

Local Micro-Contrast-Based Convergence

In some embodiments of the invention, there are disclosed systems and methods associated with image processing methodologies designed to improve visualization and maintain context of all tissues by differentially and predictably visualizing and characterizing all structures and features within the context of a given image. These embodiments employ a process of iterative sequencing of image processing functions that cause the local micro-contrast patterns associated with each material type to coalesce (or converge) and consistently be expressed as distinctive characteristic patterns within the resulting processed image. In other words, these embodiments provide an approach for the characterization of all tissue types within the context of the rest of the tissues, rather than attempting to extract or remove identified tissue types outside the context of the rest of the tissues.

Many objects in the real world, such as biological growth, patterns of neurons, branching of rivers, corrosion of pipes, and formation of snowflakes, are statistically self-similar where the patterns of development show the same statistical properties at many scales of magnification. In these patterns, a small piece of the object or pattern is similar to the patterns at a larger scale. These self-similar natural patterns are expressed as discrete pixel neighborhoods captured in images. An iterative process that may be used in the local micro-contrast convergence methodology, as utilized in at least some embodiments of the invention described herein, is designed to, and functions in a way, that explicitly visualizes and characterizes these self-similar patterns at any scale in the image.

FIG. 1a shows one embodiment of the local micro-contrast convergence algorithmic sequence pathway approach. An original image 101, e.g., a grayscale image 101, is input into the Iterated Functional Module processing sequence. The image 101 is then processed by an image processing function 102 which either becomes the resultant image 103 or is further processed by applying a second, but different image processing function at function 102. The repeating process may be applied from 0 to n times.

Diseases such as cancer exhibit such self-similarity in its growth, and that growth can be characterized and visualized at any scale utilizing the local micro-contrast process where very small cancerous lesions exhibit the same expressed patterns as large lesions.

While fractal geometry can generate patterns of nature through the iteration of mathematical functions, the approach exemplified in this set of embodiments mathematically decomposes the fractal-like patterns generated in biological systems into identifiable and measurable expressions of pixel data within an image. Consequently, the local micro-contrast convergence algorithms described herein can be mathematically parallel to an iterative process, and can visualize tissue patterns such as breast boundaries, cancerous and benign lesion margins and cores, and characteristics of breast asymmetry that can be present in mammographic images.

As used herein, local micro-contrast convergence may refer to an iterative sequencing of image transformations utilizing profile look-up table (PLUT) functions.

As used herein, the PLUT functions refers to mathematical expressions in a matrix/array that specifies image input and output values of an image so that localized, self-similar image contrast pixel variables (such as statistically-based co-occurrence of pixel neighborhood relationships—textures for example) in the source image, have a discrete sets of values (called reconstruction levels) where the pixels in each local neighborhood (e.g., pixels having similar characteristics) in the source image are assigned a single color or luminance value in a resulting output image.

Singular or iterative applications of PLUT and other functions in the local micro-contrast convergence process can cause relationships among neighboring pixel groups to converge or aggregate into repeatable and predictable color and/or luminosity patterns consistent with the material's structure and relationship to its imaging modality. Although tissue/material types may vary significantly, each tissue/material type possesses common underlying pixel neighborhood relationships. The resulting local micro-contrast convergence patterns expressed in each area of the image are capable of visually expressing their characteristic color patterns based on e.g., the statistically-based distribution of luminance values for each object or material, regardless of the presence of surrounding and overlying materials of different types. For example, using a local micro-contract convergence algorithm, a breast cancer lesion in a mammogram can be characterized with a specific visually-observable and uniquely quantifiable pattern regardless if it is in dark fatty or high luminance dense breast tissue.

Figure 1B:
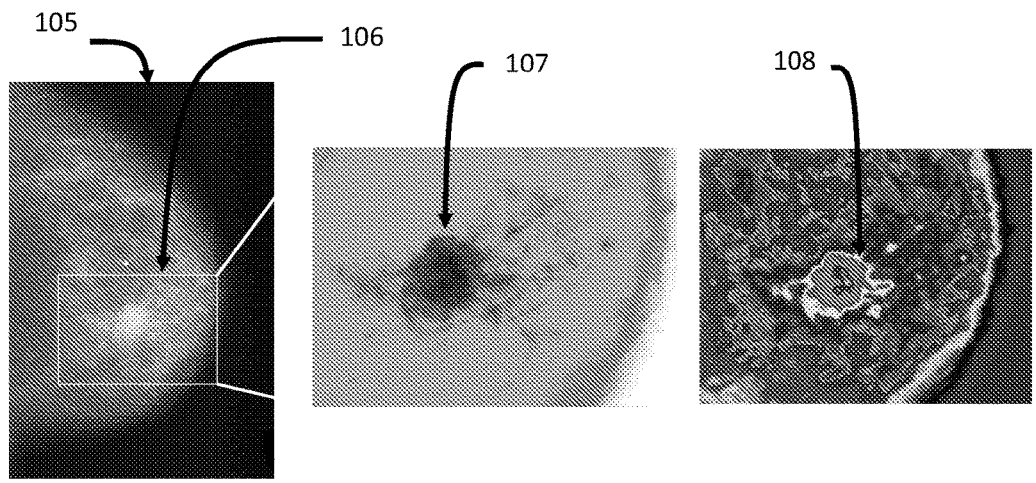
FIG. 1b depicts two resultant image representations after processing an original mammogram in accordance with an exemplary embodiment of the present invention.

FIG. 1b shows an original mammogram image 105 and two resultant images 107, 108 produced using at least some embodiments of the invention. A box outlining the area of cancer is shown at 106. Two resultant images are created by two different local micro-contrast convergence algorithmic sequences reveal distinctive patterns of the cancer as shown at 107 and 108. The iterative processing sequence transformed the subtle grayscale patterns of the original X-ray of the breast into characteristic pattern responses, such as edges, boundaries, internal structures, textures, spiculations, and luminance values and colors associated with a cancer response.

Figure 1C:
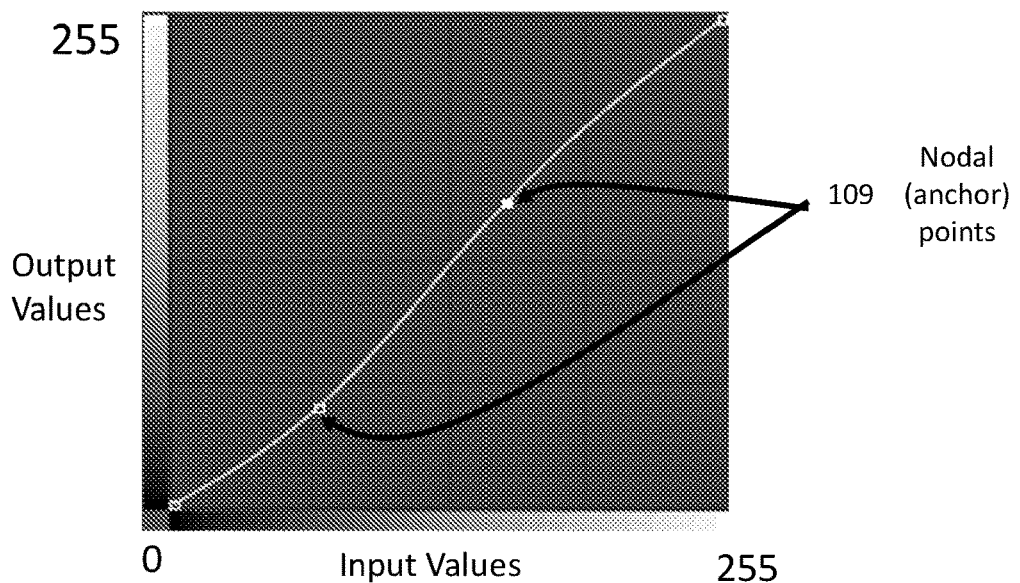
FIG. 1c is a characteristic non-linear luminance transform "tone adjustment curve" with 2 nodal (anchor) points, in accordance with an exemplary embodiment of the present invention.

FIG. 1c illustrates a standard photographic coordinate system used to plot an image transformation using 2 nodal points at 109. As used herein, a nodal point refers to a singular point on a curve where the direction of the curve is altered. Moving any nodal point on a curve alters surrounding aspects of the curve. The input values of the original image are indicated along the bottom of the plot (x axis) and the output of the image values are indicated on the vertical axis. There are limitations with this approach. Nodal points change the shape of the "curve" and modify the relationship between the input values and the output values of an image. However, nodal points must be linked so that all parts of the curve are continuous. Therefore, it is limited to what can be mapped with continuous and linked values. Non-linear transformations utilizing nodal points perform poorly when separation of objects of nearly equal densities is desired.

Currently, feature extraction is completely dependent on the degree to which objects have successfully been segmented or extracted from the image's pixel data. While existing algorithms are optimally designed to locate the brightest area of a possible lesion, they often fail to distinguish the external boundaries of the lesion, an area important in diagnosis to determine where angiogenesis is occurring.

In this application, the one or more local micro-contrast convergence functions are without nodal points so that an image can be processed to properly define possible external boundaries of a legion (or other feature of interest).

Figure 1D:
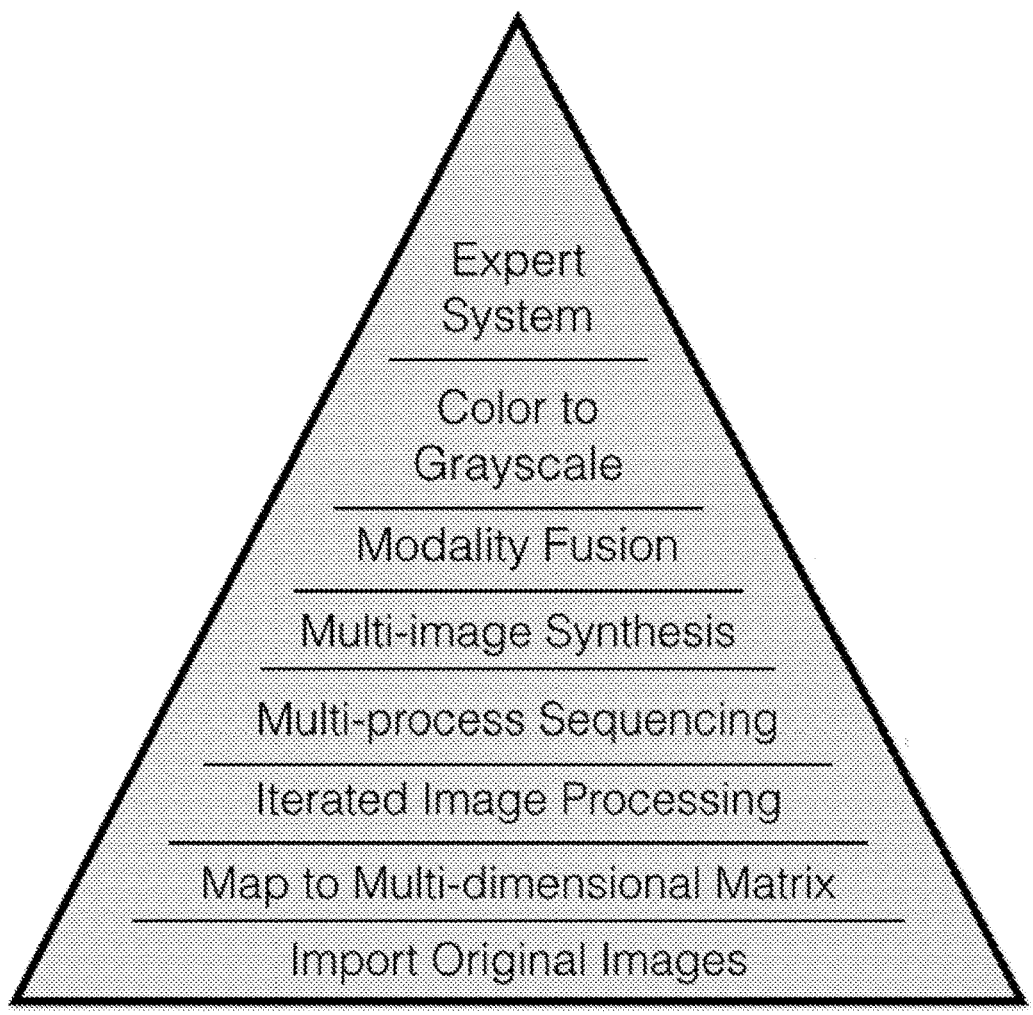
FIG. 1d is a hierarchical structure of the levels of image processing and analysis embodied, in accordance with an exemplary embodiment of the present invention.

FIG. 1d diagrams the hierarchical approach to the implementation of the local micro-contrast convergence process. The sequence progresses from the bottom of the triangle to the top as it relates to higher levels of processing integration.

Multi image Modality Fusion is supported in the local micro-contrast convergence process. Modality Fusion, as it relates to the embodiment of this application, is a process of adapting the input values of images from different types of imaging modalities, so that the same, or slightly modified local micro-contrast convergence algorithmic sequences, can visualize and characterize, the same types of tissues between different imaging modalities. A local micro-contrast convergence pattern would then be similar for a patient's cancer when viewed in an X-ray, ultra-sound, breast CT, and MM scan. This allows for combining information from different input modalities in a principled way. The imaging-based fusion approach facilitates early fusion, in which signals are integrated at the image feature level, and late fusion, in which information is integrated at the semantic level using post-processing image feature analytic tools.

These data can be used to generate one or more probability distribution functions correlated to localized response patterns at one or more vector coordinates to characterize materials such as normal, benign, and cancerous breast-tissue-types and correlate that data from a multiplicity of X-ray, MM, or ultrasound images, even when the tissues/materials are overlaid with other tissue/material types.

In some embodiments, the Multi-processing Sequencing, Multi-image Synthesis, and Modality Fusion, the resultant images can be analyzed, and data correlated among those images within an Expert System. Since all tissues are visualized in the local micro-contrast convergence process, diseases can both be detected, and their pathology correlated to their occurrence within the organ of origin. This provides opportunities for advanced research in disease prevention and drug/treatment therapies.

At least some embodiments of the invention described herein are capable of consistently characterizing tissue/material types in images where other mathematical models, built on purely deterministic, or deterministic with simple random components fail, due to the complex stochastic non-Euclidean fractal-like shapes involving patterns of growth/development represented in images of natural processes like those in medicine.

In some embodiments, the methods are designed specifically to be able to identify structures within structures. For example, in medical imaging applications, the finalized images provide visual evidence as to the presence and structure of abnormal tissues in the context of the remaining structure in the image. The finalized images may also provide a mechanism to correlate abnormal objects to other normal and abnormal tissue types. For example, a cancerous lesion that is in a milk duct has a different level of concern than a lesion that has become invasive or appears to be associated with a lymph node. Similarly, a carcinoma in proximity to microcalcifications requires a different clinical interpretation as compared to a carcinoma next to the chest wall or in situations where there is significant asymmetry in the breast.

Figure 1E:
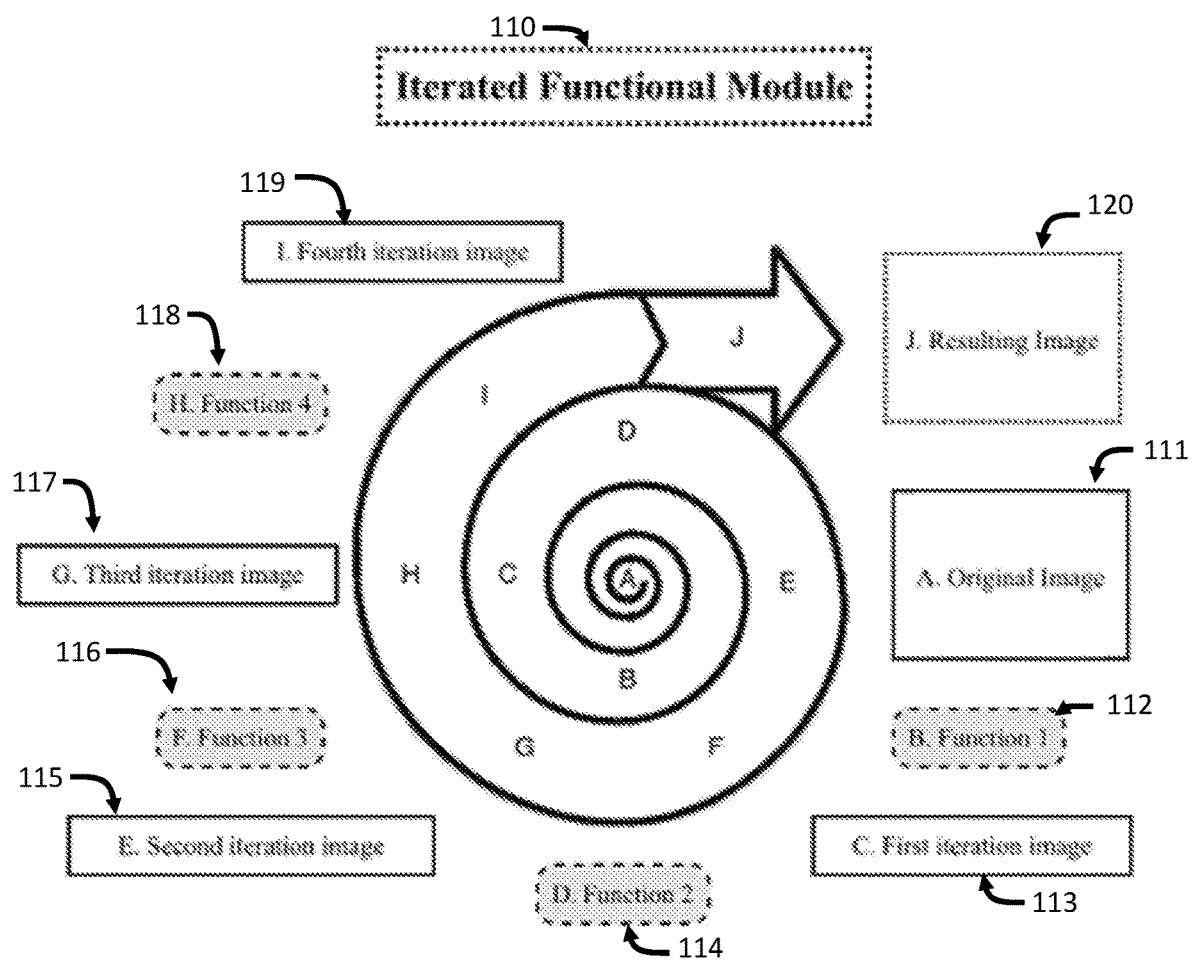
FIG. 1e is a local micro-contrast convergence algorithm sequence, in accordance with an exemplary embodiment of the present invention.

An example of an iterative image process is illustrated in FIG. 1e. Specifically, FIG. 1e illustrates an exemplary fundamental sequencing of the local micro-contrast convergence process whereby an Iterated Function Module 110 approach takes a first image 111 and processes it with a first set of one or more non-linear transfer functions 112 (e.g., local micro-contrast convergence algorithm). The second image created either becomes the final resultant image 120 or, if a next processing step is designed as part of the algorithm, the first iteration image 113 is further processed with a second function 114 (e.g., a second set of one or more non-linear transfer functions) resulting in image 115. The process can be iterated one or more times with different sets of non-linear transfer functions (e.g., a third set of one or more non-linear transfer functions or a fourth set of one or more non-linear transfer functions) applied within a given algorithmic sequence 116 to 119 to output a resultant image 120.

In some embodiments, using a same source image 111, a second Iterated Functional Module can be applied to the same image 111, but applying different functions and number of iterations to reveal different characterizations and relationships among the tissues. Consequently, this Multi-process Sequencing approach can provide two distinct characterizations of the same objects within the same original image.

In some embodiments, two or more of the resultant images can be combined or merged in a Multi-image Synthesis process to create a new resultant image that is a composite of the two resultant images or a composite of one resultant image and the original image. This composite image can be further processed or combined with other resultant images.

Figure 1F:
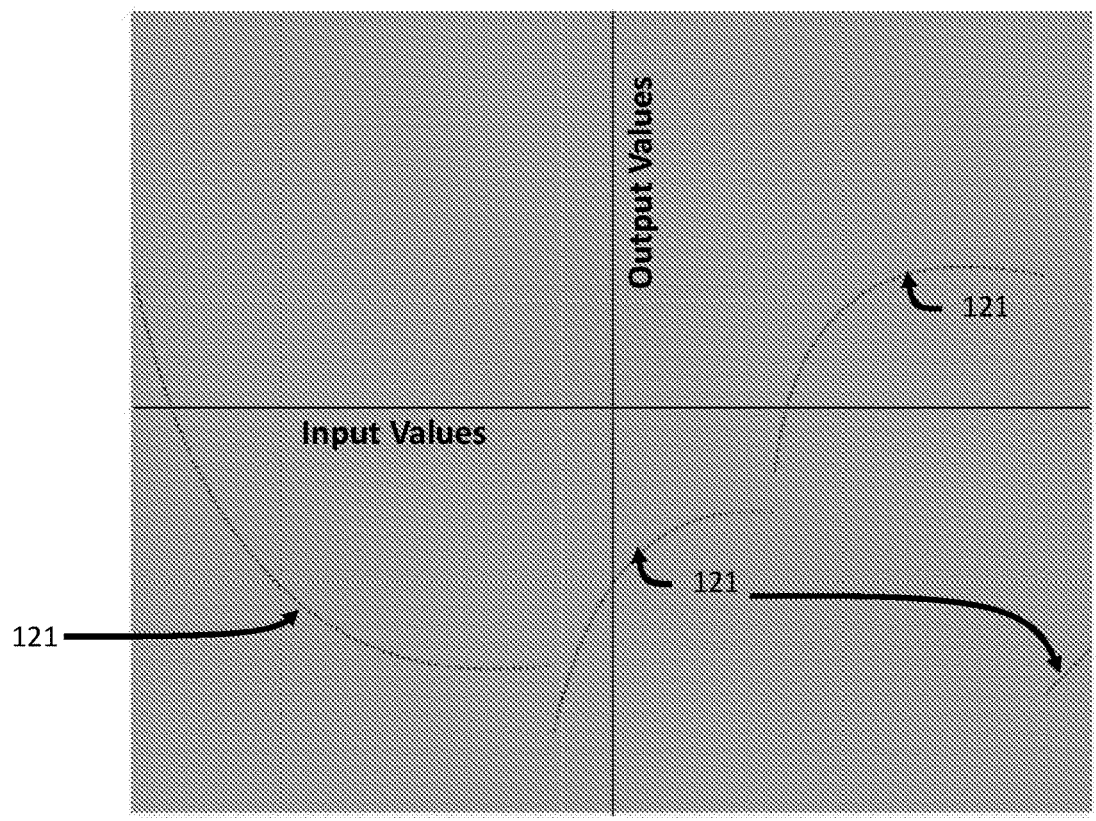
FIG. 1f is a plot in a coordinate system representative of a non-linear transfer function, in accordance with an exemplary embodiment of the present invention.

FIG. 1f shows a plot in a coordinate system illustrating a discontinuous non-linear transfer function according to at least one embodiment of the invention. FIG. 1f illustrates one example of mapping input values of a input image along the x-axis and output values of an output image along the y-axis. The graphic plot generated from a PLUT illustrates the potential to design discontinuous transformations to apply to images. By using PLUTs with discontinuities in the design of the local micro-contrast convergence algorithms, at least some embodiments of the Iterative Transformation Module process can better differentiate margins of cancers from surrounding tissues, even when the cancers are embedded in dense breast tissue. This is a capability that is very limited with the use of nodal point plotting, or may not be possible at all, when transforming input to output values in images.

Figure 1G:
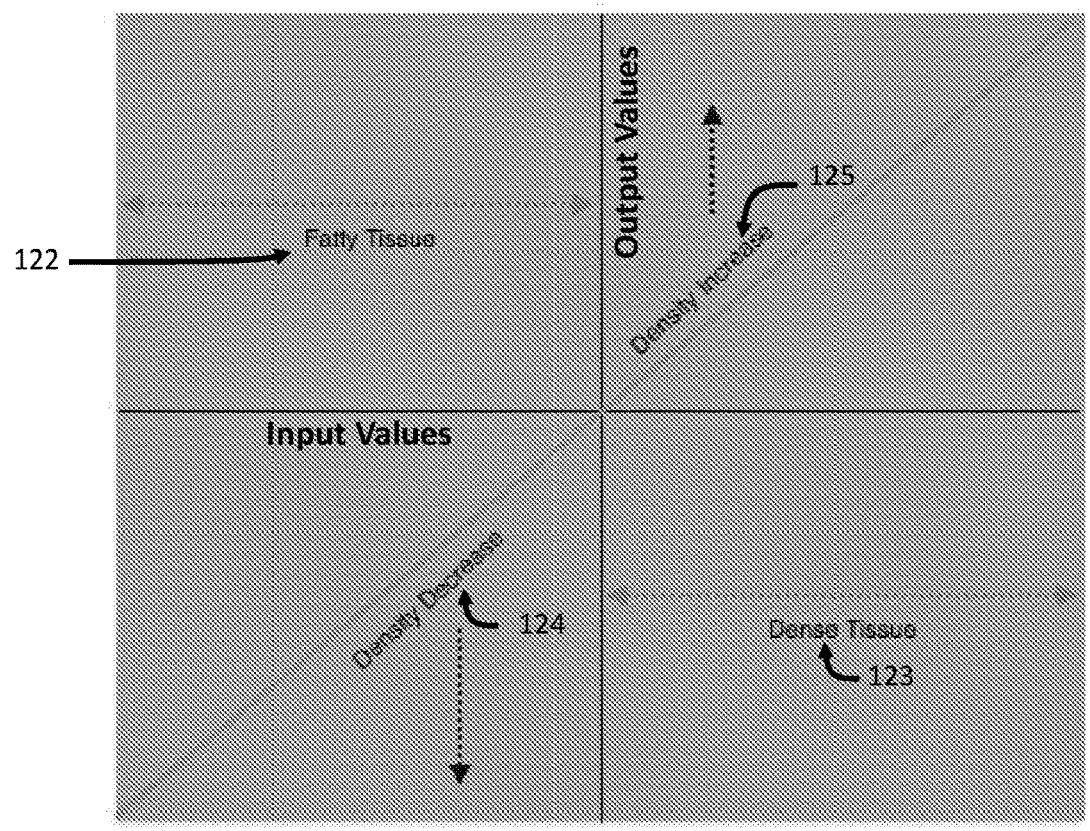
FIG. 1g is a plot in a coordinate system representative of breast tissue color in a grayscale image in accordance with an exemplary embodiment of the present invention.

FIG. 1g shows a plot in a coordinate system illustrating luminance values of breast tissue in a mammogram image. FIG. 1g illustrates one example of mapping input values along the x-axis and output values along the y-axis. Fatty tissue representation 122 is indicated in the luminance area of breast images that contain fatty tissue and dense tissue representation 123 indicates the luminance area of breast images that contain dense tissues. Typically, breast cancer has luminosities much higher than those of fatty tissue. Consequently, it is important to separate fatty tissue from dense tissue. Any remapping of luminosities below the red diagonal line makes that part of an image darker decreasing the density 124, while those above the line makes the values brighter and increases the density 125. The correlation of this image property distribution with discontinuous nonlinear transformations built into the PLUT design reduces time needed for developing new algorithms for new diseases and imaging modalities.

Figure 2A:
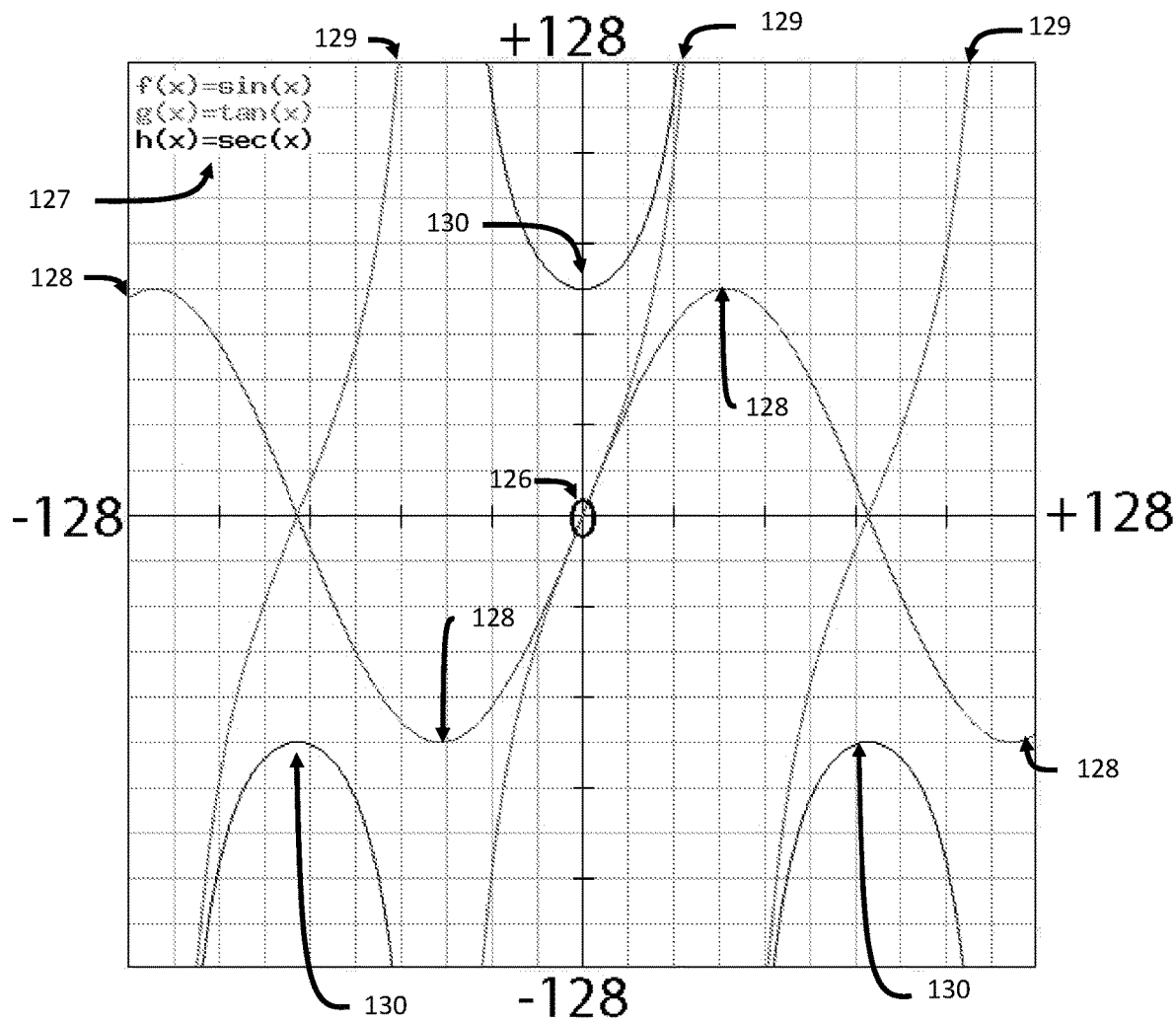
FIG. 2a is a mathematical function that may be used to generate a new profile look up table (PLUT) input and output values in accordance with an exemplary embodiment of the present invention.

FIG. 2a illustrates one embodiment where multiple mathematical functions can be utilized to create possible PLUT values for multiple image channels to create different iterations of a local micro-contrast convergence algorithm for use in applications with new diseases, modalities, and applications beyond medicine. Utilizing computer-based creation of PLUT sequences can greatly speed the process of developing new algorithmic sequences for visualizing new diseases or anomalies.

In FIG. 2a, the x and y axis reflect the input and output values of an image while mid-point 126 specifies one possible position of a mid-point for the coordinate system. FIG. 2a expresses the luminance and color values of an 8-bit image with 256 data points possible for luminance and multiple color channel mapping. Three mathematical functions 127 were plotted automatically and their values indicated within the plot. The blue curve (blue channel) 128 was created using $f(x)=\sin(x)$. The red channel 129 was created using $g(x)=\tan(x)$ and the luminance channel 130 was created using $h(x)=\sec(x)$. The mid-point 126 (or 0 point) can be placed in any position within the coordinate system that best supports the mapping of mathematical functions that can be mapped to a PLUT for optimization of tissue/material visualization and characterization in an automatic, rather than a laborious manual process.

Figure 2B:
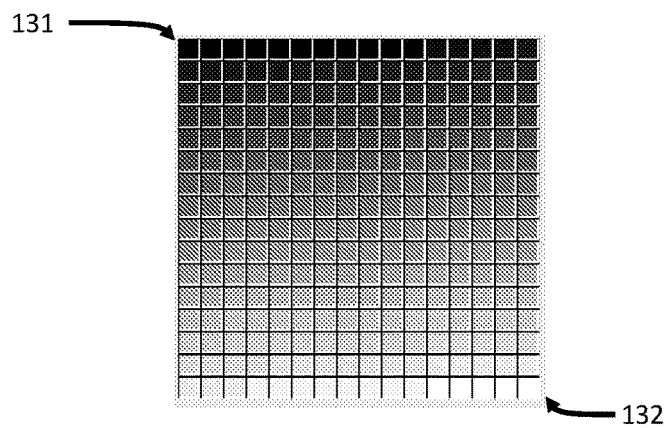
FIG. 2b is a look-up table (LUT) for an 8-bit grayscale image according to at least some embodiments of the invention.

FIG. 2b shows a matrix representing a grayscale 2D look-up table for an 8-bit grayscale image. Level 0 representing black is in the upper left corner of the grid at 131. Grayscale luminance levels increase stepwise left to right, and top to bottom until pure white level 255 is reached in the lower right-hand corner at 132.

Exemplary Computer System

Figure 2C:
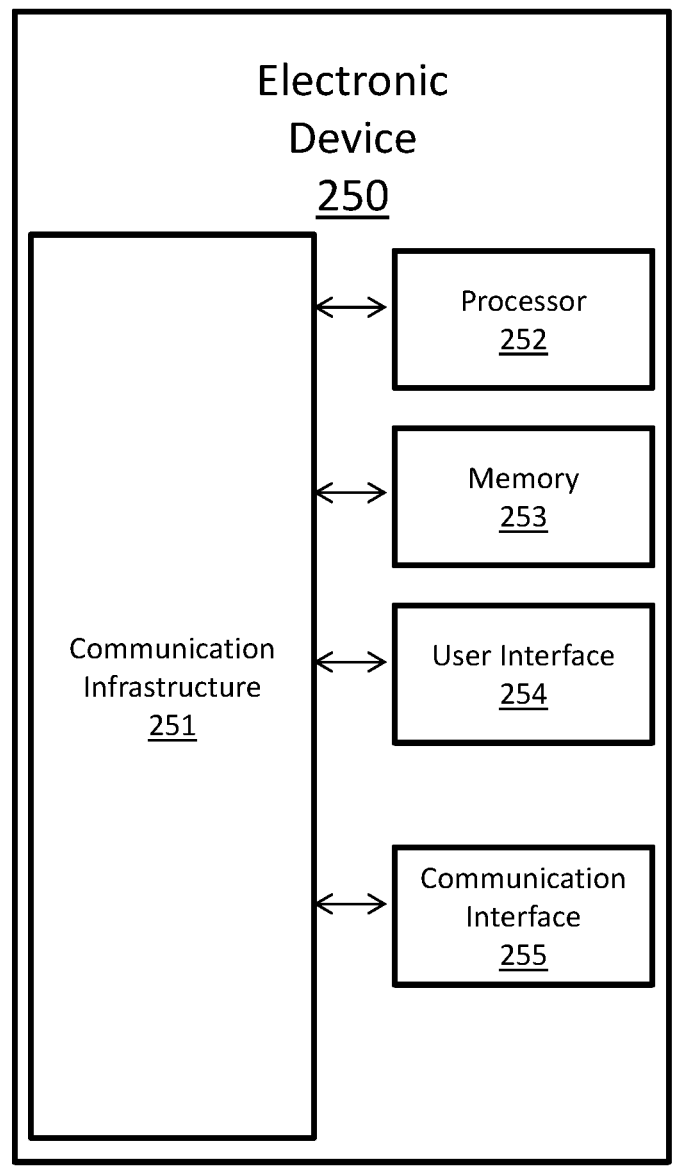
FIG. 2c is a block diagram that illustrates an electronic device for performing one or more methods according to at least some embodiments of the invention.

FIG. 2c shows a block diagram that illustrates an electronic device 250 for performing one or more methods according to one or more embodiments of the present invention.

Electronic device 250 may be any computing device for receiving data from a user or a remote device, processing data, and generating and/or displaying data. Electronic device 250 may include communication infrastructure 251, processor 252, memory 253, user interface 254 and communication interface 255.

Processor 252 may be any type of processor, including but not limited to a special purpose or a general-purpose digital signal processor. In this embodiment, processor 252 is connected to a communication infrastructure 251 (for example, a bus or network). Various software implementations are described in terms of this exemplary computer system.

Memory 253 may include at least one of: random access memory (RAM), a hard disk drive and a removable storage drive, such as a floppy disk drive, a magnetic tape drive, or an optical disk drive, etc. The removable storage drive reads from and/or writes to a removable storage unit. The removable storage unit can be a floppy disk, a magnetic tape, an optical disk, etc., which is read by and written to a removable storage drive. Memory 253 may include a computer usable storage medium having stored therein computer software programs and/or data to perform any of the computing functions of electronic device 250. Computer software programs (also called computer control logic), when executed, enable electronic device 250 to implement embodiments of the present invention as discussed herein. Accordingly, such computer software programs represent controllers of electronic device 250. Memory 253 may include one or more data stores that store imaging data, software files or any other types of data files.

User interface 254 may be a program that controls a display (not shown) of electronic device 250. User interface 254 may include one or more peripheral user interface components, such as a keyboard or a mouse. The user may use the peripheral user interface components to interact with electronic device 250. User interface 254 may receive user inputs, such as mouse inputs or keyboard inputs from the mouse or keyboard user interface components. User interface 254 may display imaging data on the display of electronic device 250.

Communication interface 255 allows imaging data to be transferred between electronic device 250 and remote devices. Examples of communication interface 255 may include a modem, a network interface (such as an Ethernet card), a communication port, a Personal Computer Memory Card International Association (PCMCIA) slot and card, etc. Imaging data transferred via communication interface 251 are in the form of signals, which may be electronic, electromagnetic, optical, or other signals capable of being transmitted or received by communication interface. These signals are provided to or received from communication interface 251.

Exemplary Local Micro-Contrast Algorithms

Figure 3A:
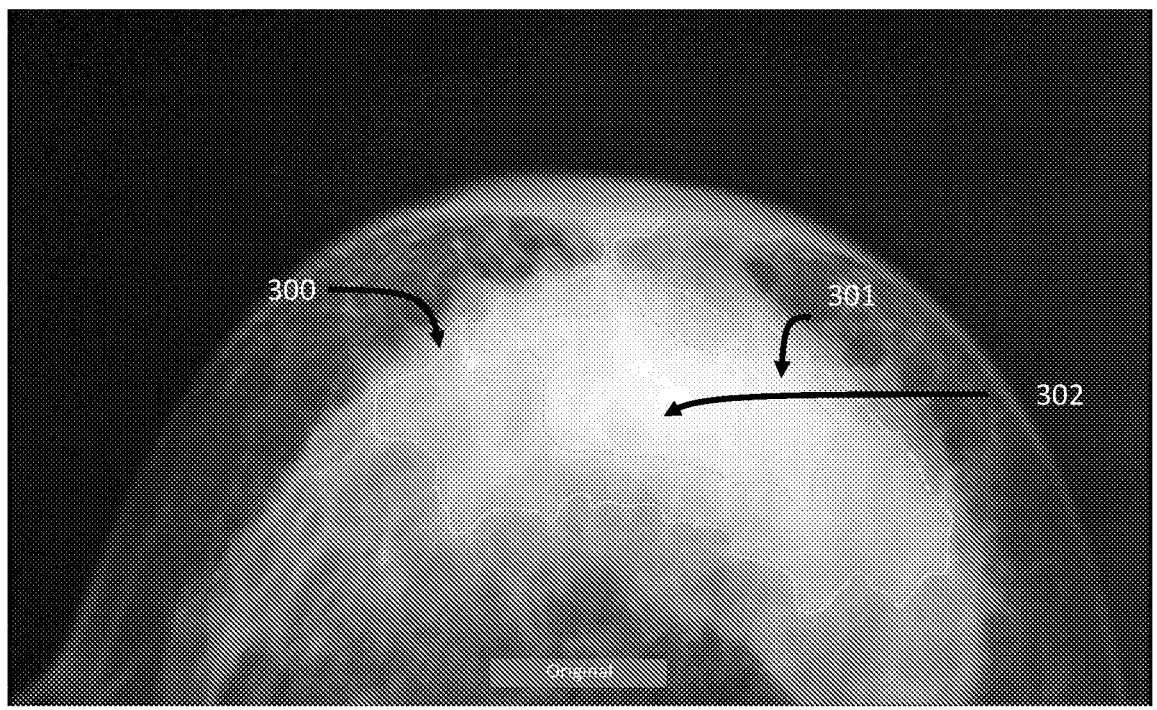
FIG. 3a is an exemplary high density (as defined by the American College of Radiology (ACR) density classification system) original X-ray mammogram containing cancer in the brightest area of the image.

FIG. 3a shows a mammogram containing very dense breast (as defined by the American College of Radiology (ACR) density classification system) with high density outlined at 300. The outline at 301 defines the boundary of extreme density containing cancer at 302.

Figure 3B:
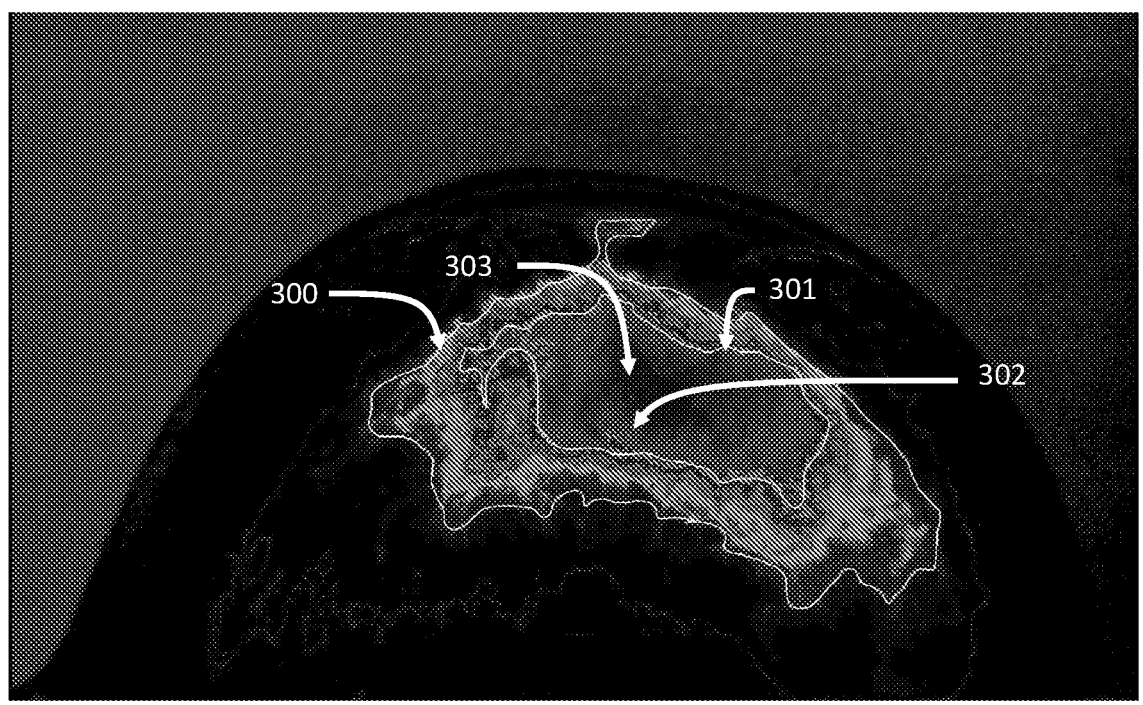
FIG. 3b is an exemplary mammogram image after applying local micro-contrast convergence algorithm sequence to create the resultant image using one or more methods in accordance with an exemplary embodiment of the present invention.

FIG. 3b shows an exemplary mammogram image after processing the image using one or more methods described herein. In this embodiment, only the highest density areas of the breast are revealed in color. Fatty and other low-density areas of the breast image are indicated in black at 303. Density increases are indicated in steps proceeding from the outer boundary in green 300 and progressing inward to the blue 302 and finally black area in the center 303 where the greatest development of the cancer exists. Each color represents a quantifiably different level of breast density. This quantification provides precise reporting for the American College of Radiology BI-RADS (Breast Imaging Reporting and Data System) specification to indicate the presence of dense breasts in a woman's mammograms. Additionally, however, this process can extend the BI-RADS reporting system to go beyond a simple overall percentage of the breast density. It can quantify multiple levels of breast density, specify their distribution, and estimate possible risk for the woman. These methods are adaptive and compensate for the extreme variability in mammographic image presentations influenced by differences in the size of the breast, the density of the breast, changes during pregnancy, changes with aging and menopause, alterations based on the development of cysts, fibro adenomas, calcifications, the presence of lesions, and scarring due to trauma, surgeries, and biopsies.

CI Algorithm

Embodiments of the CI algorithm are designed to optimize the expression of high-density abnormalities in breast tissues by processing original grayscale mammograms and revealing the abnormality's boundaries and internal structures. The algorithmic sequence provides significant color and brightness differentiation between the abnormalities and other normal tissues such that it is easier for clinicians and patients to readily observe areas of concern.

Figure 4K:
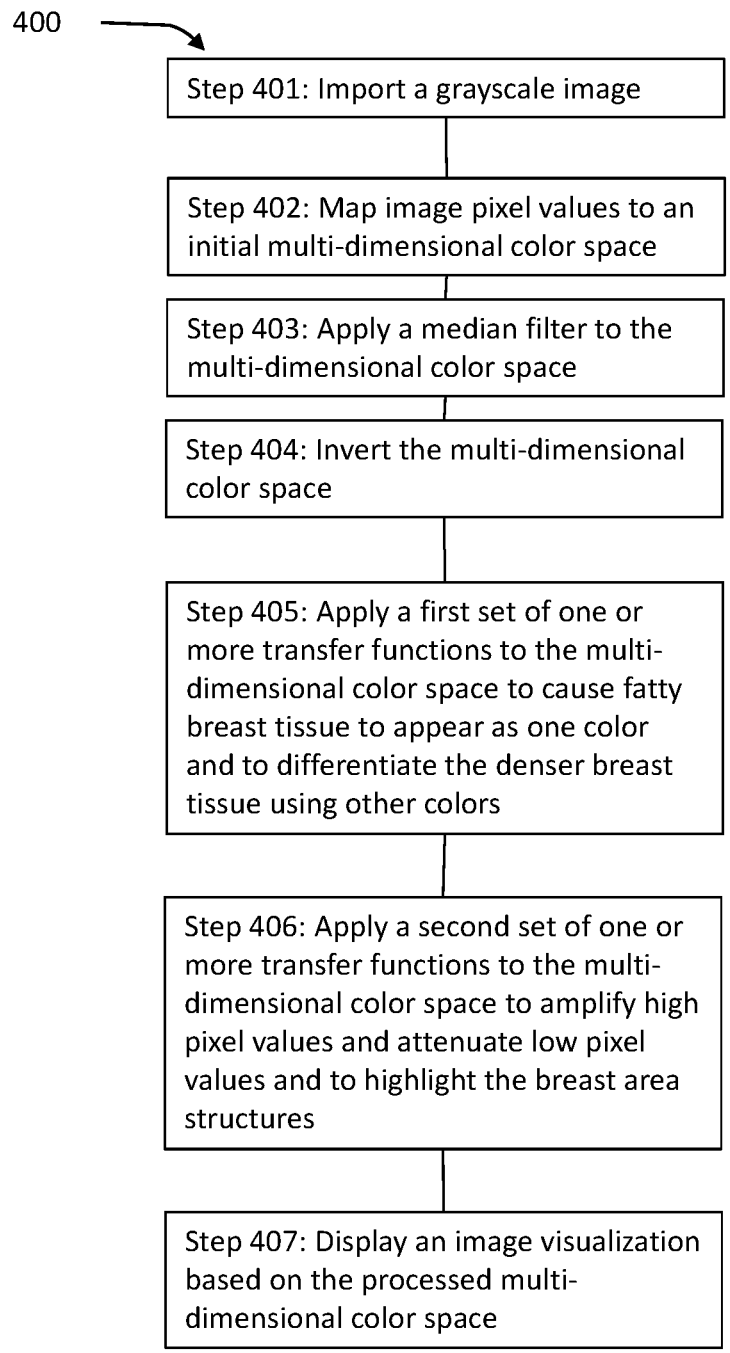

FIG. 4k is a flow chart illustrating a method 400 for creating a visualization from a grayscale image, according to at least one embodiment of the invention.

At step 401, processor 252 imports a grayscale image. FIG. 4a shows an exemplary grayscale image of a mammogram, according to at least one embodiment of the invention. FIG. 4d shows a horizontal gradient representation of FIG. 4a. The gradient grayscale image provides the full range of luminance levels, as compared with the range different mammograms have, so that the full range of colors expressed in the local micro-contrast convergence algorithmic sequence can be illustrated. Each step of the algorithmic sequence described in FIG. 4k can applied to both the mammograms and the gradients, again, for illustration and comparative purposes.

In some embodiments, a processor 252 receives or imports an image (e.g., grayscale). In some embodiments, the image is imported from memory 253. In other embodiments, the image is imported from a remote device via communication interface 251.

In some embodiments, the grayscale image is imported for processing as an input array or matrix with x and y pixel dimensions and z bits of grayscale or color depth. In some embodiments, the matrix may contain values of 8, 10, 12, 14 or 16 bits of luminance per pixel (Lp). (Lp) is the luminance value of each pixel (p) at a position (x, y) in the original image. As the number of bits increase, the greater number of variations in a pixel value also increases. For example, if 8 bits are used, then $2^8$ possible pixel values may be assigned to each pixel. On the other hand, if 16 bits are used, then $2^{16}$ possible pixel values may be assigned to each pixel. By increasing the number of possible pixel values, the image processing methods described herein can increase the variations in the final image.

At step 402, processor 252 maps the grayscale image to a multi-dimensional color space.

In some embodiments, to map the grayscale image, the grayscale image is replicated into additional matrices of identical x/y coordinates for each color component and luminance value to form an n-dimensional super-positioned matrix space of color space layers, where n>1 forms a new matrix set containing voxels.

In some embodiments, the grayscale image is replicated using the following equation:

$$f(Lp){=}Cp,$$

where the pixel values at each x/y coordinate in the original is mapped to corresponding x/y coordinate in each color space layer of the multi-dimensional color space of C.

In one embodiment where n=4, an RGB multi-dimensional color space can be defined in terms of four different components: luminance, red, green, and blue. In these embodiments, the RGB multi-dimensional color space includes a luminance color space layer, and first, second and third color space layers corresponding to blue, red and green, respectively. The new matrix C will contain pixel values where R=G=B=Luminance for each pixel value and these pixel values are equal to the grayscale image luminance values (Lp). In some embodiments, there can be a separate luminance only channel or, in other embodiments, the luminance can be generated as a composite of the three other channels. In another embodiment, the values can also be expressed for other values of n where, for example, n has 3 values luminance, saturation, and hue.

One of ordinary skill in the art will appreciate that these embodiments are operable on matrices of n-dimensions that can be visualized in a wide range of color image formats other than the color image formats described herein. The processing of each mammogram (or other image) begins with a multi-channel matrix or image. Additional color spaces may also occur in color spaces such as HSV, CMYK, CIEXYZ or CIELAB using either xyz or cylindrical color spaces.

At step 403, processor 252 applies a median filter to the multi-dimensional color space. In some embodiments, a median filter may refer to a nonlinear digital image processing technique, which preserves edges of objects in the multi-dimensional color space while removing noise. Noise reduction can improve the results of later processing.

In some embodiments, the median filter is applied to each pixel in the multi-dimensional color space by replacing each pixel value with the median of neighboring pixel values. The pattern of neighbors may be referred to as the "window", which slides, pixel by pixel, over the entire image. In some embodiments, the median filter is a 3×3 or radius=1 median filter. In other embodiments, a radius greater than 1 and matrix combinations such as 5×5, 7×7 can be used.

At step 404, processor 252 inverts the image whereby black (0) becomes white (255) and white becomes black. All other values are proportionally inverted except the midpoint of the image values.

At step 405, processor 252 applies a first set of one or more (e.g., PLUT) non-linear transfer functions to the multi-dimensional color space (e.g., RGB). Representations of the resultant images are shown in FIGS. 4b and 4e.

FIG. 4g shows the color values of the CI PLUT 1 (2D look-up tables) that have been optimized to reveal breast structures in this local micro-contrast convergence algorithmic sequence after being applied to the image in FIG. 4a.

FIG. 4i shows a Cartesian plot illustrating a representation of an exemplary (e.g., PLUT) transfer function applied by the processor 252 to the multi-dimensional color space to attenuate low-density breast tissue according to at least one embodiment of the invention. In this Cartesian plot, the color space layer input is shown on the x-axis, with values ranging from −128 to +128. The corresponding output after the (e.g., PLUT) transfer function is shown on the y-axis, where the midpoint of the luminance levels of an image are at 0 and the values range from −128 to +128. It can be observed that the 0 position in the coordinate plot may be placed at any position in the x/y coordinate space.

In FIG. 4i, the red channel is shown at 408, the green channel is 409, and the luminance channel is 410. In some embodiments, a first (e.g., PLUT) transfer function (as shown in FIG. 4i) is applied to the luminance color space layer to attenuate low-density fatty breast tissue. In some embodiments, the low-density fatty breast tissue has a luminance value in the lower 50% range; the lower 40% range; the lower 30% range; the lower 20% range; or the lower 10% range. In some embodiments, step 405 can cause low-density materials to appear as one color and to differentiate the denser materials using other colors.

At this stage in processing, areas that do not hold a possibility of having cancer have been separated from those where possible cancer or other abnormalities can occur. Additionally, any lesions in the image now begin to form boundaries and express internal morphological structures as micro-contrast neighborhoods converge. Compared with the diffuse grayscale mammographic image, visually distinguishable boundaries have been formed based on tissue structures. An issue associated with a phenomenon known as center-surround effect, and limits human visual perception has been minimized or eliminated. Gray values are differentially interpreted by the human vision system based on what is around the object. The same object may look brighter against a dark background and darker against a light background. At least some embodiments of the invention may allow PLUT values to be determined that eliminate the center surround issue affecting perception and detection of cancer in mammograms; based on optimal settings for human vision differentiation based on color perception theory, the image that the clinician is seeing after the transformation provides greatly enhanced diagnosis potential for the tissues being examined.

Turning back to FIG. 4k, at step 406, processor 252 applies a second set of one or more transfer functions to the multi-dimensional color space.

FIG. 4h shows the color values of the CI PLUT 2 (2D look-up table) that has been optimized to reveal breast structures in this local micro-contrast convergence algorithmic sequence after being applied to the image in FIG. 4b.

FIG. 4i shows a Cartesian plot illustrating a representation of an exemplary (e.g., PLUT) set of transfer functions applied by the processor 252 to the multi-dimensional color space. In FIG. 4i, the red channel is indicated at 411 and luminance channel at 412 are graphic representations of CI PLUT 2 lookup table in FIG. 4h.

In this Cartesian plot FIG. 4i, the color space layer input is shown on the x-axis, with values ranging from −128 to +128. The corresponding output after the transfer function (shown visually in FIG. 4i) is shown on the y-axis, where the midpoint of the luminance levels of an image are at 0 and the values range from −128 to +128. In these embodiments, the values are applied to the resultant image in FIG. 4b to cause fatty breast tissue to appear as one color in FIG. 4c (e.g., blue and magenta) and to differentiate the denser breast tissue (gold and red), and breast boundary (green) using other colors.

FIGS. 4c and 4f show exemplary image representations of a mammogram and gradient image based on the multi-dimensional color space after applying an exemplary second set of one or more non-linear transfer functions to cause low density breast tissue to appear as one color and differentiate high density breast tissue, according to at least one embodiment of the invention. In FIG. 4c, the cancer is revealed in gold 413 and surrounded by black.

The values of the high-density areas of a breast image measured in RGB values in FIG. 4c at 413 are Red>250/Green>165/Blue<50.

In some embodiments, the design concept of these transfer functions is employed to attenuate pixel values in areas of a mammogram outside of the breast tissue. As a result, one component of the transfer function values in the PLUT reduce eyestrain on clinicians in the final image by assigning a value to the areas of the mammogram outside of the breast so as not to interfere with patterns inside the breast area. In some embodiments, step 406 can amplify high pixel values and attenuate low pixel values to highlight industrial or veterinarian material structures of an object and to differentiate other materials using other colors.

At step 407, processor 252 displays a visualization image (e.g., FIG. 4c) based on the processed multi-dimensional color space.

Each step of this process further transforms a grayscale mammogram (and it also works for MRI and ultrasound images of the breast) into color patterns that clearly defined boundaries of abnormal tissues as well as reveal structures of normal breast tissue, regardless of size. In this image visualization, cancerous lesions have distinctive patterns that separate themselves from all other abnormal and normal tissue structures.

In the CI visualizations, differences in the characterization of both cancer and benign lesions in the visualizations can be differentiated using histogram analysis. The boundaries of cancer are clearly defined in the CI visualizations. In addition, differences in structure inside the boundaries of the cancer are indicated with characteristic colors and shapes. This makes it easier for radiologists to identify boundaries of cancerous and benign structures. For example, in the CI visualizations, the greater the number of color changes within the boundaries of the cancer, the more advanced the development of the cancerous tissue. Changes in tissue surrounding cancerous and benign lesions are also revealed in the CI visualizations. It is possible that the CI visualizations may also reveal angiogenesis occurring at the boundaries of cancerous lesions.

In addition to the differentiations described above, in the CI visualizations, radial scars vs. cancerous lesions and cancerous lesions vs. fibro adenomas are differentiated. The CI visualizations also indicate the presence of developing cancer within milk ducts before it has become invasive and surrounding breast tissue. Cancerous tissues can be correlated with the presence of microcalcifications.

Cancerous lesions, as well as all other structures, can be correlated between different views of mammograms for a woman such as Cranial-Caudal (CC or view from above) and Mediolateral-oblique (MLO or angled view) and be used to correlate data between studies at different times. The internal structure characterized for cancer by these methods is so precise that it can be used to guide surgeons performing biopsies, lumpectomies, and for determining progress for a patient undergoing treatment for cancer.

LD Algorithm

Embodiments of the invention regarding the LD algorithm provide visualizations that are designed to emphasize extremely fine structures and details in an image (e.g., original mammogram) that occur in the very low-density areas of the image. Diagnostically important structures such as spiculations and low attenuating lesions become clearly defined.

Figure 5A:
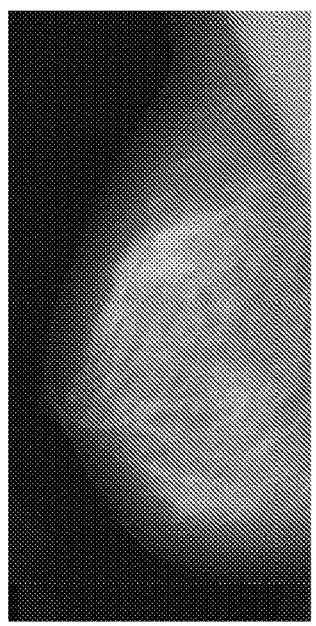
FIGS. 5a to 5i is an exemplary local micro-contrast convergence algorithmic sequence to process mammographic images to reveal low attenuating breast tissues in resultant grayscale images, in accordance with an exemplary embodiment of the present invention.
Figure 5B:
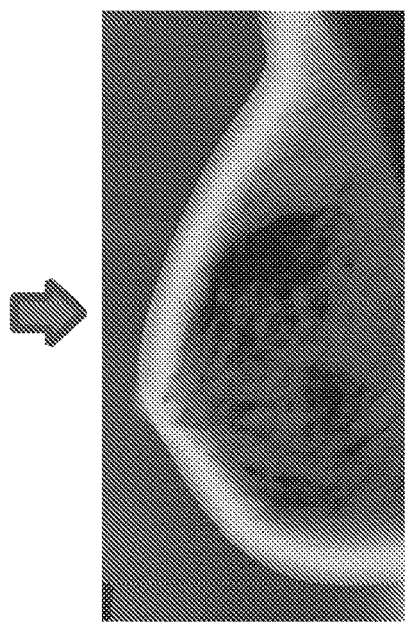
Figure 5C:
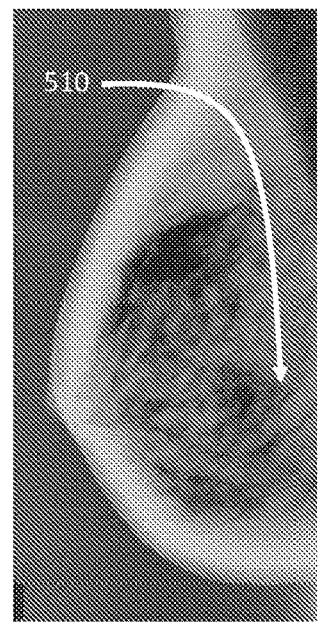
Figure 5D:
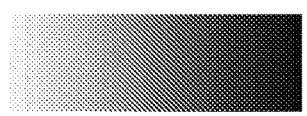
Figure 5E:
Figure 5F:
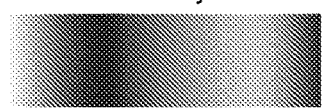
Figure 5G:
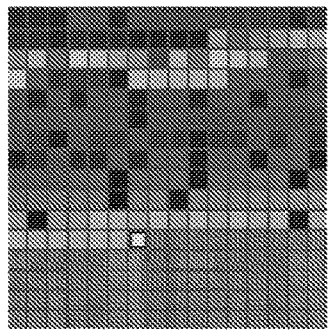
Figure 5H:
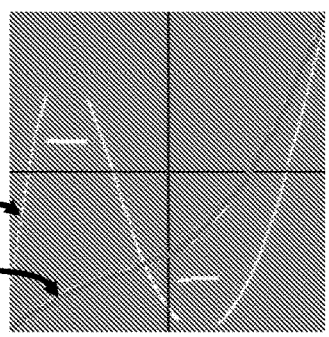
Figure 5I:
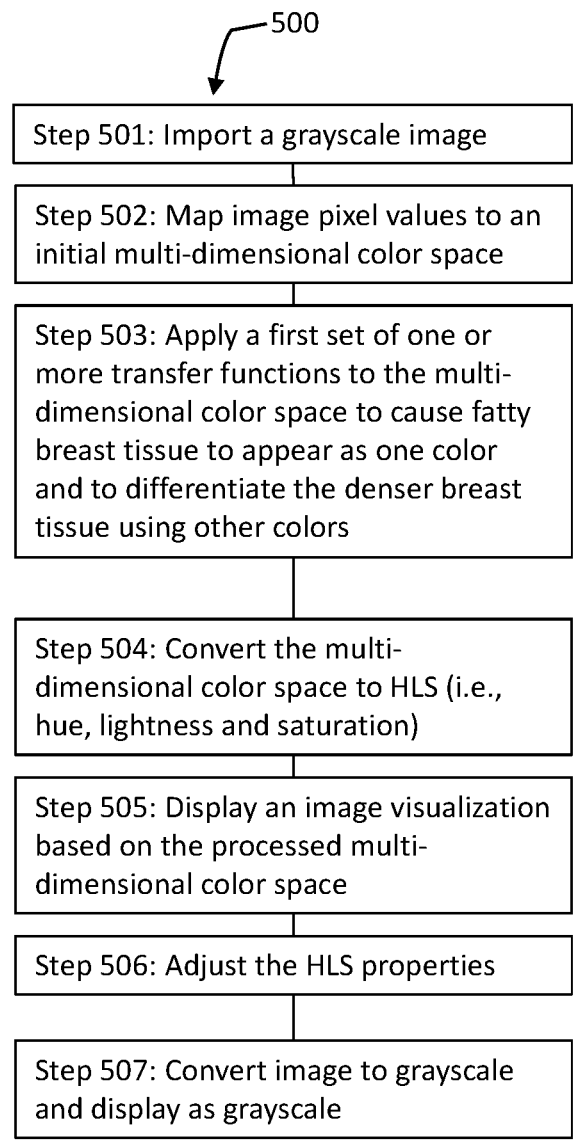

FIG. 5i is a flow chart illustrating a method 500 for creating a LD visualization from a grayscale image, according to at least one embodiment of the invention.

At step 501, processor 252 imports a grayscale image. FIG. 5a shows an exemplary grayscale image of a mammogram, according to at least one embodiment of the invention.

FIG. 5d shows a horizontal gradient representation of 256 grayscale values from black to white.

At step 502, processor 252 maps the grayscale image to a multi-dimensional color space. The grayscale mapping at step 502 is substantially similar to the grayscale mapping in step 402 above.

At step 503, processor 252 applies a first set of one or more transfer functions (e.g., a local micro-contrast convergence algorithm PLUT) to the multi-dimensional color space. Examples of the one or more transfer functions are illustrated in FIGS. 5g and 5h.

FIG. 5h shows a Cartesian plot illustrating a representation of an exemplary (e.g., PLUT) transfer function applied by the processor 252 according to at least one embodiment of the invention. In some embodiments, a first transfer function is applied to the luminance color space layer 508 to amplify pixel values representative of low-density areas of the breast image while attenuating pixel values representative of high-density breast areas. A second transfer function representing a red channel 509, colorizes the breast parenchyma while leaving the dense tissue dark. In some embodiments, the low-density fatty breast tissue has a luminance value in the lower 50% range; the lower 40% range; the lower 30% range; the lower 20% range; or the lower 10% range. The design of this local micro-contrast convergence algorithm, and its related PLUT values, function to reveal details in any portion of the image regardless of the percentage of low density in the breast. In some embodiments, step 503 can amplify pixel values representative of low-density areas of industrial or veterinarian images while attenuating pixel values representative of high-density areas.

Representations of the resultant images produced after step 503 are shown in FIGS. 5b and 5e.

At step 504, the multi-dimensional color space (represented as color image shown in FIG. 5b) is now converted to an HSL color space. In this embodiment, RGB values are converted to luminance, hue, and saturation values, as shown below in the following example:

(Hue, Saturation, Lightness, Zone)
(0.0, 0.0, 0.2, Red)
(0.0, 0.0, 0.1, Cyan)
(0.0, −1.0, 0, Master)

The image can be displayed first in RGB color or after conversion in HSL color space in step 505.

The image in FIG. 5c (and corresponding image 5f) is created from the image in FIGS. 5b and 5e by setting the master saturation for all hues in the HSL color space to −100% saturation. As a result, hue is no longer a factor in the expression of the image. Luminance values however, are still adjustable and changing the luminance values of various hues in the color space can alter the grayscale representation of those values. In some embodiments, the red and cyan luminance values are adjusted to 0.2 and 0.1 respectively. This brightens the gray values of the general breast background, highlights the interior portion of dense tissues such as cancerous lesions, and creates separation between the fine structure and the fatty tissue of the breast. The image can be converted to a single channel image containing only luminance in step 507 (and shown in FIG. 5c).

At this stage in processing, areas very fine structures associated with low-density luminance values are separated from the low-density, low-frequency areas 510 of the breast parenchyma, boundary, and chest wall. Compared with the diffuse grayscale mammographic image, visually distinguishable boundaries have been formed based on tissue structures.

HD Algorithm

Embodiments of the invention regarding the HD algorithm provide visualizations that are designed to reveal details in an image (e.g., original mammogram) that occur in the very highest density areas of the image. Structures such as breast abnormalities and cancerous lesion are revealed from the surrounding dense bright/white areas and become clearly defined.

Figure 6I:
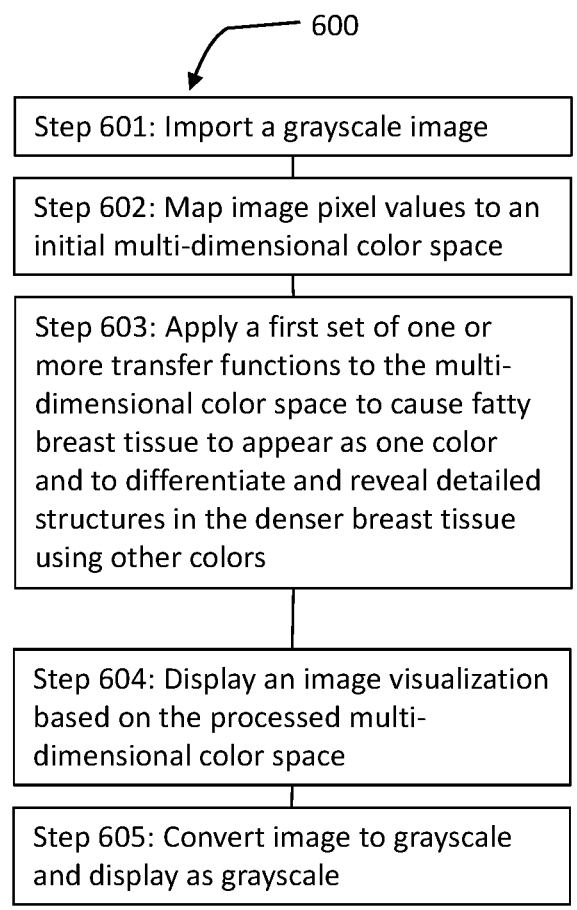

FIG. 6i is a flow chart illustrating a method 600 for creating a HD visualization from a grayscale image, according to at least one embodiment of the invention.

At step 601, processor 252 imports a grayscale image. FIG. 6a shows an exemplary grayscale image of a mammogram, according to at least one embodiment of the invention.

At step 602, processor 252 maps the grayscale image to a multi-dimensional color space.

At step 603, processor 252 applies a first set of one or more non-linear transfer functions (e.g., HD PLUT 1 local micro-contrast algorithm) to the multi-dimensional color space. Representations of the first set of one or more non-linear transfer functions are shown in FIGS. 6g and 6h respectively. FIG. 6g shows the color values of the LD PLUT (look-up table) that has been optimized to reveal breast structures in mammographic images. FIG. 6h show graphic representations in a coordinate system (e.g., that can be created from the PLUTs in FIGS. 6h). In these embodiments, a first transfer function is applied to the luminance color space layer to invert the luminance values 606 of the breast image. A red channel 607 amplifies the low-density areas of the image while attenuating high-density breast areas. The green channel 608, graphically shown in FIG. 6h as a discontinuous mapping of green channel values, colorizes the breast boundary and contributes with the red channel to make the breast background a yellow color. In some embodiments, the high-density breast tissue is greater than a lower 50% range; a lower 40% range; a lower 30% range; a lower 20% range; or a lower 10% range. The blue channel 609 adds color to define the outer boundary of the breast. The design of this local micro-contrast convergence algorithm, and its related PLUT values, can function to reveal details in any portion of the image regardless of the percentage of high density in the breast. In some embodiments, step 603 amplifies the low-density areas of industrial or veterinarian images while attenuating high-density breast areas.

At this stage in processing, areas of the image containing very high-density tissue structures 610 are separated from the low-density areas 611 of the breast parenchyma, boundary, and chest wall and cancer is further distinguished from among other high-density areas of the breast. Compared with the diffuse grayscale mammographic image, visually distinguishable boundaries have been formed based on tissue structures.

The image can then be displayed in multi-dimensional color space step 604 (e.g., as shown in FIG. 6b) or converted to a grayscale image at step 605 before being displayed (e.g., FIG. 6c) using a weighted conversion of R, G, and B values to achieve a luminance value according to the following formula: 0.30*R+0.59*G+0.11*B=luminance value.

MC Algorithm

Embodiments of the invention regarding the MC algorithm provide visualizations that are designed to reveal details in an image (e.g., original mammogram) that occur in the very highest density areas of the image, mainly small structures such as calcifications are revealed from the surrounding dense bright/white areas and become clearly defined.

Figure 7J:
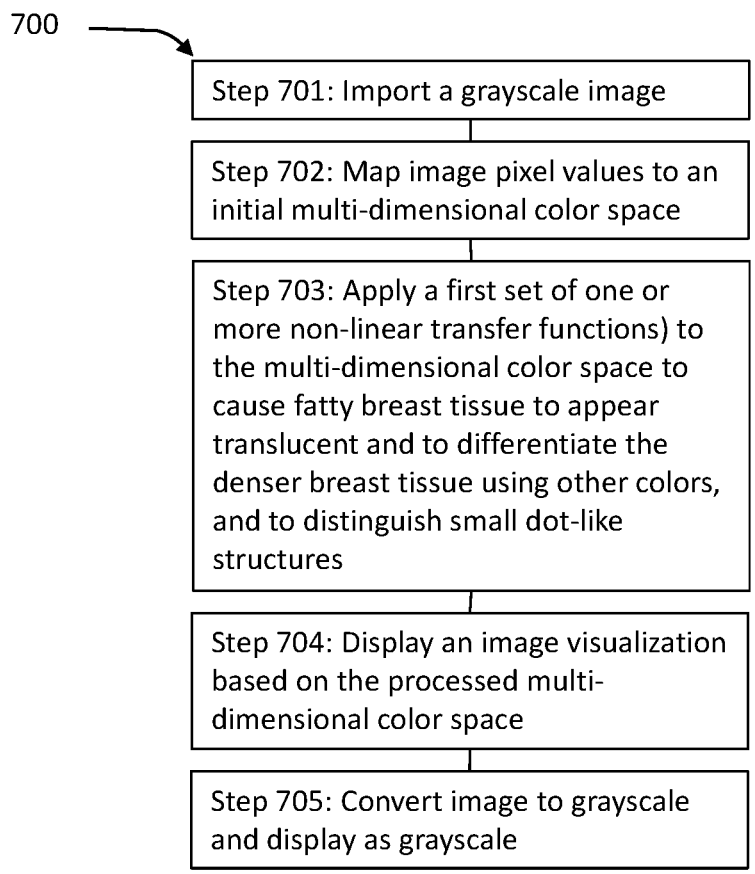

FIG. 7j is a flow chart illustrating a method 700 for creating a MC visualization from a grayscale image, according to at least one embodiment of the invention.

At step 701, processor 252 imports a grayscale image. FIG. 7a shows an exemplary grayscale image of a mammogram, according to at least one embodiment of the invention.

At step 702, processor 252 maps the grayscale image to a multi-dimensional color space.

At step 703, processor 252 applies a first set of one or more transfer functions (e.g., MC PLUT 1 local micro-contrast convergence algorithm) to the multi-dimensional color space. Representations of the local micro-contrast convergence algorithm are shown in FIGS. 7h and 7i. FIGS. 7h shows the color values of the MC PLUT (look-up table) that has been optimized to reveal breast structures in mammographic images. FIG. 7i show graphic representations in a coordinate system. In these embodiments, a transfer function is applied to the luminance space 706, to discontinuously invert the luminance values of the breast image. The red channel 707 attenuates a large portion of the image employing a discontinuous mapping of red channel values. The green channel 708 values contribute to creating a brown tone to the high-density areas of the breast. The blue channel 709 slightly tints the fatty tissue area of the breast.

The design of this local micro-contrast convergence algorithm, and its related PLUT values, function to reveal the presence of micro-calcifications in any portion of the image regardless of the percentage of high density in the breast.

At this stage in processing, micro-calcification structures, even in very high-density areas of the image, are separated from among other high-density areas of the breast. Compared with the diffuse grayscale mammographic image, visually distinguishable calcifications have been more clearly revealed. In some embodiments, step 703 can reveal the presence of small high density structures in any portion of an industrial or veterinarian image regardless of the percentage of high density in the surrounding object.

The image can then be displayed in multi-dimensional color space at step 704 (e.g., FIG. 7b) or converted to a grayscale image at step 705 (e.g., FIG. 7c) using a weighted conversion of R, G, and B values to achieve a luminance value according to the following formula: 0.30*R+0.59*G+0.11*B=luminance value. FIG. 7c is an enlarged section of the image in FIG. 7b after being converted to grayscale. The small black microcalcifications 710 can be distinguished from the light background more easily than in the original image.

RF Algorithm

Embodiments of the invention regarding the RF algorithm provide visualizations that are designed to emphasize extremely fine structures and details in an image (e.g., original mammogram). Structures such as spiculations and milk ducts are clearly defined as are structures within high density areas of the rest including those of cancer. In some embodiments, the RF visualization is shown as an overlay on the original image to improve visibility by a user (e.g., radiologist).

Figure 8U:
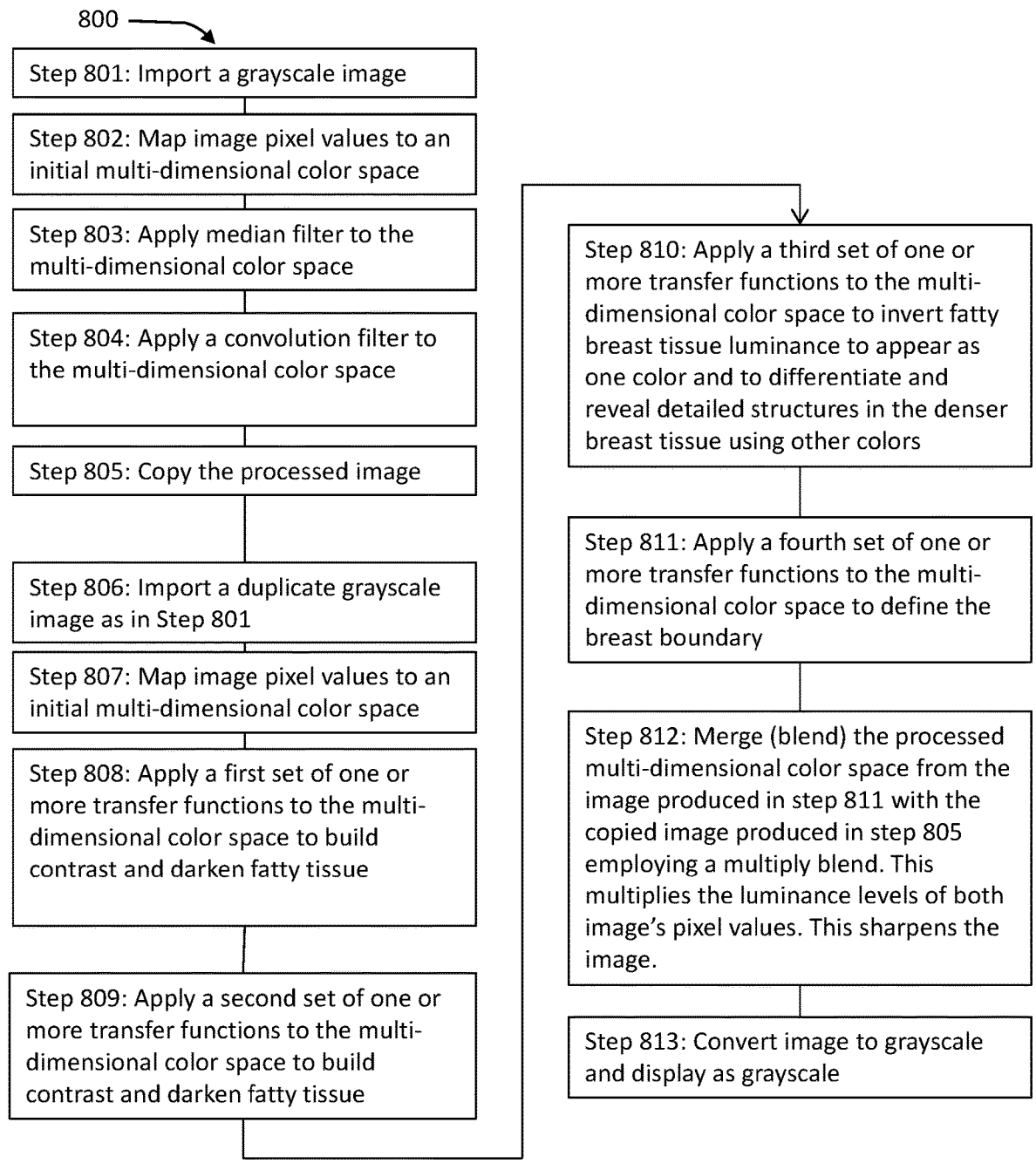

FIG. 8u is a flow chart illustrating a method 800 for creating a RF visualization from a grayscale image, according to at least one embodiment of the invention.

FIGS. 8b to 8c to 8l to 8m to 8s illustrate the results obtained by applying multiple local micro-contrast convergence transformations iteratively beginning with an original mammogram at FIG. 8a. FIGS. 8e to 8f to 8n to 8o and 8t illustrate the results of the same RF transformational sequence steps as applied to an original gradient grayscale image at 8d.

FIGS. 8g, 8h, 8p, and 8q show the color values of the RF PLUT (look-up tables) that have been optimized to reveal breast structures in mammographic images. FIGS. 8i, 8j, 8k and 8r show graphic representations in a coordinate system (e.g., that can be created from the PLUTs in FIGS. 8g, 8h, 8p, and 8q.

At step 801, processor 252 imports a grayscale image. FIG. 8a shows an exemplary grayscale image of a mammogram, according to at least one embodiment of the invention.

At step 802, processor 252 maps the original grayscale image to a multi-dimensional color space.

At step 803, processor 252 applies a median filter of radius 1 to the multi-dimensional color space of the original grayscale image.

At step 804, processor 252 applies a convolution filter to the multi-dimensional color space of the original image. In some embodiments, convolution filtering can be used to modify the spatial frequency characteristics of an image.

In operation, the convolution filter 804 is applied to each pixel in the multi-dimensional color space by replacing each pixel value with a weighted average of the pixel value and its neighboring pixel values. The pattern of neighboring pixel values is called the "window", which is applied, pixel by pixel, over the entire image. In some embodiments, the convolution filter is a 3×3 or radius=1 convolution filter. In other embodiments, matrix combinations such as 5×5, 8×8 can be used.

In one embodiment, the values of the 3×3 convolution filter matrix are shown in Table 1 as follows:

TABLE 1

| -4 | -1 | 0 |
| 0 | 1 | -1 |
| 6 | 0 | 1 |

At step 805, processor 252 copies the multi-dimensional color space of the processed image after step 804.

At step 806, processor 252, imports a duplicate of the same grayscale original image as utilized at step 801.

At step 807, processor 252 maps the duplicate image to a multi-dimensional color space.

At step 808, processor 252 applies a first set of one or more transfer functions (e.g., local micro-contrast convergence transfer function RF PLUT 1) to the multi-dimensional color space of the duplicate image. In these embodiments, a first transfer function (e.g., of local micro-contrast convergence function RF PLUT 1) is applied to the luminance color space 814 to elevate darker values of the image and attenuate mid tones. In some embodiments, step 808 can elevate darker values of the industrial or veterinarian image and attenuate mid-tones.

In these embodiments, a second transfer function, step 809 (e.g., of local micro-contrast convergence function RF PLUT 2) is applied to the luminance color space 815 to further attenuate mid tones. In these embodiments, mid tones are attenuated to a minimum at a luminance value of 1 in an image of 8-bit grayscale luminance range (0-255). In some embodiments, fatty tissue is elevated slightly at a maximum peak level 47 and transformed to 71. As a result, fatty tissue 816 is separated from the dense areas of the breast 817. In some embodiments, step 809 can slightly elevate low-density areas of industrial or veterinarian image and attenuate mid-tones.

FIGS. 8i, 8j, 8k and 8r show Cartesian plots illustrating a representation of an exemplary PLUT transfer function (e.g. and generated from PLUTs applied by the processor 252) according to at least one embodiment of the invention. In these Cartesian plots, the color spaces, coordinates, and values have been previously described and illustrated in FIG. 2a.

FIG. 8b shows an exemplary image of a mammogram based on the multi-dimensional color space after applying the first set of one or more transfer functions to elevate darker values of the image and attenuate mid tones, according to at least one embodiment of the invention.

FIG. 8c shows an exemplary image of a mammogram based on the multi-dimensional color space after applying a second set one or more transfer functions to further attenuate mid tones, according to at least one embodiment of the invention.

In FIG. 8l, at step 810, processor 252 applies a third set of one or more transfer functions (e.g., local micro-contrast convergence function RF PLUT 3) to the multi-dimensional color space of the image in FIG. 8c to result in image shown in FIG. 8l. In these embodiments, the third transfer function is applied to the luminance color space 818 create a discontinuous invert in the luminance values. In some embodiments, step 810 can discontinuous invert in the luminance values of industrial or veterinarian images.

In these embodiments, other "color" functions 819 of the third set of transfer functions can be applied to the color space layers to add subtle color hues.

At step 811, processor 252 applies a fourth set of one or more transfer functions (e.g., local micro-contrast convergence function RF PLUT 4) to the multi-dimensional color space of the image in FIG. 8l to result in image shown in FIG. 8m. In some embodiments, the RF PLUT 4, also shown graphically in FIG. 8q, is applied to the luminance channel 820 to create an increase in the luminance values of the lower densities of the image and to expand the tonal values associated with cancer and further define the breast boundary. In some embodiments, step 811 can increase the luminance values of the lower densities of industrial or veterinarian images to expand the tonal values associated with structural defects and further define the objects boundaries.

At step 812, processor 252 merges the processed multi-dimensional color space from the image in step 811 (e.g., FIG. 8m) with the copied image from step 805 (e.g., FIG. 8a) by employing a multiply blend. In some embodiments, the two images are blended with an opacity of 100%. As a result, the merged image has an emphasis on high frequency structures and attenuation of low frequency information with the highest densities remaining in color.

In these embodiments, and other embodiments employing a merging function, the merging function can be utilized to allow mathematical functions to be applied to one or more resultant images that utilize optimal qualities from each of the combining images for a specific purpose. For example, an image expressing the boundaries of cancer tissue in an image may be combined with an image expressing high frequency information. Such a combination can simultaneously show the extent of a cancer as it relates to possible high-frequency structures such as spiculations and calcifications within the tumor.

FIG. 8t shows an exemplary image of a mammogram after, at step 812, merging of the color spaces of the two images from 805 and 811, applying a merging function of 50%, and converting to grayscale at step 813 according to at least one embodiment of the invention.

In some embodiments, an image can be superimposed with additional matrices (layers) that contain either additional images or processing functions such as convert to black and white or incorporate layers generated from previous processing such as from high-pass filtering. Features include, but are not limited to, create new, paste, flatten, duplicate, make adjustment layer, and merge functions.

GI Algorithm

Embodiments of the invention regarding the GI algorithm provide visualizations that are designed to isolate, visualize, and characterize high-density structures and details in an image (e.g., original mammogram), and display them in a grayscale resultant image. Variations within the dense breast tissue are reflected in the darker areas of the image. Structures such as cancerous and benign lesions are clearly defined as are structures within high density areas. In some embodiments, the GI visualization is designed to improve visibility of abnormalities by a user (e.g., radiologist).

Figure 9Q:
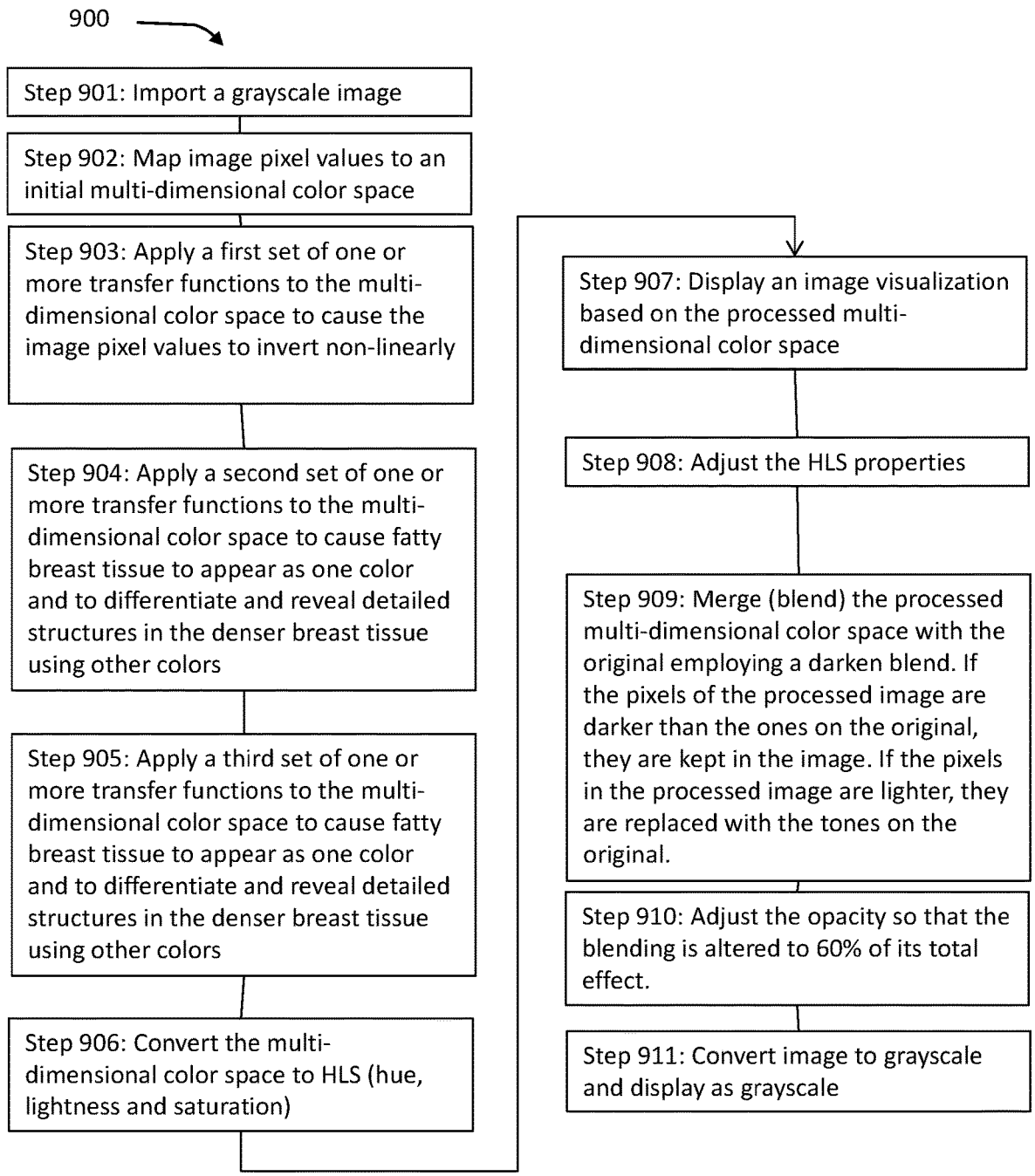

FIG. 9q is a flow chart illustrating a method 900 for creating a GI visualization from a grayscale image, according to at least one embodiment of the invention.

FIGS. 9b to 9c to 9m to 9n illustrate the results obtained by applying multiple local micro-contrast convergence transformations iteratively beginning with an original mammogram at FIG. 9a. FIGS. 9e to 9f to 90 to 9p illustrate the results of the same RF transformational sequence steps as applied to an original gradient grayscale image at 9d.

FIGS. 9g to 9h to 9k show the color values of the RF PLUT (look-up tables) that have been optimized to reveal breast structures in mammographic images. FIGS. 9i, 9j, and 9l show graphic representations in a coordinate system (e.g., that is created from the PLUTs in FIGS. 9g, 9h, and 9k respectively).

Referring now to FIG. 9q, at step 901, processor 252 imports a grayscale image. FIG. 9a shows an exemplary grayscale image of a mammogram, according to at least one embodiment of the invention.

At step 902, processor 252 maps the original grayscale image to a multi-dimensional color space.

At step 903, processor 252 applies a first set of one or more transfer functions (e.g., local micro-contrast convergence transfer function GI PLUT 1) to the multi-dimensional color space of the image. In these embodiments, one or more transfer functions are applied to the luminance color space 912 to non-linearly invert the luminance values of the image (e.g., as can be seen in FIGS. 9g GI PLUT 1 lookup table and graphic representation of the PLUT in FIG. 9i).

At step 904, processor 252 applies a second set of one or more transfer functions (e.g., local micro-contrast convergence function FIG. 9h GI PLUT 2) to process the multi-dimensional color space image illustrated in FIG. 9b.

FIG. 9c shows an exemplary image of a mammogram based on the multi-dimensional color space after performing step 904 to further isolate high-density areas of the mammogram, according to at least one embodiment of the invention.

The process performed at step 904 discontinuously alters the luminance channel 913 while adding color to the image with a discontinuous mapping of the red channel 914, and a low value non-linear set of values in the green channel 915. In these embodiments, the resultant image in FIG. 9c shows that the low-density tones are colored orange. In some embodiments, the red values of the low densities have values between 174 to 175 depending on the distribution in the original image. High density areas are bright, and boundaries of high density areas become dark. In some embodiments, step 904 can brighten high density areas and darken the boundaries associated with structural defects in industrial or veterinarian images.

At step 905, processor 252 applies a third set of one or more transfer functions (e.g., local micro-contrast convergence function GI PLUT 3) to the multi-dimensional color space of the image in FIG. 9c to result in image shown in FIG. 9m. In these embodiments, the third transfer function is applied to the luminance channel 916 to amplify the low, mid, and high values with attenuated values between the amplified values as seen in FIGS. 9k and 9l. This greatly separates tonal values in the resultant image and separates the breast from the background, emphasizes possible cancerous areas of the breast, and further defines the core of possible lesions in blue 918. The values in some lesions have a value of blue=200+/−5. In some embodiments, step 905 can greatly separates tonal values in the resultant image and separates the detailed structures from the background, emphasizes possible structural defects of the object, and further defines the core of possible objects in industrial or veterinarian images.

The red channel 917 of the third set of transfer functions are applied to the color space layers to add distinctive color hues to the breast 919.

The color image shown in FIG. 9m is now converted to an HSL color space in step 904 with RGB values being converted to luminance, hue, and saturation values. The image can be displayed first in RGB color or after conversion in HSL color space in step 906.

The resultant image (e.g., FIG. 9n) can be displayed in step 907 based on the processed multi-dimensional color space.

The image in FIG. 9m is altered in step 908 by setting the saturation for all hues in the HSL color space to −100% saturation. As a result, hue is no longer a factor in the expression of the image.

In step 909, the desaturated HSL color image in FIG. 9m is merged (blended) with the original image in FIG. 9a employing a darken blend. If the pixels of the processed image are darker than the ones on the original image, they are kept in the image. If the pixels in the processed image are lighter, they are replaced with the tones on the original.

In step 910, processor 252 adjusts the opacity so that the blending is altered to 60% of its total effect.

The blended and then merged image is then converted to a single luminance channel to form a grayscale image as shown in FIG. 9n. Details in the final image reveal a large cancerous tumor in the upper part of the breast. The GI local micro-contrast convergence algorithmic process has revealed the extent of the lesion 920, defined its boundaries, and revealed details within the core of the lesion. Use of other local micro-contrast convergence algorithmic sequences embodied in this document, can then be correlated to the identified area for further analysis and to discriminate between normal high-density tissues, benign, and cancerous lesions.

The image can be converted to a single channel image containing luminance only in step 911 using a weighted conversion of R, G, and B values to achieve a luminance value according to the following formula: $0.30*R+0.59*G+0.11*B$=luminance value.

RB Algorithm

Embodiments of the invention regarding the RB algorithm provide visualizations that are designed to isolate and clearly defined boundary and internal structures within high density areas of the breast including those of cancer while the rest of the breast is revealed as a dark gray.

Figure 10W:
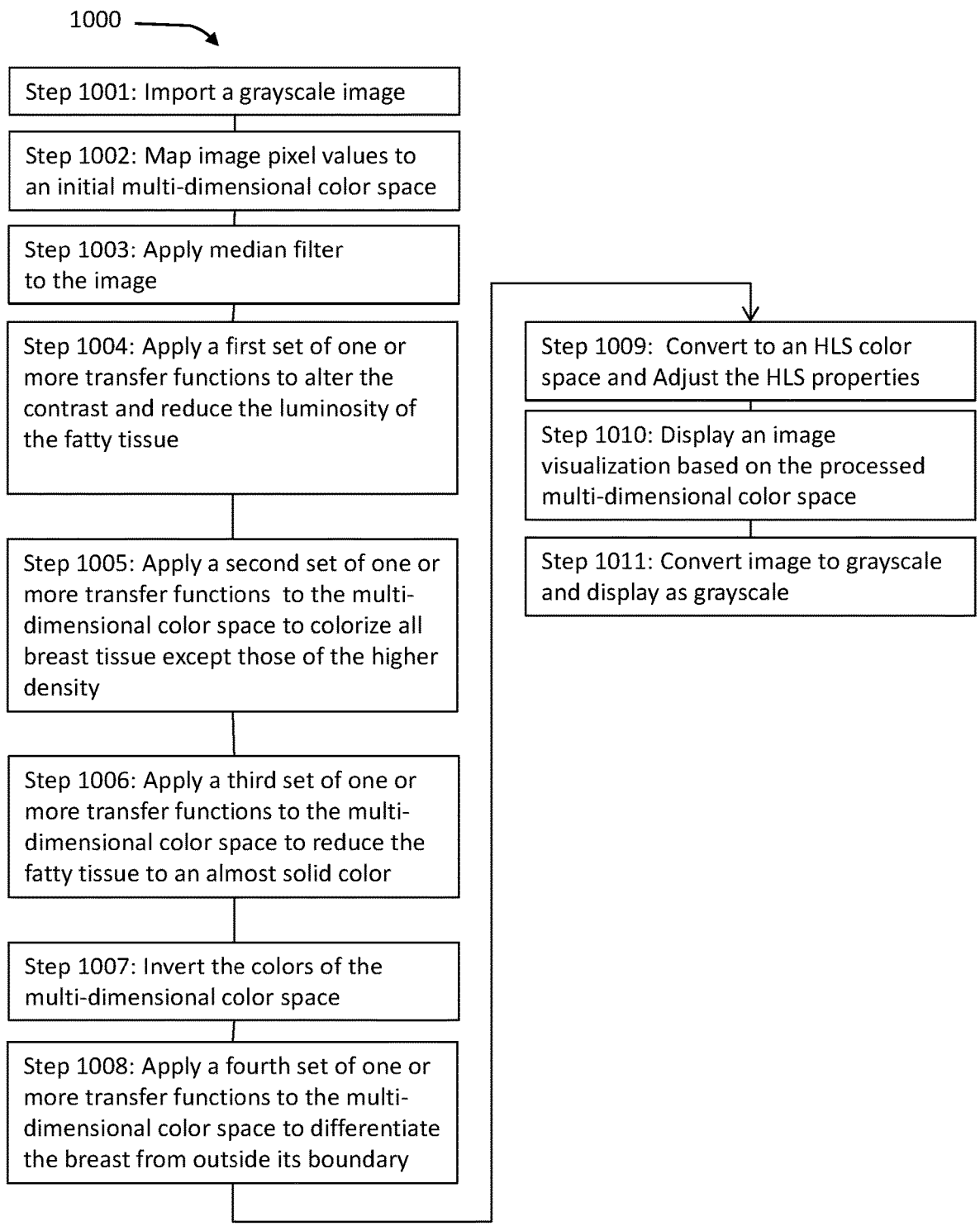

FIG. 10w is a flow chart illustrating a method 1000 for creating a RB visualization from a grayscale image, according to at least one embodiment of the invention.

FIGS. 10b to 10c to 10m to 10n to 10s to 10t illustrate the results obtained by applying multiple local micro-contrast convergence transformations iteratively beginning with an original mammogram at FIG. 10*a*. FIGS. 10*e* to 10*f* to 10*o* to 10*p*, to 10*u* to 10*v* illustrate the results of the same RB transformational sequence steps as applied to an original gradient grayscale image as shown in FIG. 10*d*.

FIGS. 10*g*, 10*h*, 10*k*, and 10*q* show the color values of the RB PLUT (look-up tables) that have been optimized to reveal breast structures in mammographic images. FIGS. 10*i*, 10*j*, 10*l*, and 10*r* show graphic representations in a coordinate system (e.g., that is created from the RB PLUTs in FIGS. 10*g* to 10*h*, 10*k*, and 10*q* respectively).

At step 1001, processor 252 imports a grayscale image. FIG. 10*a* shows an exemplary grayscale image of a mammogram, according to at least one embodiment of the invention.

At step 1002, processor 252 maps the original grayscale image to a multi-dimensional color space.

At step 1003, processor 252 applies a median filter of radius 3 to the multi-dimensional color space of the original grayscale image.

At step 1004, processor 252 applies a first set of one or more transfer functions (e.g., a local micro-contrast convergence transfer function RB PLUT 1) to the multi-dimensional color space of the duplicate image. In these embodiments, first set of one or more transfer functions (as shown in FIG. 10*g* and luminance transfer function 1012 of FIG. 10*i*) is designed to the discontinuously darken the luminance channel 1012 to darken the low- and mid-density areas values of the image as shown in FIGS. 10*b* and 10*e*. In some embodiments, step 1004 can alter the contrast and reduce the luminosity of the low-density areas in industrial or veterinarian images.

In these embodiments, at step 1005, processor 252 applies a second set of one or more transfer functions (e.g., local micro-contrast convergence function RB PLUT 2) 10*h* to the multi-dimensional color space. For example, in FIG. 10*j*, transfer functions are applied to the luminance 1013, red 1014, and blue 1015 color space layers. FIG. 10*c* shows an exemplary image of a mammogram based on the multi-dimensional color space after applying a second set of one or more transfer functions, according to at least one embodiment of the invention.

The luminance channel is altered to increase the contrast of the image. The red channel discontinuously elevates the dark areas of the image, reduces the highlights, and "flat-lines" the mid tones. The blue channel is reduced in value to control tonal values in the color image. In some embodiments, step 1005 can alter the luminance channel to increase the contrast of industrial or veterinarian images.

At step 1006, processor 252 applies a third set of one or more transfer functions (e.g., third local micro-contrast convergence function RB PLUT 3 FIG. 10*k* and plot 10*l*) to the multi-dimensional color space of the image in FIG. 10*c* to produce the image shown in FIG. 10*m*. In some embodiments, a transfer function is applied to the luminance channel 1016 to create a discontinuous "flat line" in the low-density areas of the image, attenuates the mid-tones, and slightly reduces the high-density luminance values. The red, green, and blue channels 1017 have transfer functions applied that colorize the low-density areas of the breast area. In these embodiments, other "color" functions of the third set of transfer functions are applied to the color space layers to add uniform color hues to the breast image. In some embodiments, step 1006 can alter the luminance channel to create a discontinuous "flat line" in the low-density areas of the image, attenuates the mid-tones, and slightly reduces the high-density luminance values of possible structural defect objects in industrial or veterinarian images.

At step 1007, the colors of the image shown in FIG. 10*m* are inverted to create resultant image in FIG. 10*n* in the mammogram and 10*p* in the gradient.

At step 1008, processor 252 applies a fourth set of one or more transfer functions (e.g., fourth local micro-contrast convergence function RB PLUT 4) 10*q* to the multi-dimensional color space image in FIG. 10*n* to result in the image shown in FIG. 10*s*. FIG. 10*r* shows that the luminance values 1018 of the low densities are brought to a maximum 255 level for all luminance values<74, another peak for mid-tones and for the brightest areas of the image. The red channel 1019 attenuates the low densities while maximizing the high densities with values set at 255 for all luminance values>160. The green channel 1020 contributes to the color hues of background and breast tissues. In these embodiments, the RB PLUT 4 FIG. 10*q*, also shown graphically in FIG. 10*r*, is applied to the luminance color space to differentiate the breast from the outside of its boundary. In some embodiments, step 1008 can be applied to the luminance color space to differentiate the structural defect objects in industrial or veterinarian images from the outside of its boundary.

At step 1009, the color image shown in FIG. 10*s* is converted to an HSL color space with RGB values being converted to luminance, hue, and saturation values. The image can be displayed first in RGB color or after conversion in HSL color space at step 1010. An exemplary HSL color space conversion is as follows:

(Hue, Saturation, Lightness, Zone)
(0.0, −1.0, −0.3, Magenta)
(0.0, −1.0, 0.3, Red)
(0.0, −1.0, −0.4, Yellow)
(0.0, −1.0, −0.4, Cyan)
(0.0, −1.0, 0.2, Blue)
(0.0, −1.0, −0.1, Green)

The final image in FIG. 10*t* is created from the image in FIG. 10*s* by setting the master saturation for all hues in the HSL color space to −100% saturation. As a result, hue is no longer a factor in the expression of the image. Luminance values however, are still adjustable and changing the luminance values of various hues in the color space can alter the grayscale representation of those values.

In step 1011, the image is converted to a single channel image containing luminance only. In this embodiment, all areas of non-pathology are revealed in the uniform gray 1021 of the breast image area where the average luminance value may be 130. This separation of possible areas of abnormalities 1022 reduces the "dwell time" for a radiologist, that is, the time they must spend investigating all areas of an image to locate the highest probability areas where cancer could occur.

Consistency of local micro-contrast convergence algorithm

FIGS. 11*a* through 11*d* illustrate the consistency with which one embodiment of this application performs across different imaging modalities. The pattern responses for breast images reveal consistent colors and tissue characterizations for modalities 3D Tomosynthesis in FIG. 11*a*, synthetic 2D from 3D in FIG. 11*b*, Full Field Digital Mammography (FFDM) in FIG. 11*c*, and digitized film in FIG. 11*d*. This provides a radiologist and their patients the ability to compare changes over time using only one set of algorithms, even when a patient's images were generated historically using different imaging modalities. These results verify one of the capabilities inherent in the local micro-contrast convergence approach as indicated in the local micro-contrast convergence hierarch of features identified as Modality Fusion in FIG. 1d.

Figure 11A:
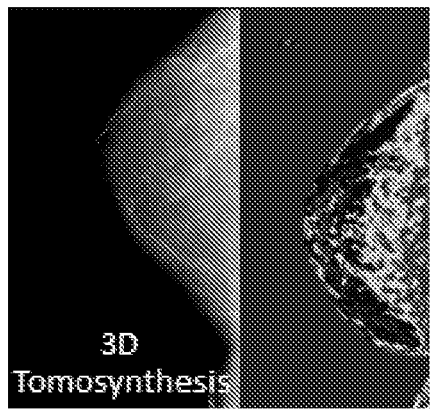
FIGS. 11a to 11d are an exemplary local micro-contrast convergence algorithmic sequence applied to four different mammograms generated from four different image acquisition modalities showing the same patterns from one local micro-contrast convergence algorithm in accordance with an exemplary embodiment of the present invention.
Figure 11C:
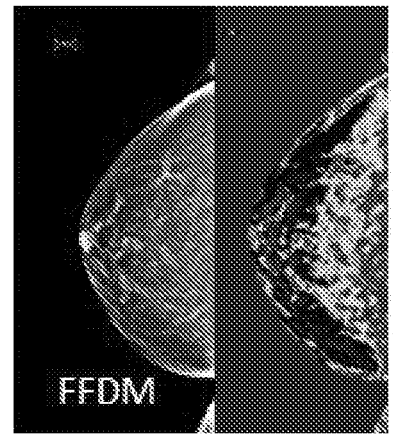
Figure 11B:
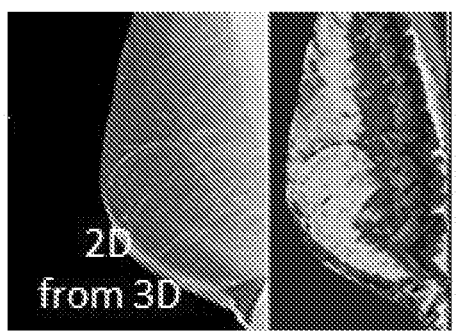
Figure 11D:
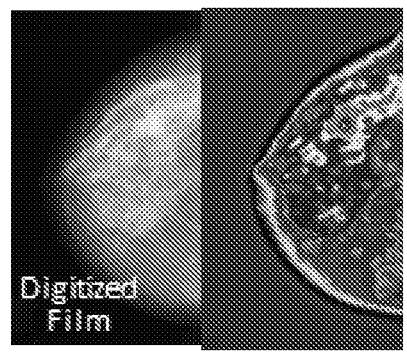
Figure 11E:
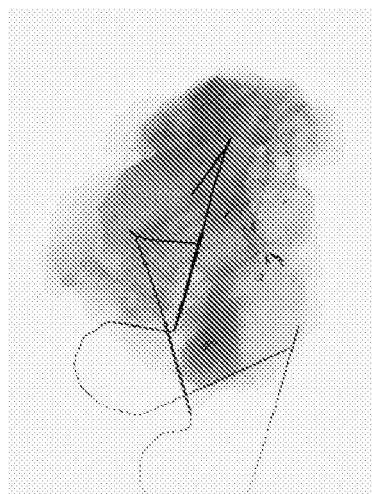
FIG. 11e is an X-ray image of surgically excised breast cancer tissue, in accordance with an exemplary embodiment of the present invention.
Figure 11F:
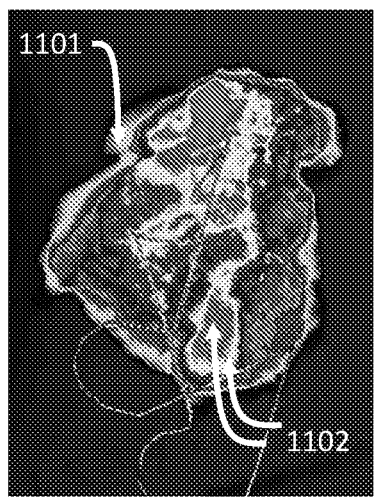
FIG. 11f depicts the results after applying an exemplary local micro-contrast convergence algorithmic sequence to the X-ray in FIG. 11e, in accordance with an exemplary embodiment of the present invention.

FIG. 11e shows an X-ray view of cancer in an exemplary mammogram image generated from excised breast tissue removed in surgery. FIG. 11f shows an exemplary mammogram image after processing the image using one or more methods described herein. The original image was processed using the CI Algorithm described earlier in this document. The black and magenta boundaries of the cancer 1101 are clearly defined, as are the changes in color inside of the boundaries 1102 indicating the extent of cancer development. Differences in color mapping of the interior of the cancer using the CI Algorithm can be correlated to known pathology and be used to indicate the structural differences in the tissue that may indicate angiogenesis, direction of growth, and the presence of necrotic tissue. The patterns may be further utilized to guide surgeries, immunotherapy applications, and biopsies. The patterns can also be utilized to monitor changes in a tumor during and after medical treatments such as chemo therapy, hormone therapy, immunotherapy, and radiation.

Embodiments of the invention, described herein, include methods that utilize a multi-algorithmic, multi-dimensional, computer-based process for the visualization and characterization of features, in context, in images. These local micro-contrast convergence methods are applicable in applications where the features are less than 1 mm in size, less than 900 microns in size, less than 850 microns in size, less than 800 microns in size, or less than 750 microns in size.

Figure 11G:
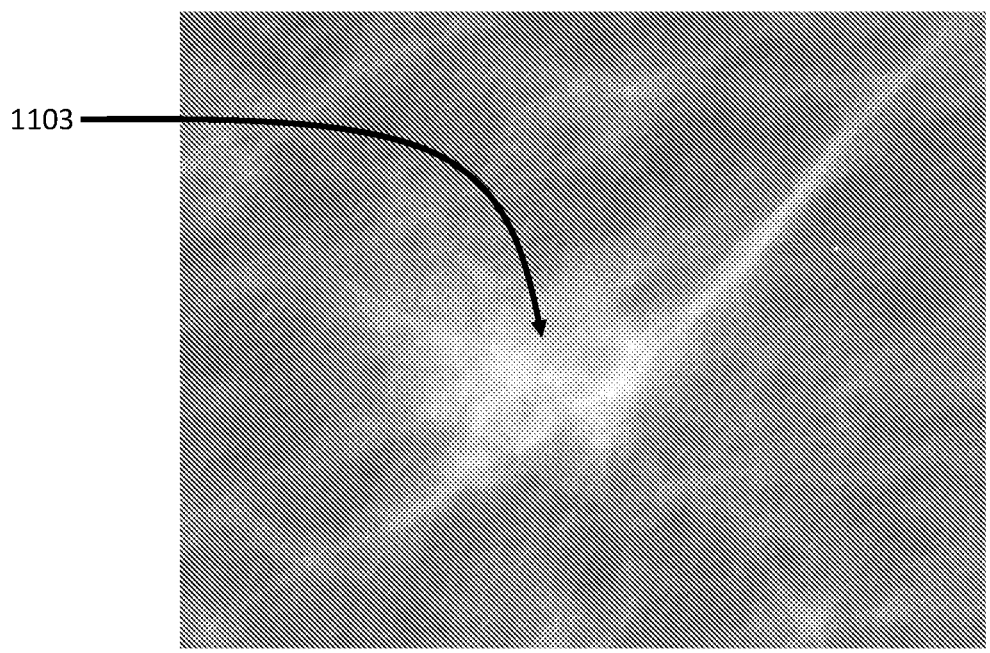
FIG. 11g is a close-up of a mammographic X-ray image revealing the presence of cancer, in accordance with an exemplary embodiment of the present invention.
Figure 11H:
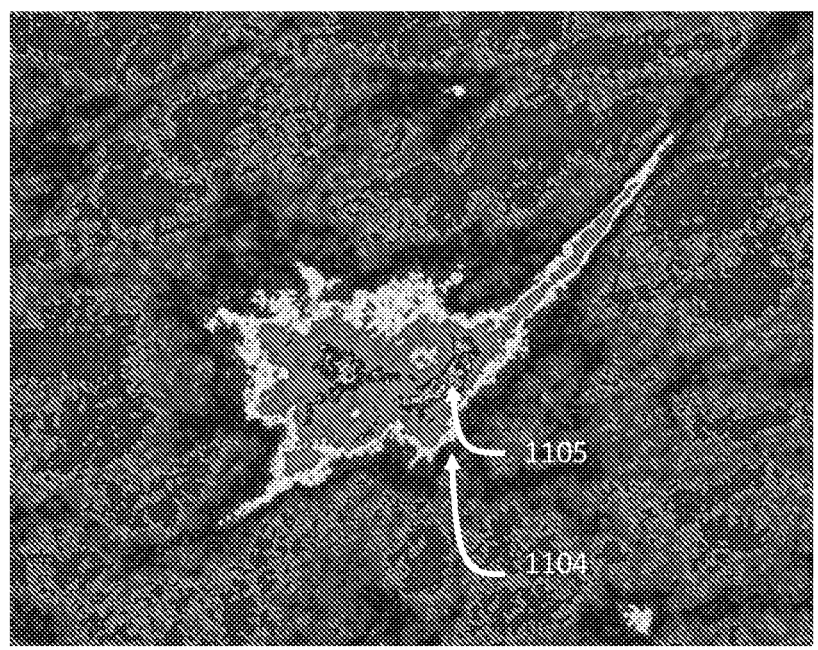
FIG. 11h depicts results after applying an exemplary local micro-contrast convergence algorithmic sequence to the X-ray in FIG. 11g, in accordance with an exemplary embodiment of the present invention.
Figure 12A:
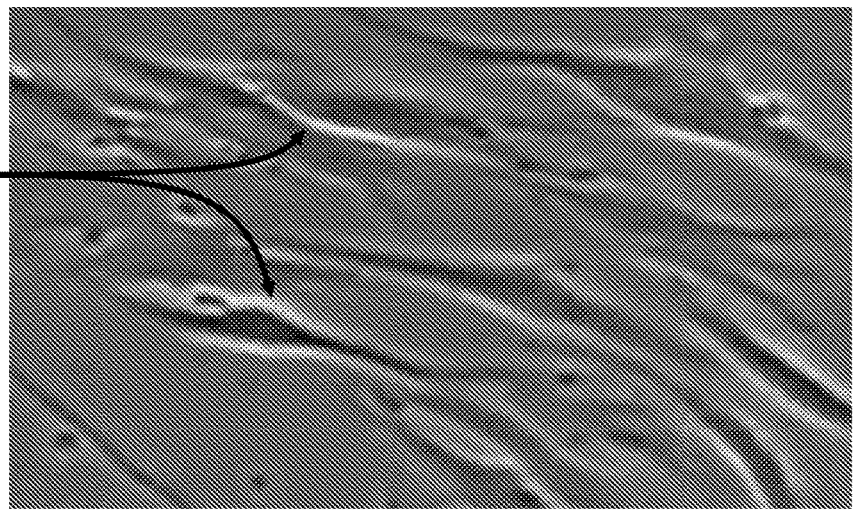
FIG. 12a is an original image showing cancer cells as imaged using photo microscopy, in accordance with an exemplary embodiment of the present invention.
Figure 12B:
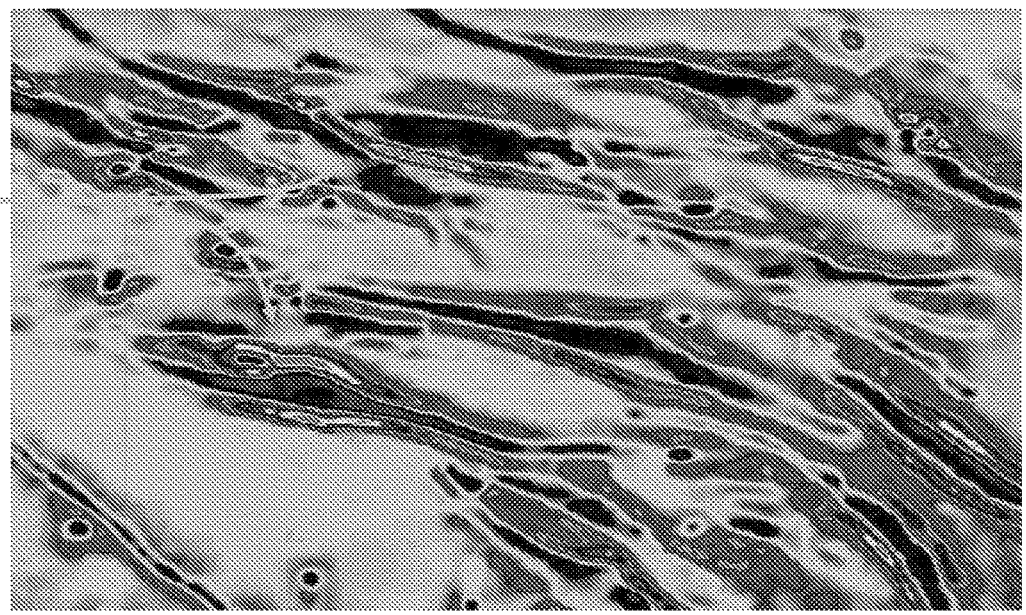
FIG. 12b is the result after applying an exemplary local micro-contrast convergence algorithmic sequence to the image in FIG. 12a, in accordance with an exemplary embodiment of the present invention.

FIG. 11g shows an enlarged view of a mammographic X-ray known to contain cancer 1103. FIG. 11h shows an exemplary mammogram image after processing the image using one or more of the methods described herein. In FIG. 11h, the black boundary of the cancer 1104 using the CI Algorithmic process described earlier in FIGS. 4a-4k is clearly defined as are details inside of the core of the cancer. The progression from yellow, to red to blue within the cancer show a progression cancer development to as small a size in the blue core 1105 being a size of only 980 microns. Multiple algorithmic expressions that are embodiments of the invention provide different characterizations and visualizations of the same tissue.

These methods are even applicable in applications where a feature of interest is located within another feature, where the feature of interest is less than 900 microns in size, less than 850 microns in size, less than 800 microns in size, or less than 750 microns in size and where the first feature is 1 mm in size or larger. In some embodiments, the feature of interest is between 700 and 900 microns in size.

In some embodiments, structures as small as 750 nm (microns) are identified using the above methods. Based on X-ray images where a pixel represents a dimension of breast tissue that is 75 nm in size, cancer cores can be expressed and characterized in sizes from 750 nm to 1 mm. It has been determined, through clinical testing, that structures as small as 500 nm can be revealed and differentiated in images whose pixel dimensions are 50 nm or smaller. Consequently, cancers of various forms as well as Ductal Carcinoma in Situ and precancerous Atypical Hyperplasia have been revealed using these methods in standard mammograms.

In some embodiments, structures (e.g., cancer cells or boundaries/cores of cancer cells) as small as 0.45 nm are visualized and characterized using embodiments of methods described herein. Based on images created using photo microscopy, cancer cores and boundaries within individual cancer cells shown at 1201 in FIG. 12a can be expressed and characterized in the same patterns shown 1202 in FIG. 12b as those visualized and characterized in aggregates of cancerous tissues as viewed in mammograms 108 in FIG. 1b using embodiments of methods described herein. Similar characterizations of cancerous lesion patterns can be observed and quantified when the cancer or other living tissues are grown in a culture medium.

In some embodiments, structures as small as about 200 nm (nanometers) are visualized and characterized using embodiments of methods described herein. In some embodiments, structures as small as about 75 nm (nanometers) are visualized and characterized using embodiments of methods described herein. Based on images created using Atomic Force microscopy, the surface of cancer cells shown at 1301 in FIG. 13a can be expressed and characterized in the same patterns shown 1303 in FIG. 13b, and enlarged view of 13b shown in FIG. 13c as those visualized and characterized in aggregates of cancerous tissues as viewed in mammograms 108 in FIG. 1b and 1202 in FIG. 12b using embodiments of methods described herein. Arrows 1302 and 1304 represent a connection or relationship between pixels areas on the original grayscale image 1301 with the same pixel areas in the processed image 1303 and enlarged view of 1303 shown at 1305.

Figure 13D:
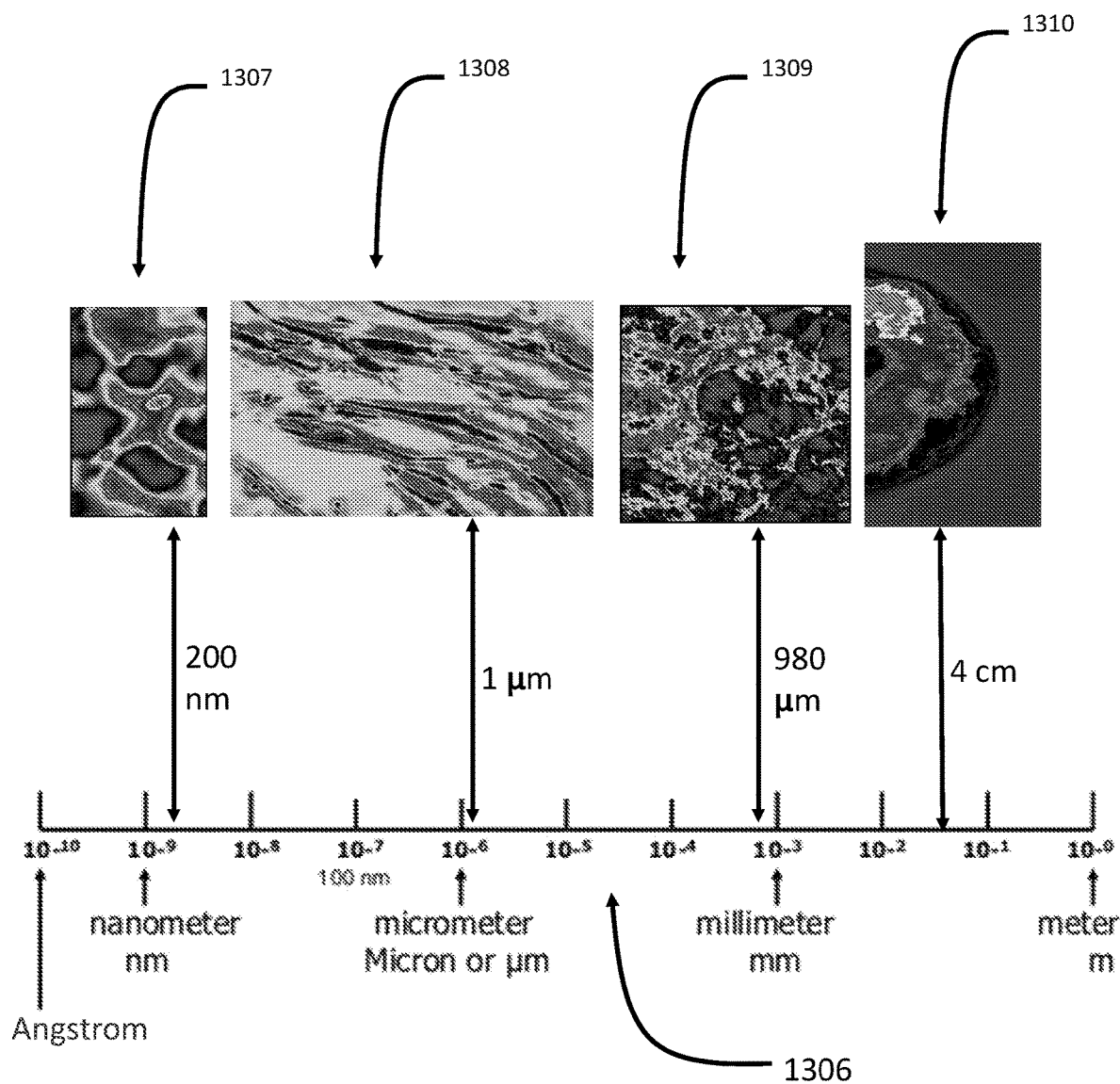
FIG. 13d depicts a graphic representation of the metric distance scale and four images containing cancer, cancer cell, or surface of cancer cell, in accordance with an exemplary embodiment of the present invention.

FIG. 13d illustrates the consistency of patterns expressed for cancer at different scales of magnification using different imaging modalities by applying the CI local micro-contrast convergence algorithm to each original image. Scale 1306 shows the metric scale of length from Angstroms to meters. The image 1307 is a visualization of the CI algorithm reflecting the pattern of a small part of the surface of a cancer cell at 200 μin in size when the original image was generated by an Atomic Force microscope that had a pixel resolution of 20 nm. The image 1308 is a visualization of the CI algorithm reflecting the pattern of cancer at the cellular level which ranges from 0.45 μm to 2.6 μm in length when the original image was generated by microscopy. The image 1309 is a visualization of the CI algorithm after processing an original mammogram generated using Full Field Digital Mammography (FFDM) with a pixel resolution of 50 μm. It reflects the pattern of cancer when it is forming as ductal carcinoma in situ (DCIS) which ranges from 900 μm to 2 mm in size. The image 1310 is a visualization of the CI algorithm after processing an original mammogram generated using Full Field Digital Mammography (FFDM) with a pixel resolution of 50 μm. It reflects the same pattern of cancer seen in the nm and μm ranges but now are visualized in sizes from millimeters to centimeters in dimension.

Embodiments of the invention, described herein, include methods that utilize a multi-algorithmic, multi-dimensional, computer-based process for the visualization and characterization of features of specific tissues in a patient or animal, in context, in images acquired from different imaging modalities. As a result, correlations of patterns can be made for a given tissue type among the images from more than one imaging modality. For example, FIGS. 14a, 14d, and 14g are resultant first-generation breast images created by X-ray, ultrasound, and CT scans respectively. FIGS. 14b, 14e, and 14h are resultant images obtained by applying the RF algorithm illustrated in FIG. 8u from step 801 to step 812. FIGS. 14c, 14f, and 14i respectively were created by applying the RB algorithm illustrated in FIG. 10w from step 1001 to step 1010 and then applying an edge detection filter on the output image from step 1010. This sequence of steps may be referred to herein as CR algorithm.

The cancer in each of the images is shown at cancer lesions 1401-1409 in FIGS. 14a-14i, respectively. Cancer lesion 1402, cancer lesion 1405, and cancer lesion 1408 all reveal similar patterns for the cancer even though they were generated using different imaging modalities and embodiments described herein. Similarly, cancer lesion 1403, cancer lesion 1406, and cancer lesion 1409 reveal the densely-packed contour patterns associated with cancerous lesions, even though the originating images were generated from different imaging modalities.

Figure 15A:
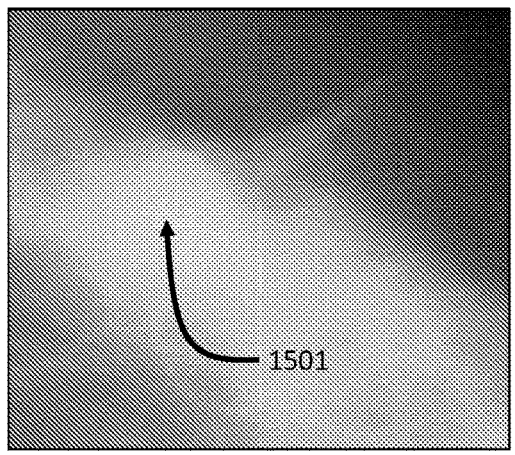
FIGS. 15a to 15f depicts the results of an exemplary local micro-contrast convergence algorithmic process, in accordance with an exemplary embodiment of the present invention.
Figure 15B:
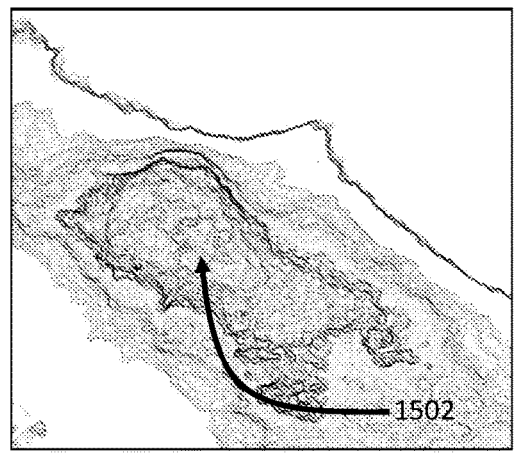
Figure 15C:
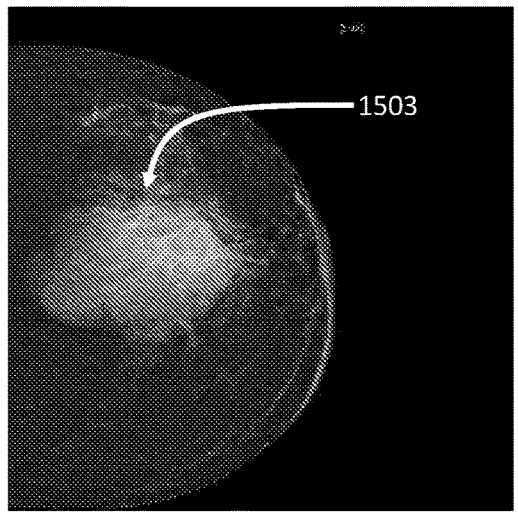
Figure 15D:
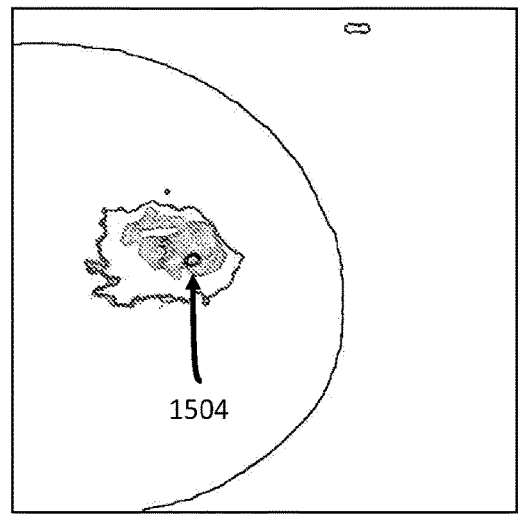
Figure 15E:
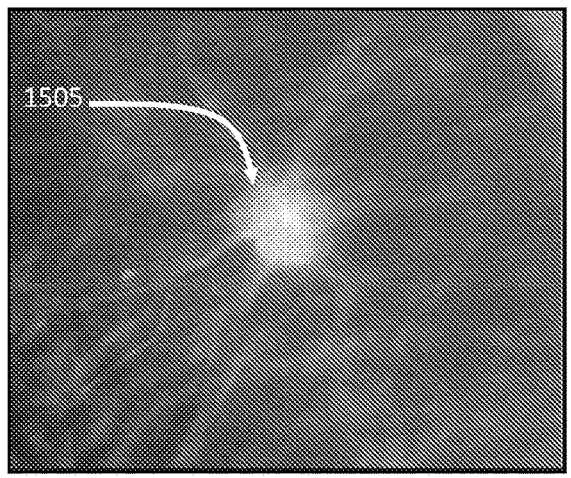
Figure 15F:
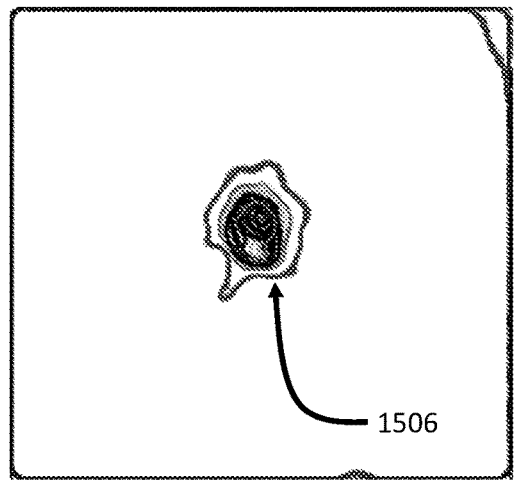

In some embodiments, the CR algorithm provides visualizations that are designed to reveal details in an image (e.g., original mammogram) that are mapped as contours within areas of abnormalities that can characterize differences between types of abnormalities. The luminance values of contour lines can vary in intensity depending on the relative contrast within the abnormalities. Additionally, contours that are very tightly spaced provide different diagnostic properties than those that are wider or more broadly distributed. For example, FIG. 15*a* shows a subsection of a mammogram containing a very diffuse benign lesion 1501 in dense breast tissue. FIG. 15*b* shows the resultant contour pattern of the benign lesion 502 after processing with the CR algorithm. The pattern is very diffuse with many light contour patterns not containing a central core. FIG. 15*c* shows a mammogram taken following breast surgery and there is a remaining scar representation 1503 that appears white at FIG. 1503. Contours of the scar representation 1504 revealed from the original mammogram in FIG. 15*c* by the CR algorithm are shown in FIG. 15*d*. Scar representation 1504 shows a small core but wide areas of either no contours or very light contours. FIG. 15*e* shows a magnified view of a mammogram image containing cancer represented by cancer lesion 1505. After processing the image shown in FIG. 15*e* using the CR algorithm, the image shown in FIG. 15*f* is generated. Contours of the cancer lesion 1506 reveals very tightly packed contours with a dark core that is associated with cancers of this type.

Figure 16A:
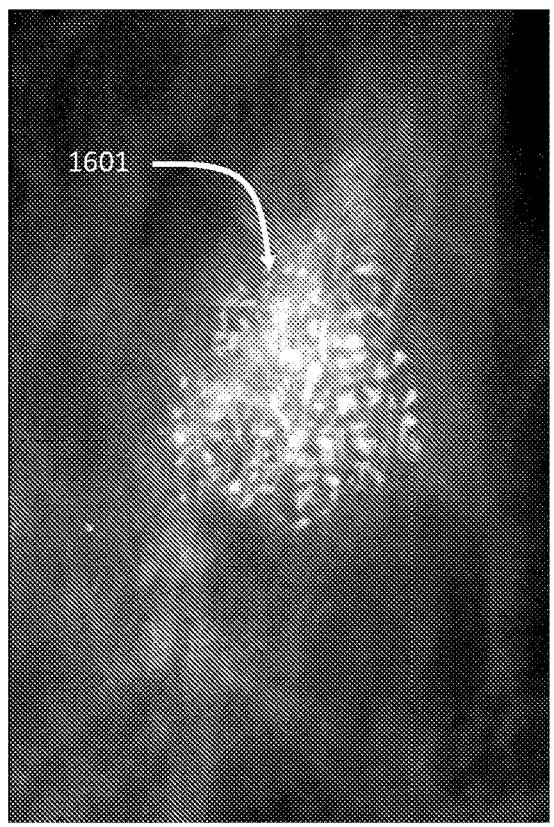
FIG. 16a is a close-up of a mammogram containing a large cluster of microcalcifications, in accordance with an exemplary embodiment of the present invention.
Figure 16B:
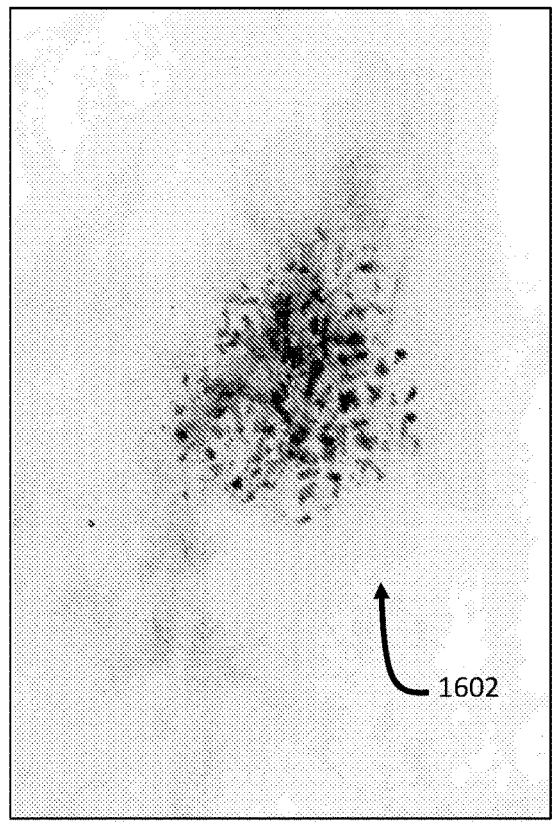
FIG. 16b is an exemplary local micro-contrast convergence algorithmic sequence result, in accordance with an exemplary embodiment of the present invention.

Some embodiments of the invention, described herein, include methods that utilize more than one algorithmic approach for processing digital image data for the purposes of visualizing and characterizing tissue structures, as described herein. FIG. 16*a* shows a close-up of a mammogram with a cancerous mass and large cluster of calcifications 1601. FIG. 16*b* is a resultant image created from processing the original image in FIG. 16*a* using the MC algorithm. This algorithmic sequence can be designed to remove darker luminance values having a value below 100 in an 8-bit grayscale image to isolate high luminance pixel values from their background. This provides a mechanism for subtracting areas containing fatty breast tissue (fat subtraction, where fat is represented as a darker color than breast tissue) in mammograms to assist clinicians in better assessing the image and locating calcifications and their shapes in diagnosing cancer.

Figure 16C:
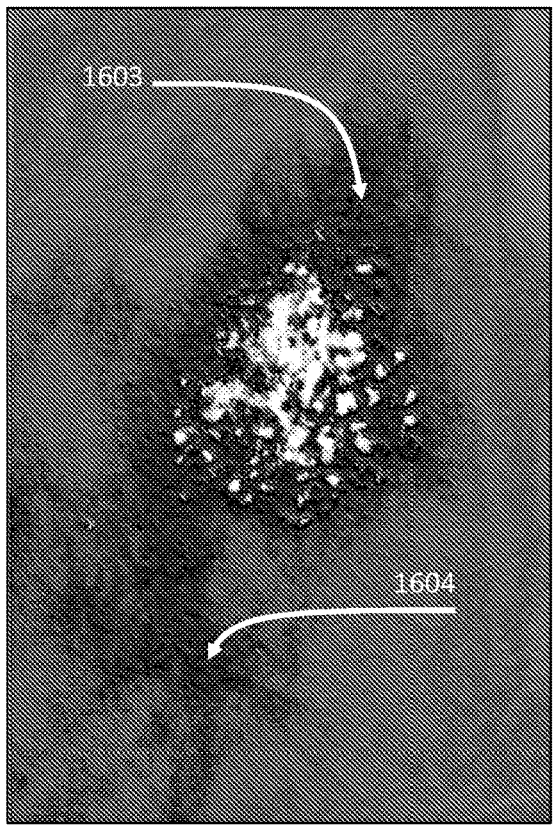
FIG. 16c is an exemplary local micro-contrast convergence algorithmic sequence result, in accordance with an exemplary embodiment of the present invention.

In another embodiment, FIG. 16*c* shows the result of processing the original image in FIG. 16*a* using the LD algorithm. This algorithm differentiates low luminance pixel value relationships in the image while still preserving the highest luminance value pixels. In FIG. 16*c* at element 1603 and element 1604, the cancerous mass associated with the calcifications is clearly defined as compared with the diffuse areas in the original image shown in FIG. 16*a*. At element 1605 and element 1606, the furthest extent of the boundaries (margins) of the mass are also more clearly defined as compared with the original image FIG. 16*a*. Embodiments of the invention utilizing the local micro-contrast convergence algorithmic approach provide the basis for visually characterizing tissues in medical images or materials in industrial applications that support feature identification and assessment for machine learning methodologies.

Figure 17A:
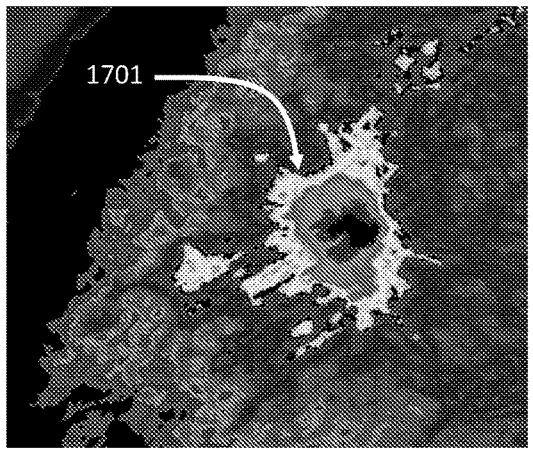
FIG. 17a-17c is an exemplary process for creating areas of interest (AOI) for machine learning, in accordance with an exemplary embodiment of the present invention.
Figure 17B:
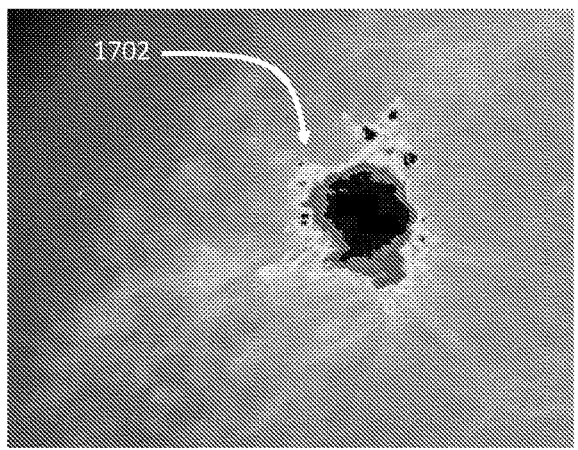
Figure 17:
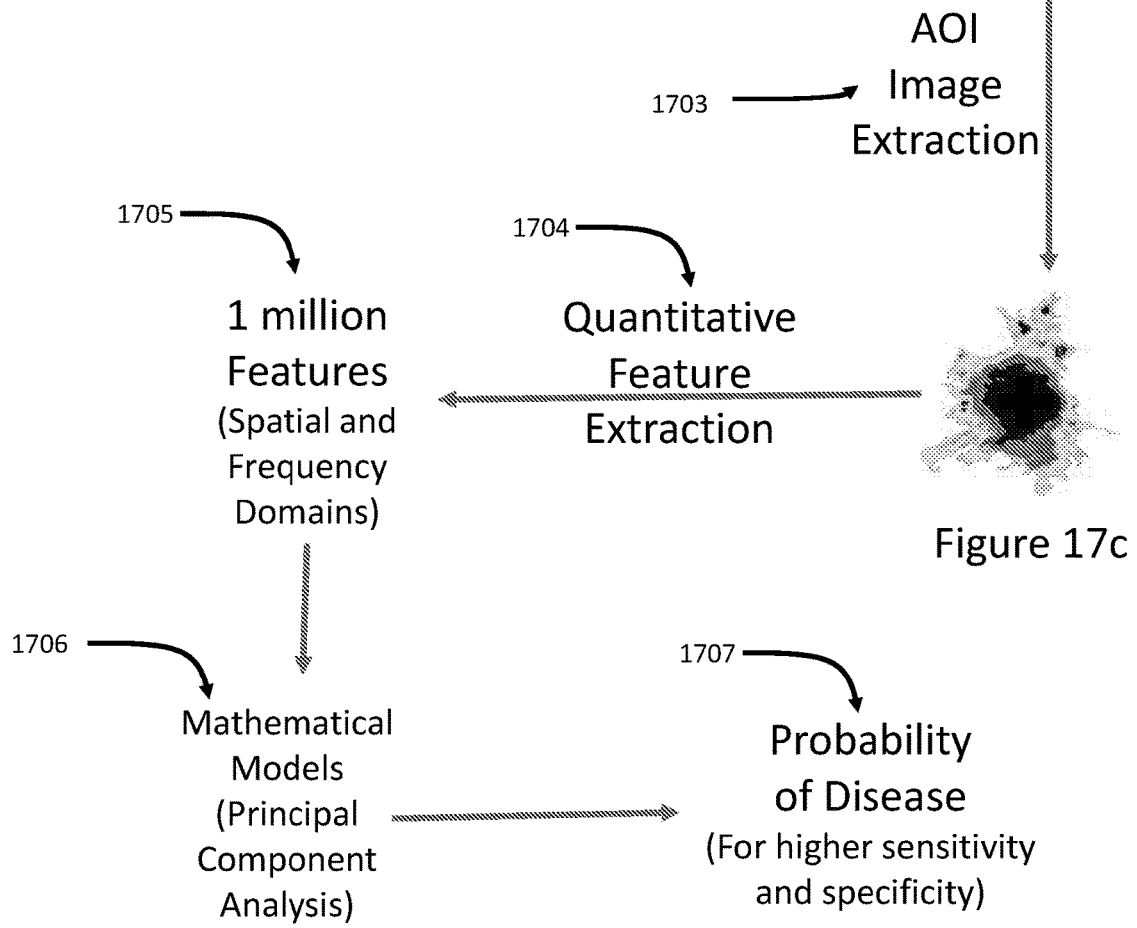

FIG. 17 shows an exemplary process for creating areas of interest (AOI) for machine learning using an exemplary local micro-contrast convergence algorithmic sequence, AOI extraction, feature extraction, feature analysis, principal component analysis, and generating probabilities of the occurrence of cancer according to at least some embodiments of the invention. Image 1709 shows the result of processing a close-up view of a mammogram using the CI algorithm as described in FIG. 4*k*. Areas of interest associated with known patterns of abnormalities in mammograms are shown at element 1701 of image 1709. This element 1701 is then isolated as shown at element 1702 in image 1710 using metrics associated with color patterns. In this example, colors containing yellow-gold, red, blue, and the black boundary of the abnormality are isolated from the processed image 1709. The isolated pixel values of the colors in element 1702 are extracted in step 1703 and a new image is made of only the extracted processed pixel values represented by element 1708 in image 1711. The area of interest 1702 is identified by scanning the pixels of the processed image to identify certain expressed color patterns (e.g., gold and red). In one possible embodiment, a second step involves mathematically determining the central point within any area of certain color pixels (e.g., gold pixels). This central point becomes the anchor or center for creating concentric circles outward from the center to identify the location of the pixels forming a color boundary (e.g., black boundary) of the cancer as revealed consistently by the CI algorithm. All pixels outside of the color boundary are then removed from the AOI image. In another embodiment, other local micro-contrast convergence algorithms can be used to determine the margins of the abnormality, such as the CR algorithm, as shown in FIG. 15*f*. Once the pixels within the margins has been identified, those pixels are copied and used to create a new image containing only the pixels within the area of interest as shown in image 1711. The element 1708 is then analyzed using quantitative feature extraction metrics at step 1704. Quantitative feature extraction such as High-separability feature extraction (HSFE) from data, basing on both standard and advanced characteristics of images can include such metrics as: color patterns and their distribution, the presence and relationship of black boundary patterns of AOI margins, Co-Occurrences, Gabor, Local Binary Pattern (LBP) analysis, Histograms of Oriented Gradients, Random Ferns, and Hough Forests. One million, or more, features are then used to mathematically evaluate the values in the extracted image in step 1705 using both spatial and frequency domains of analytics. The features assembled in step 1705 are then analyzed using mathematical models in step 1706 involving principal component analysis methodologies such as neural networks and support vector machines (SVM). The use of this analysis in machine learning, such as supervised learning models, are used to analyze data for classification and regression analysis. Given a set of training examples, the output classifies the object as belonging to one or the other of two categories. The SVM training algorithm builds a model that becomes a non-probabilistic binary linear classifier.

At step 1707, the location and probability of disease for the area of interest in the original mammogram at step 1707 is determined. The use of feature extraction after processing the original image using the CI algorithm provides higher levels of tissue characterization resulting in higher sensitivity and specificity of diagnosis than is accomplished using only the very diffuse gray and white pixel values in the original grayscale image as a basis for machine learning and predictive modeling.

FIG. 18 illustrates an exemplary methodology for correlating metrics from each of a plurality of processed images using different local micro-contrast convergence algorithms described herein, according to at least some embodiments of the invention. In some embodiments, utilizing local micro-contrast convergence algorithmic processing for feature extraction and machine learning, more than one local micro-contrast convergence algorithmic sequence can be employed. An isolated area of interest (AOI) from a mammogram is shown in image 1820 with the core of the cancer shown at element 1818. This AOI was generated by applying steps 1703 to 1707 of FIG. 17 after processing an original mammogram image with an exemplary local micro-contrast convergence algorithmic sequence. Having isolated the original pixel values, the original AOI pixels are duplicated n times. In this example, images shown from 1812 to 1817 (with the core of the cancer shown at elements 1830-1835, respectively) were created with the HD, LD, RF, CR, ED, and CI local micro-contrast convergence algorithms respectively. Each of the duplicated images 1812-1817 are then processed with different local micro-contrast convergence algorithms, described herein. In some embodiments, any number of local micro-contrast convergence algorithms that can be utilized to create duplicated images. The duplicated images, 1812 to 1817, can then be analyzed individually as shown in the process described in FIG. 17. Additionally, the metrics generated from the analytical process shown in FIG. 17 can be used to correlate features and probabilities generated from each of the newly-generated images. Element 1840 illustrates an additional methodology for correlating metrics from each of the images 1812-1817 as depicted with lines 1802 to 1808 representing each of the images. The rectangles in element 1840 represent the AOIs from each of the additional local micro-contrast convergence algorithmic processes. Arrows represent a connection from each of the images 1812-1817 to their respective layer and AOIs. This combination of layering creates a synthesized "multi-spectral" set of voxels that can be analyzed through the layers as shown with arrow 1800 and processed using steps 1704, 1705, and 1706 in FIG. 17 incorporated into the Multi-LMCC (local micro-contrast convergence) principle component analysis shown in step 1809. The output of the analysis 1810 is expressed as a probability of disease in step 1811.

Embodiments of the invention regarding the RB algorithm provide visualizations that are designed to reveal details in an image that are of low contrast, subtle in their differences from surrounding objects, and of clinical importance. The CT brain scan in FIG. 19a shows a very small hemorrhage at 1901 that was missed in diagnosis and the patient was sent home. The patient returned the following day with increased symptoms and a second CT scan FIG. 19b was performed and revealed a large right Sylvian subarachnoid hemorrhage (SAH) 1902 that was very visible in the image. FIG. 19c shows the results of processing the CT image in FIG. 19a with the RB local micro-contrast convergence algorithmic sequence described in FIG. 10w. In this example, the resultant image from the RB algorithm was not converted to grayscale, but in other embodiments, the resultant image can be converted to grayscale. The small hemorrhage that was missed in diagnosis is visible as hemorrhage 1903 in red. The hemorrhage visible in FIG. 19b is shown in FIG. 19d at hemorrhage 1904. Different densities of the fluid are revealed in the boundary and interior colors at hemorrhage 1904.

Figure 20A:
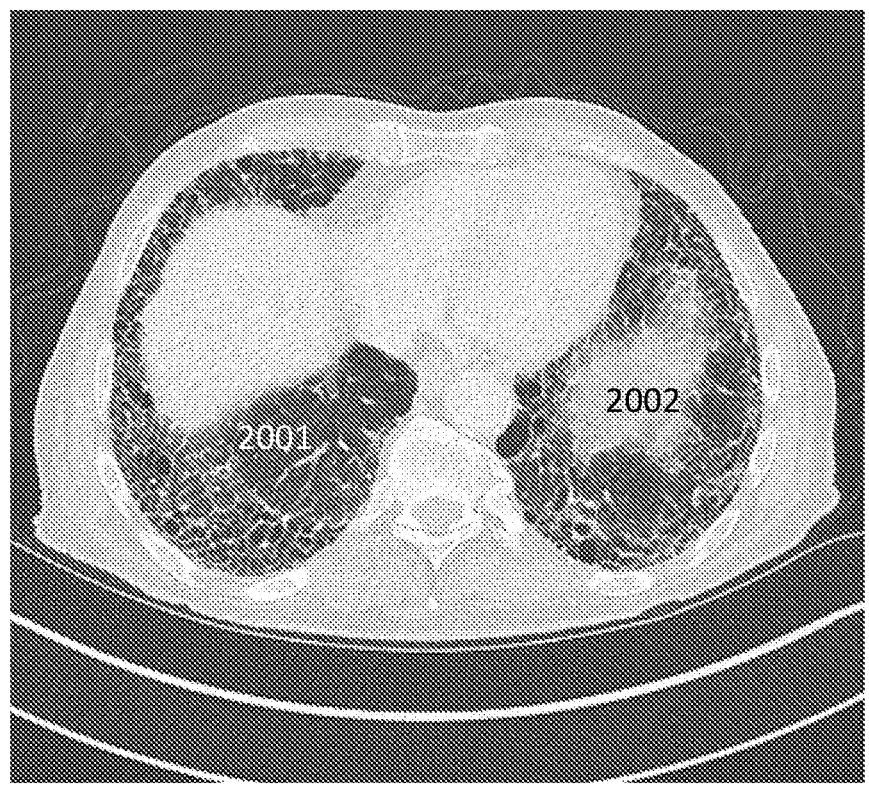
FIG. 20a is an original CT scan of a chest cavity, in accordance with an exemplary embodiment of the present invention.
Figure 20B:
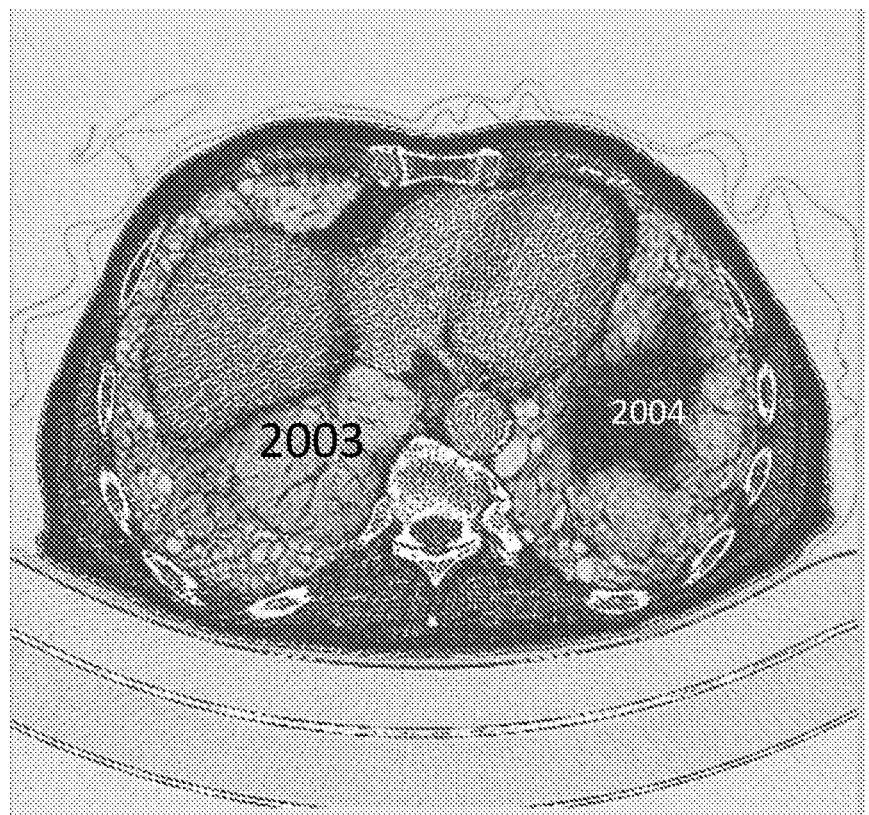
FIG. 20b depicts the results after applying an exemplary local micro-contrast convergence algorithmic sequence to the original image in FIG. 20a, in accordance with an exemplary embodiment of the present invention.
Figure 21A:
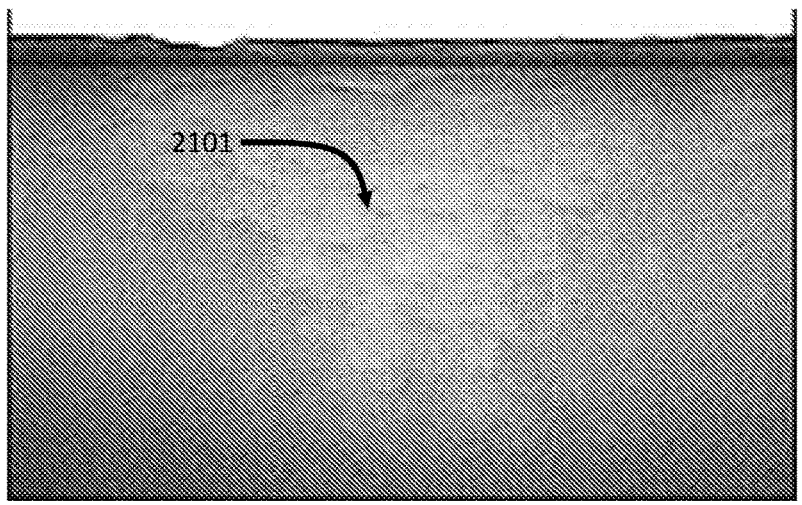
FIG. 21a is an original X-ray image of a pipe with corrosion, in accordance with an exemplary embodiment of the present invention.
Figure 21B:
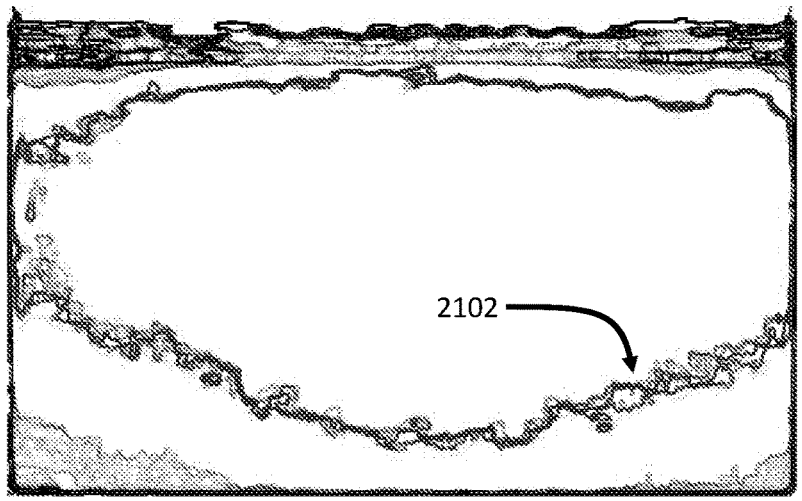
FIG. 21b shows the results after applying an exemplary local micro-contrast convergence algorithmic sequence to the original image in FIG. 21a, in accordance with an exemplary embodiment of the present invention.
Figure 21C:
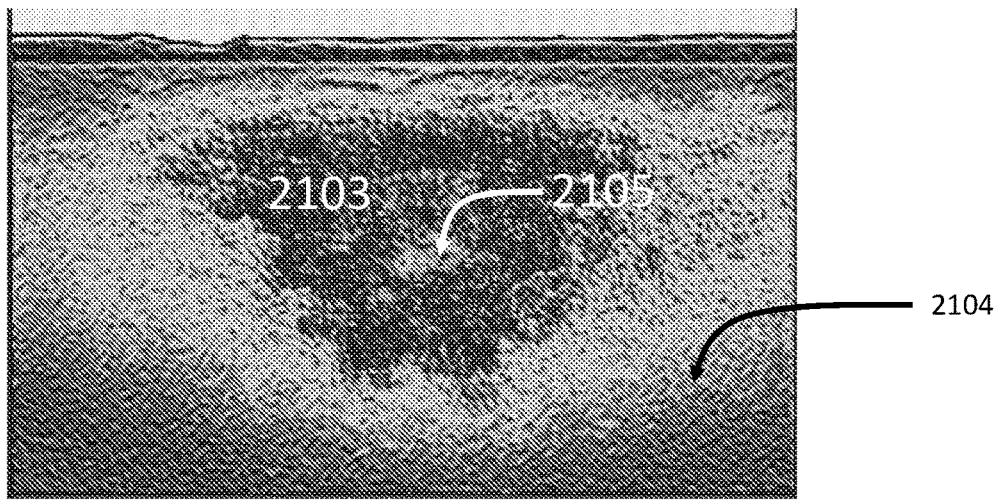
FIG. 21c depicts the results after applying an exemplary local micro-contrast convergence algorithmic sequence to the original image in FIG. 21a, in accordance with an exemplary embodiment of the present invention.

Embodiments of the local micro-contrast convergence algorithmic process can be employed in visualizing, characterizing, and analyzing a wide range of image types, from different imaging modalities, diseases, and tissue types. FIG. 20a is a chest CT with areas of the lungs 2001, 2002. A more detailed and textured expression of the tissues in FIG. 20a are shown in FIG. 20b after having been processed using the LD local micro-contrast convergence algorithm. The increased textural visual and frequency-based representation of the tissues shown at elements 2003 and elements 2004 make it easier for clinicians to make assessments and greatly increases the accurate diagnostic potential in machine learning. Embodiments of the local micro-contrast convergence algorithmic process can be employed in visualizing, characterizing, and analyzing a wide range of image types for industrial and security applications. Since the local micro-contrast convergence algorithmic approach works on pixel relationships, the sequencing of steps to achieve convergence for a given application can be easily modified and applied to other image processing requirements. FIG. 21a is an X-ray image of a structural defect of a rusting pipe with the center of the rust shown at element 2101. FIG. 21b shows the boundaries of the rust-generated structural defect at the edge of the contours at element 2102 utilizing the CR algorithm. The rust is further visualized in color in FIG. 21c after being processed with the CI algorithm. The boundary of the rust is shown at element 2104 and the variation and degree of rust can be seen as differences in color patterns with the greatest corrosion at element 2105.

All of the broad range of applications related to the adaptability of LMCC to many domains of image processing are possible because effective image analytics is an imaging problem, not a medical or industrial problem. Consequently, embodiments of the local micro-contrast convergence algorithmic process can be employed in visualizing, characterizing, and analyzing a wide range of image types related to both human and animal health applications.

Local Micro-Contrast Convergence Algorithm

Figure 22A:
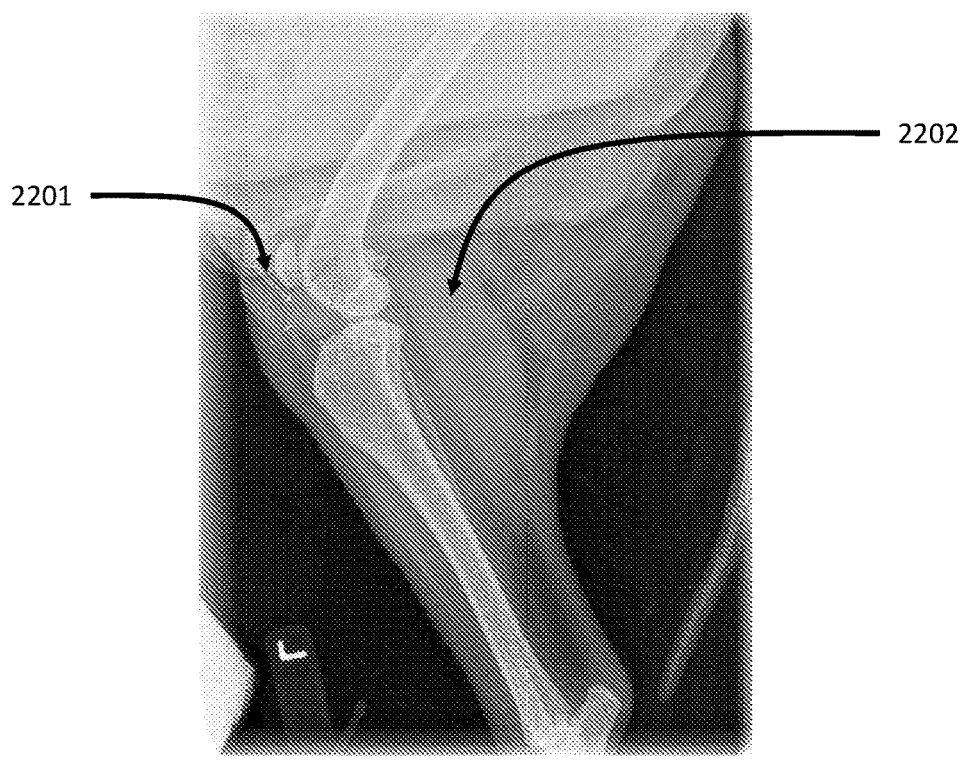
FIG. 22a is an original X-ray image of a dog's leg.
Figure 22B:
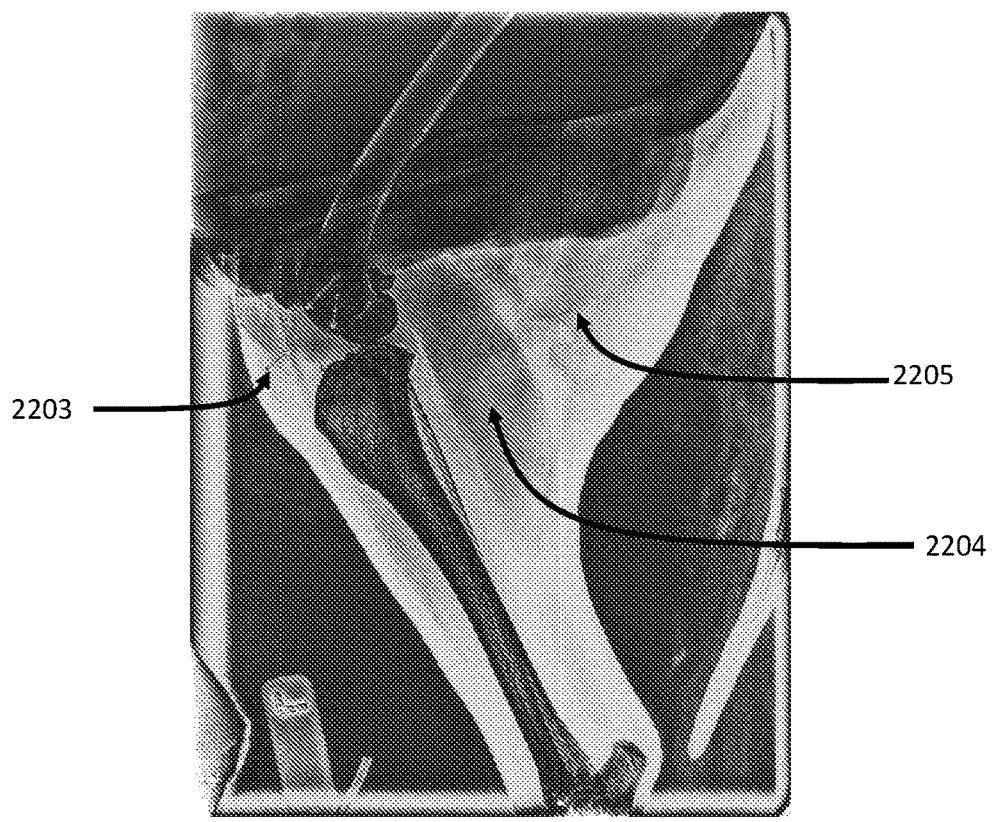
FIG. 22b is an original x-ray image after applying local micro-contrast convergence algorithmic sequence to FIG. 22a, in accordance with an exemplary embodiment of the present invention.

Further embodiments of the local micro-contrast convergence algorithmic process are depicted in FIGS. 22a-23b. FIG. 22a is an original X-ray image of a dog's leg taken at a veterinary clinic in a first visit with the doctor. While the dog was brought in for treatment of a leg problem, no diagnosis of pathology was made at this time. The veterinarian retrospectively placed arrows around the area suspected of having the sarcoma, shown in area 2201 and area 2202. In contrast, after utilizing the LD algorithm, FIG. 22b shows the extent of the sarcoma present, in area 2203, area 2204, and area 2205, in the original X-ray in FIG. 22a. FIG. 23a is an original X-ray image of the same dog's leg as imaged in FIG. 22a. This image was generated 3 months after the image depicted in FIG. 22a. The veterinarian placed arrows around the area suspected of having the sarcoma, as depicted by area 2301 and area 2302.

Figure 23A:
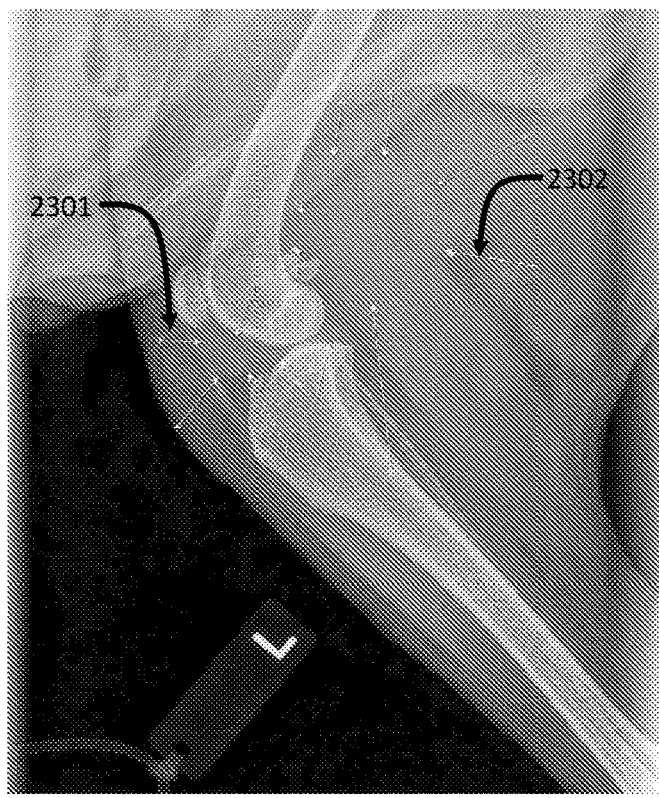
FIG. 23a is an original X-ray image of the same dog's leg as imaged in FIG. 22a, in accordance with at least one embodiment of the present invention.
Figure 23B:
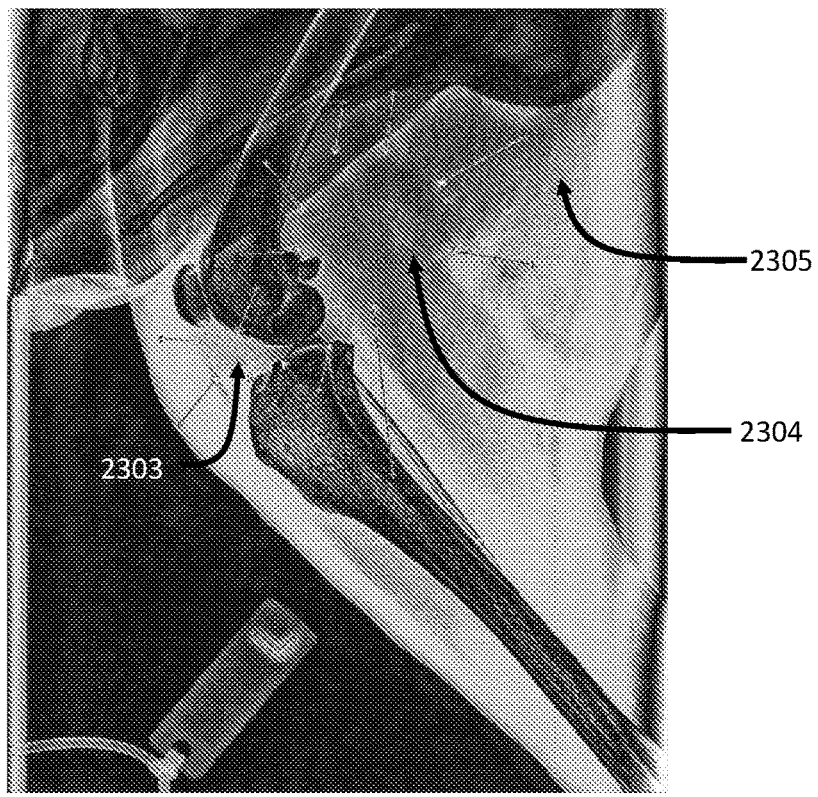
FIG. 23b depicts soft tissue sarcoma results after applying the same exemplary local micro-contrast convergence algorithmic sequence to the original image in FIG. 22a, in accordance with an exemplary embodiment of the present invention.

In contrast, FIG. 23b shows the extent of the sarcoma present in area 2303, area 2304, and area 2305, in the original X-ray in FIG. 23a, utilizing the LD algorithm. The LD algorithm visualizes the true extent of the sarcoma, beyond the area where the veterinarian originally indicated.

Multi-Algorithmic, Multi-Dimensional Computer Based Processes

Figure 24A:
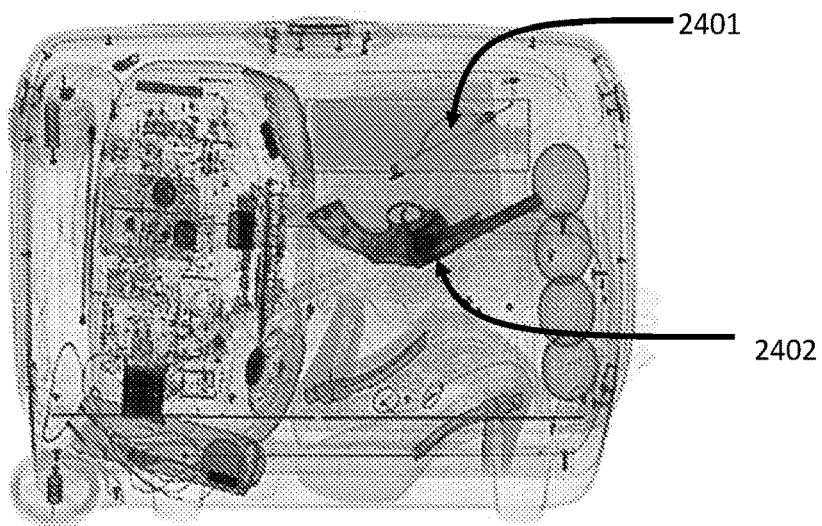
FIG. 24a is a resultant first-generation color image generated from a dual-energy X-ray system designed to scan baggage at airports and other security check points, in accordance with at least one embodiment of the present invention.

Embodiments of the invention, described herein, include methods that utilize a multi-algorithmic, multi-dimensional, computer-based process for the visualization and characterization of features of both biological and non-biological materials, in context, in images acquired from different imaging modalities. FIG. 24a is a resultant first-generation color image generated from a dual-energy X-ray system designed to scan baggage at airports and other security check points. The composite color image may be created by combining pixel densities of two X-ray images captured simultaneously, one for high energy and a second for low energy beams. By mathematically analyzing the two images and the relationships between their respective pixel values, the average atomic numbers of screened objects can be estimated to enable their classification into three categories: inorganic, organic and mixed materials. In FIG. 24a, organics 2401 are colored orange and inorganic materials 2402, with high average atomic numbers colored dark blue.

Figure 24B:
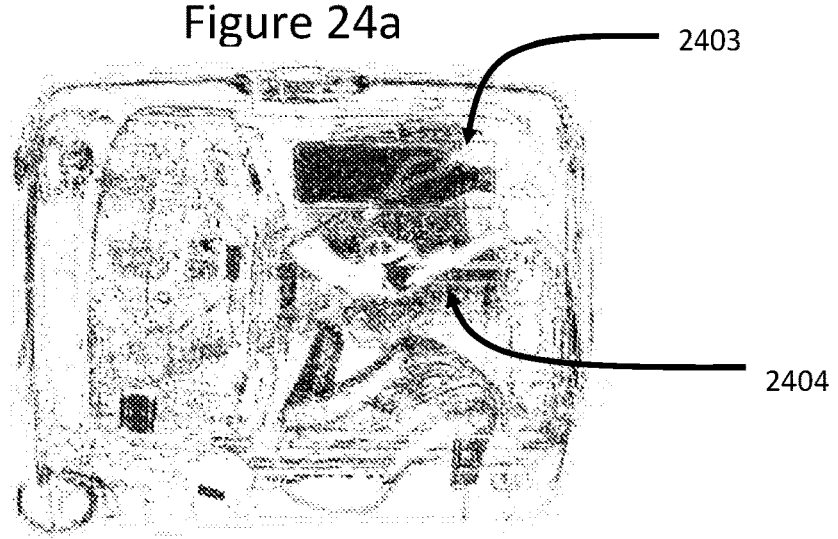
FIGS. 24b and 24c depict the application of the LD algorithm illustrated in FIG. 5i, in accordance with an exemplary embodiment of the present invention.
Figure 24C:
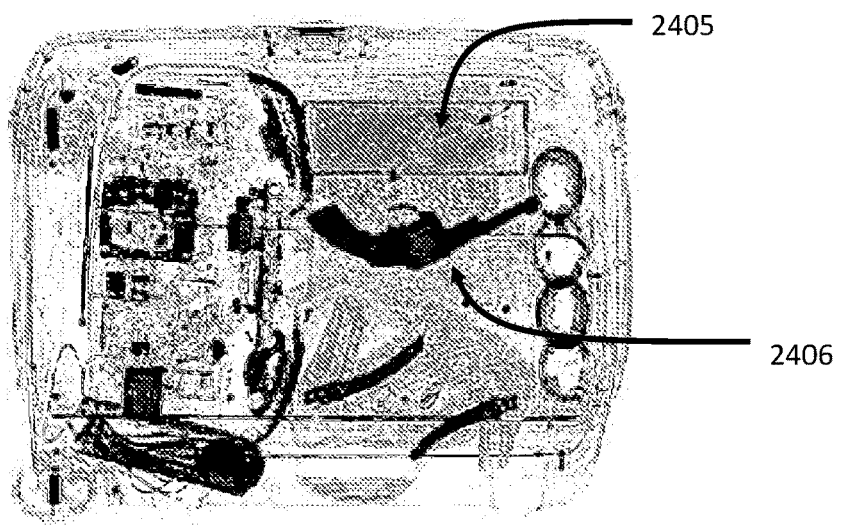

FIGS. 24a and 24b were created by applying the LD algorithm illustrated in FIG. 5i from step 501 to step 507 to the first-generation dual-energy X-ray shown in FIG. 24a. FIG. 24b and FIG. 24c were processed identically from step 501 to step 504. In step 506, the saturation values of both images were set to zero. With saturation values set to zero, the image appears as a grayscale and hue adjustments have no meaning. In step 506 as shown in FIG. 5i, the results shown in FIGS. 24b and 24c differ in the luminance value, settings were adjusted to transform each of six initial color values in FIG. 24a. By adjusting the color values in FIG. 24a, organic materials 2403 are visualized while deemphasizing other material including inorganic materials 2404. By again adjusting the color values in FIG. 24a, FIG. 24c shows inorganic materials 2406 while deemphasizing other material including the organic materials 2405.

A person familiar with image processing software may easily observe the real-time resultant variations of image transformation in HSL color space on their computer screen as luminance values of each color range are adjusted using a standard software-based slider bar or by typing different numerical values for each color range.

Embodiments of the invention exemplifying the methodology of the LMCC algorithms are detailed in FIGS. 4a through 10w.

Figure 27A:
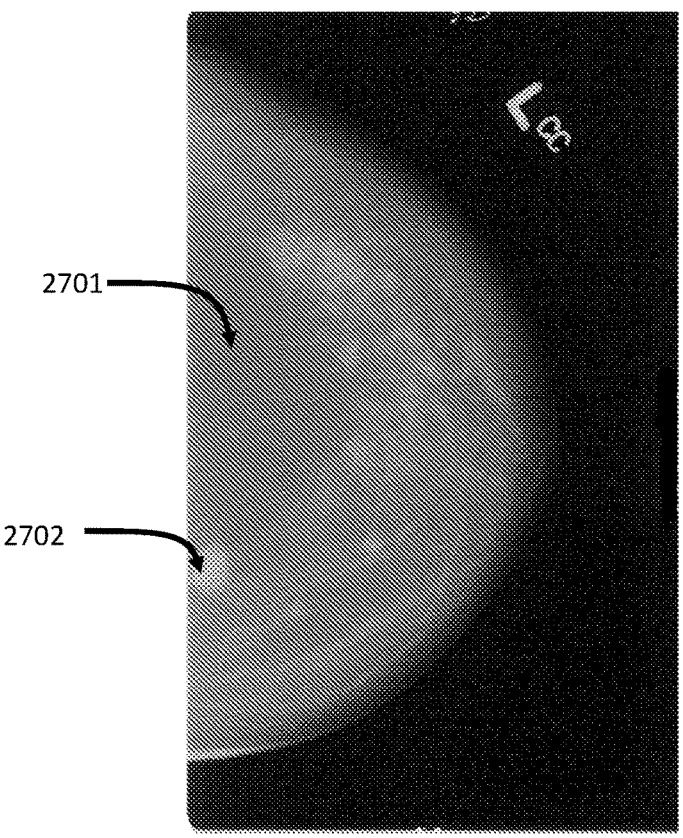
FIG. 27a is an original X-ray mammographic image showing the gray pattern of fatty breast tissue, in accordance with at least one embodiment of the present invention.

Embodiments of the invention regarding the CI algorithm provide visualizations that are designed to characterize tissue structures even when the details in an image (e.g., original mammogram) as shown in FIG. 27a are very close in grayscale tonal values as measured by a histogram between a lesion and the surrounding fatty tissue area. FIG. 27a is an original X-ray mammographic image showing the gray pattern of fatty breast tissue 2701. The pattern of the presence of a higher luminance value cancerous lesion 2702 is visible in the image against the gray pattern of the surrounding fatty breast tissue 2701. The histogram measures the luminance value of 155 (on a scale of 0 to 255) at the margins of the cancerous lesion 2702 while the adjacent area measures 145.

While some components of Imago's LMCC algorithmic sequences can distinctly express and differentiate tissue characteristics based on topology, others express fractal dimensions which can be expressed in non-integer values. Practically, this means that there are distinct "linear" patterns that reflect different tissue types.

Figure 25A:
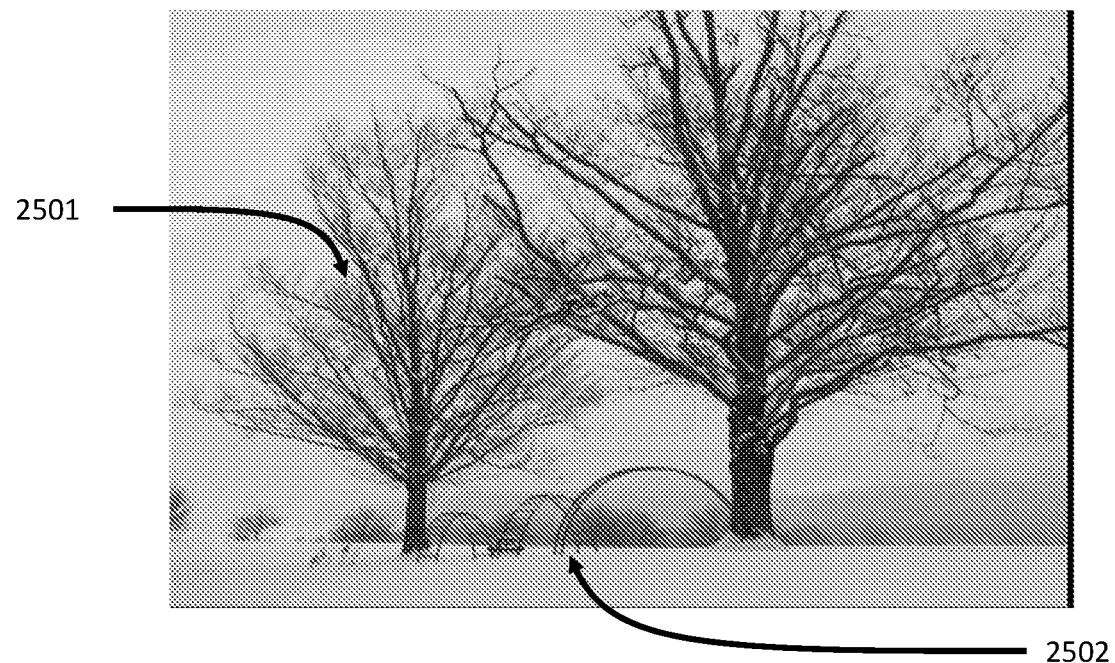
FIG. 25a is a digital photograph of a winter scene, in accordance with at least one embodiment of the present invention.
Figure 25B:
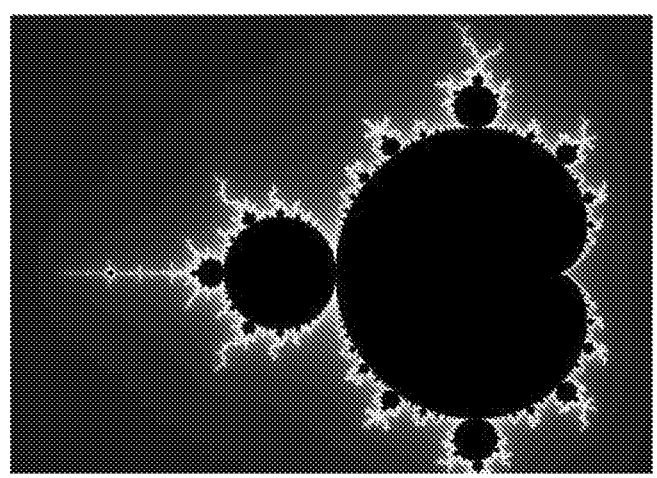
FIG. 25b is an example of a computer-generated pattern known as a Mandelbrot Set, in accordance with at least one embodiment of the present invention.

FIG. 25a is a digital photograph of a winter scene. Curved objects 2502 on the ground are of a playground that reflect the use of Euclidian-based geometry patterns (circles, squares, rectangles, spheres, etc.) in the design of many human made objects. The trees 2501 in the image reflect the fractal-geometry-based branching patterns inherent in biological and physical natural systems. FIG. 25b is an example of a computer-generated pattern known as a Mandelbrot Set. It is named after the mathematician who created the iterated mathematical function used to create the pattern.

Figure 26A:
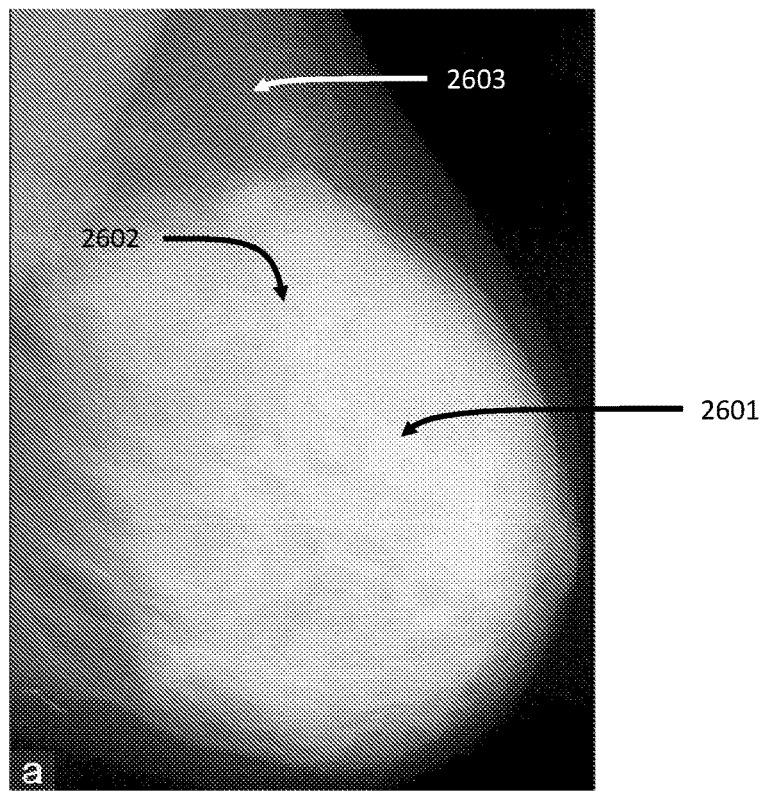
FIG. 26a is an original X-ray mammographic image showing the white pattern of dense breast tissue in accordance with at least one embodiment of the present invention.
Figure 26B:
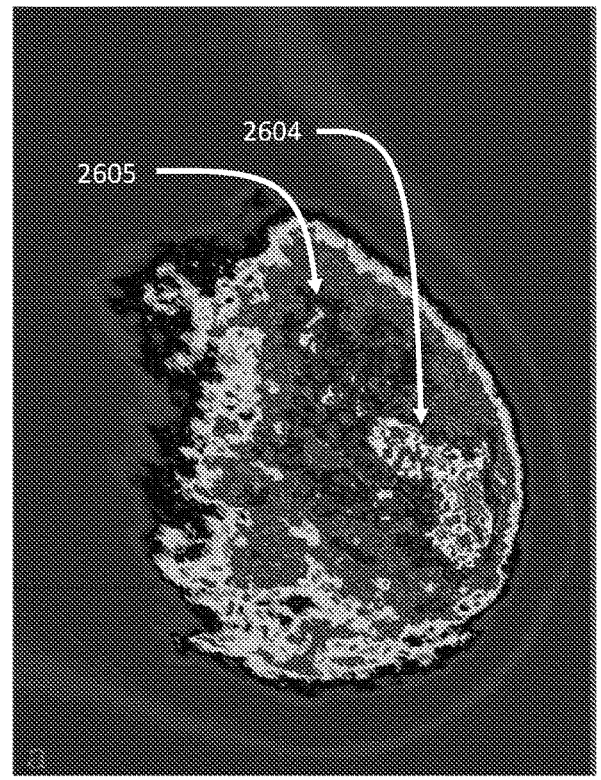
FIG. 26b shows the results after applying an exemplary local micro-contrast convergence algorithmic sequence to the original image in FIG. 26a, in accordance with at least one embodiment of the present invention.

Embodiments of the invention regarding the CI algorithm provide visualizations that are designed to characterize tissue structures even when the details in an image (e.g., original mammogram) as shown in FIG. 26a are obscured by the patient having dense breasts as defined by the American College of Radiology (ACR) density classification system. FIG. 26a is an original X-ray mammographic image showing the white pattern of dense breast tissue. Patterns of the presence of infiltrating ductal carcinoma, which are also white, is not visible in the image as presented. FIG. 26a depicts the location of underlying lesions that are not visible, 2601 and 2602 as well as an area of the breast that is declared fatty, 2603 as defined by the American College of Radiology (ACR) density classification system. FIG. 26b shows the results after applying an exemplary local micro-contrast convergence algorithmic (CI) sequence to the original image in FIG. 26a. FIG. 26b, depicts underlying lesions 2604 and 2605 depicted in red and gold colors.

Figure 27B:
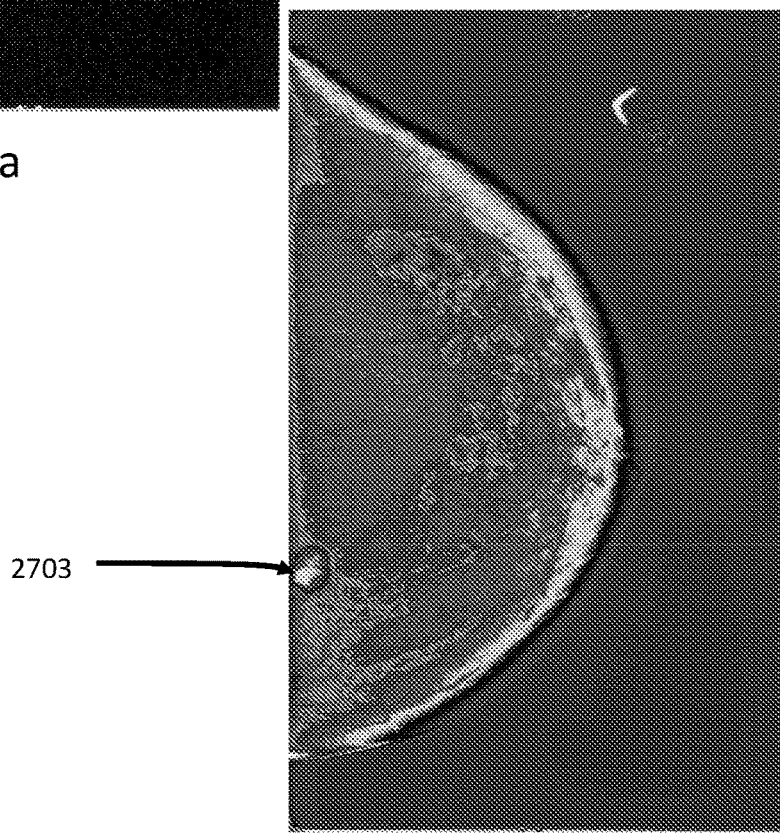
FIG. 27b shows the results after applying an exemplary local micro-contrast convergence algorithmic sequence to the original image in FIG. 27a, in accordance with at least one embodiment of the present invention.

FIG. 27b shows the results after applying an exemplary local micro-contrast convergence algorithmic (CI) sequence to the original image in FIG. 27a. The gold and red colored patterns 2703 visualize the cancerous lesion 2702 and show that it is separated from the surrounding fatty breast tissue shown in blue.

Embodiments of the invention regarding cancer detection rates in mammograms is to decrease the rate of false positives from those of current technologies.

Figure 28A:
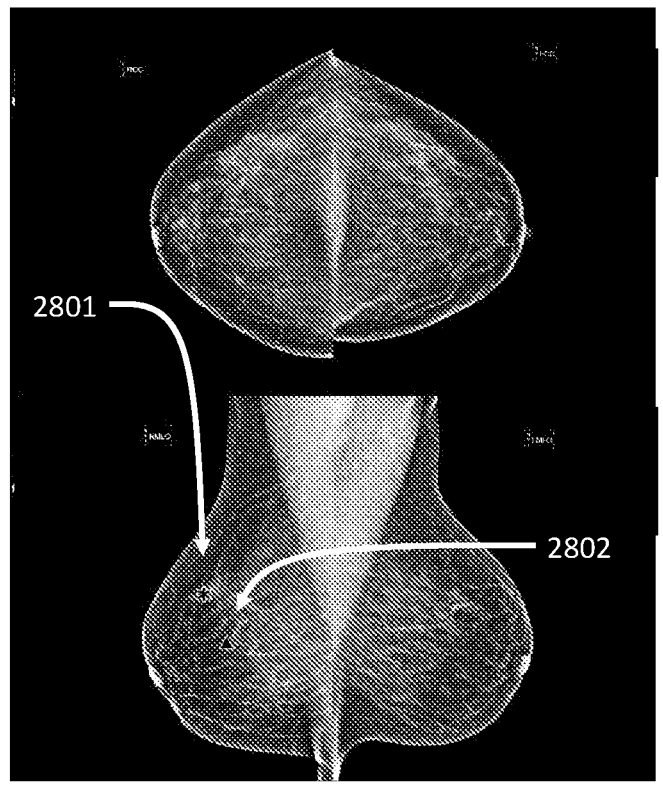
FIG. 28a shows a set of original X-ray mammographic images revealing both the left and right breast views, in accordance with at least one embodiment of the present invention.

FIG. 28a shows a set of original X-ray mammographic images revealing both the left and right breast views. The top view is a view from a cranial-caudal perspective. The lower view is from a medial lateral oblique perspective. Two marks placed on the lower left image (right medial lateral oblique view) were automatically generated and marked as possible abnormalities 2801 and 2802 by computer aided detection (CAD) software used in radiology today. Follow up procedures determined that this breast was normal and did not have any pathology. Both of the possible abnormalities 2801 and 2802 therefore are false positives. CAD is known to have a very high rate of false positives where marks are placed on a mammogram where there is no abnormality or pathology.

Figure 28B:
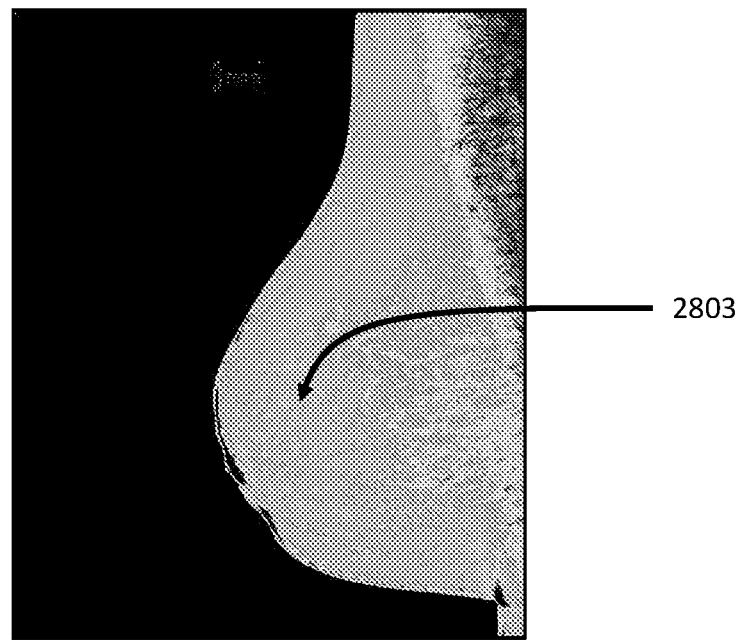
FIG. 28b shows the results after applying an exemplary local micro-contrast convergence algorithmic sequence to the original lower left image (Right medial lateral oblique view) in FIG. 28a, in accordance with at least one embodiment of the present invention.

FIG. 28b shows the results after applying an exemplary local micro-contrast convergence algorithmic (RF) sequence to the original lower left image (right medial lateral oblique view) in FIG. 28a. The LMCC algorithmic RF, FIG. 28b shows no pattern of abnormality shown by area 2803. The view does not require placing marks on the image since clinicians can readily view the patterns of all tissues, including those of normal and abnormal tissues. The multi-dimensional views created with the LMCC approach allows the clinicians to utilize their expertise and experience to more fully interpret the mammographic images and eliminate the need for many additional, but unnecessary, expensive, and sometimes painful procedures for the patient.

Embodiments of the invention regarding the CI algorithm provide visualizations as shown in FIG. 29b, that are designed to characterize tissue structures even when the details in an image (e.g., original mammogram) as shown in FIG. 29a are very close in grayscale tonal values between a lesion and the similar surrounding tissue area.

FIG. 29a is an original X-ray mammographic image. The patient was initially told that she did not have any benign or cancerous lesions. Additional testing with ultrasound and contrast-enhanced MM did not reveal any abnormalities.

Pathology analysis of her breast tissue after she decided to have a mastectomy indicated the presence of Atypical Hyperplasia transforming into Ductal Carcinoma in Situ (DCIS) spiculated type.

FIG. 29b shows the results after applying an exemplary local micro-contrast convergence algorithmic (CI) sequence to the original mammogram in FIG. 29a. Lesion 2901 is depicted in gold and red colors while the surrounding area is purple and blue. Pathology confirms the presence of the lesion 2901.

Figure 29C:
FIG. 29c is close up view of the lower left section of the original mammographic image shown in FIG. 29a, in accordance with at least one embodiment of the present invention.
Figure 29D:
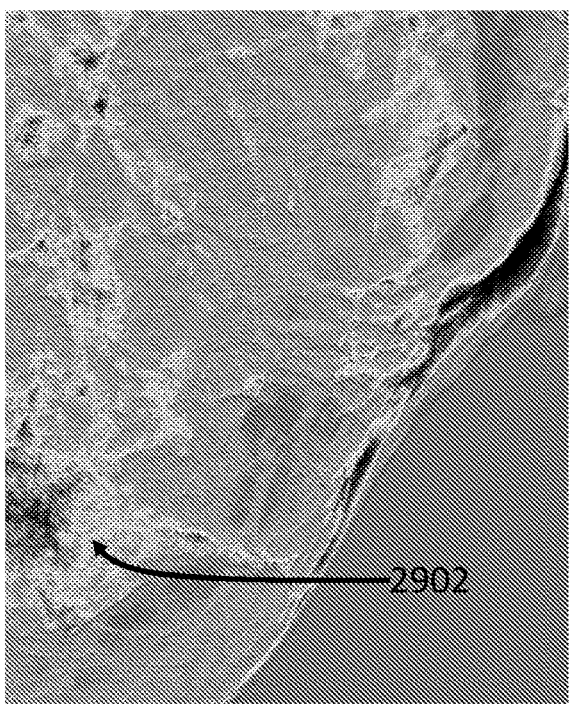
FIGS. 29d to 29f shows the results after applying an exemplary local micro-contrast convergence algorithmic sequence to the close up of the original mammogram in FIG. 29c, in accordance with at least one embodiment of the present invention.
Figure 29E:
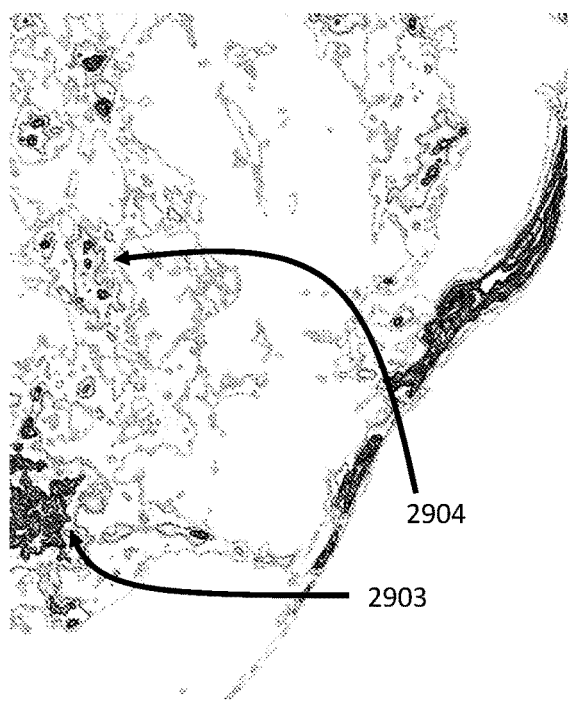
Figure 29F:
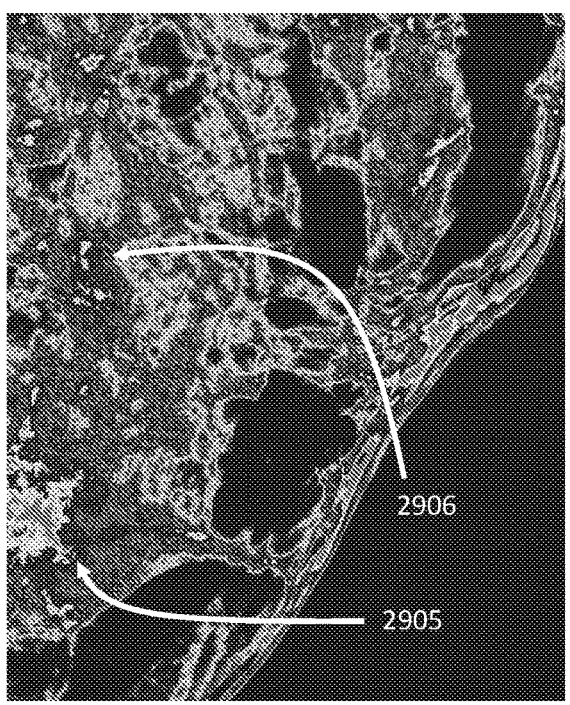

FIG. 29c is close up view of the lower left section of the original mammographic image shown in FIG. 29a. FIGS. 29d shows the results after applying an exemplary local micro-contrast convergence algorithmic (RF) sequence to the close up of the original mammogram in FIG. 29c. Lesion 2902 is shown, separated visually from the surrounding area. FIGS. 29e shows the results after applying an exemplary local micro-contrast convergence algorithmic (CR) sequence to the close up of the original mammogram in FIG. 29c. Lesion 2903 is shown, separated visually from the surrounding area while a second lesion 2904 is shown in FIG. 29e. FIGS. 29f shows the results after applying an exemplary local micro-contrast convergence algorithmic (CI) sequence to the close up of the original mammogram in FIG. 29c. Lesion 2905 is shown, separated visually from the surrounding area, while lesion 2906 depicts a second lesion in FIG. 29f Pathology confirms the presence of lesions 2904 and 2906.

Embodiments of the invention regarding consistency of local micro-contrast convergence algorithms over a range of both human and animal health applications.

Figure 30A:
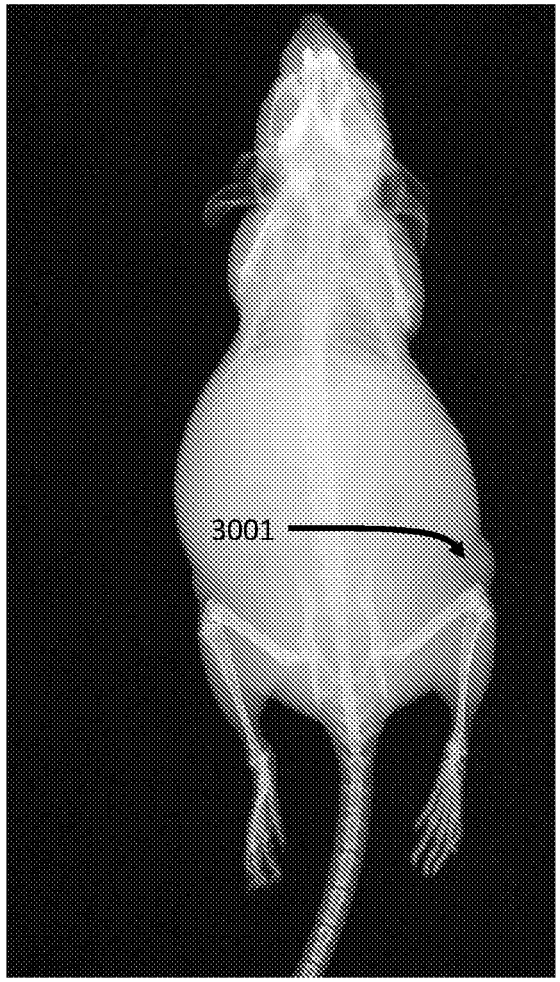
FIG. 30a is a first-generation X-ray image of a mouse known to have breast cancer on the right side of its body, in accordance with at least one embodiment of the present invention.

FIG. 30a is a first-generation X-ray image of a mouse known to have breast cancer on the right side of its body shown by tumor 3001.

Figure 30B:
FIG. 30b shows the results after applying an exemplary local micro-contrast convergence algorithmic sequence to the original X-ray in FIG. 30a, in accordance with at least one embodiment of the present invention.

FIG. 30b shows the results after applying an exemplary local micro-contrast convergence algorithmic (LD) sequence to the original X-ray in FIG. 30a.

FIG. 30c shows the results after applying an edge detection filter to FIG. 30b. Geometric patterns are created for all tissues i.e. bone, organs, and cancer. FIG. 30c shows fractal-like patterns 3002. Also shown are consistent, near parallel tissue structures 3003 on the left side of the mouse as well as a disruptive pattern 3004 on the right side, where the breast cancer was growing.

FIG. 30d is a close up of the left side of the X-ray of the mouse in FIG. 30c. The near parallel structure of the body tissue appears as laminar-like flow patterns 3005 consistent with normal tissue geometric patterns.

FIG. 30e is a close up of the right side of the mouse in FIG. 30c. The convoluted geometric patterns 3006 within the cancer tissue reflects the chaotic nature of cancer growth. This LMCC algorithm consistently expresses geometric patterns associated with the fractal dimensions of each tissue type in an image. Normal tissue patterns 3005 have straighter lines per square area than an identical square area with abnormal tissues 3006. Using this Euclidean-based analytic approach, a line is expressed as one dimension and an area is expressed as two dimensions. Applying the concepts of fractal geometry, the area of a one-dimension element in a two-dimension area can be used to quantify the degree to which a given tissue is either normal or contains pathology. Fractal patterns can be mapped for each tissue, or inorganic material, in a given imaging modality.

Consequently, normal tissue linear patterns might appear to occupy 60% of an area of an image (fractal dimension of 1.6) as compared with an abnormality with lines covering 83% of the same area size (fractal dimension of 1.83.)

Changes in the fractal dimensions of a tissue structure, in response to drug or immunotherapy procedures, may provide very early indications related to the progression or regression of cancer in response to cancer treatments.

Embodiments of the invention regarding consistency of local micro-contrast convergence algorithm performance extends over a wide range of sensor types and initiating energy sources.

Figure 31A:
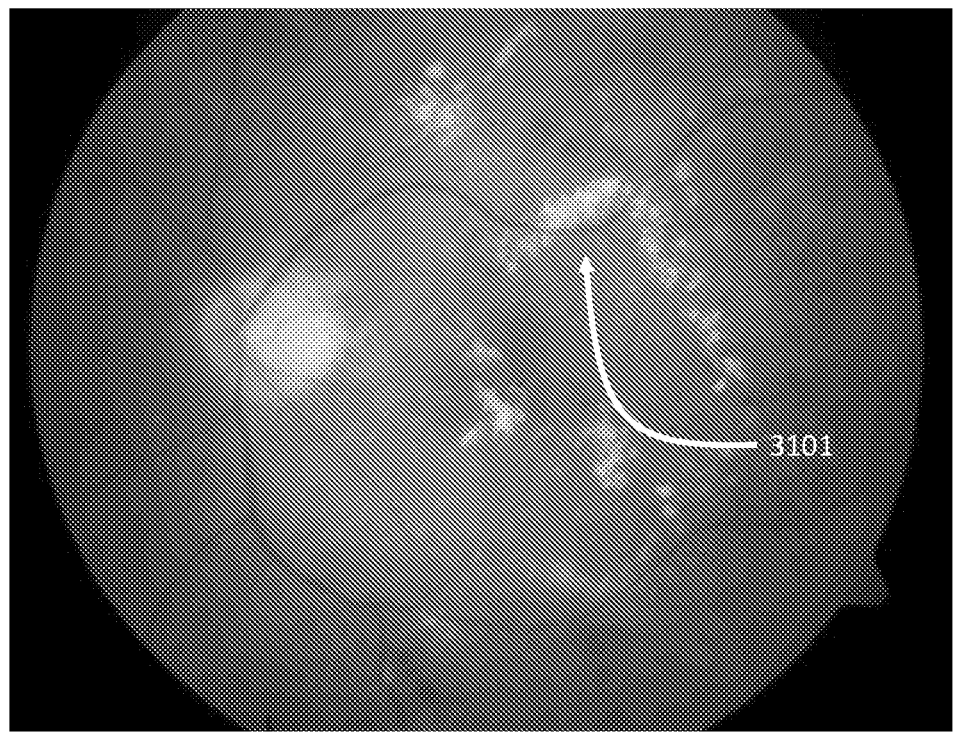
FIG. 31a is a first-generation color (fundus) image of the retina of an eye, in accordance with an exemplary embodiment of the present invention.

FIG. 31a is a first-generation color (fundus) image of the retina of an eye. These images are captured using visible light and some recording device that can be as compact as a camera in a cell phone. The retina in this image contains features such as the bright-appearing hard exudates pattern of diabetic retinopathy 3101. This is one of many abnormalities of the retina that are the result of having diabetes.

Figure 31B:
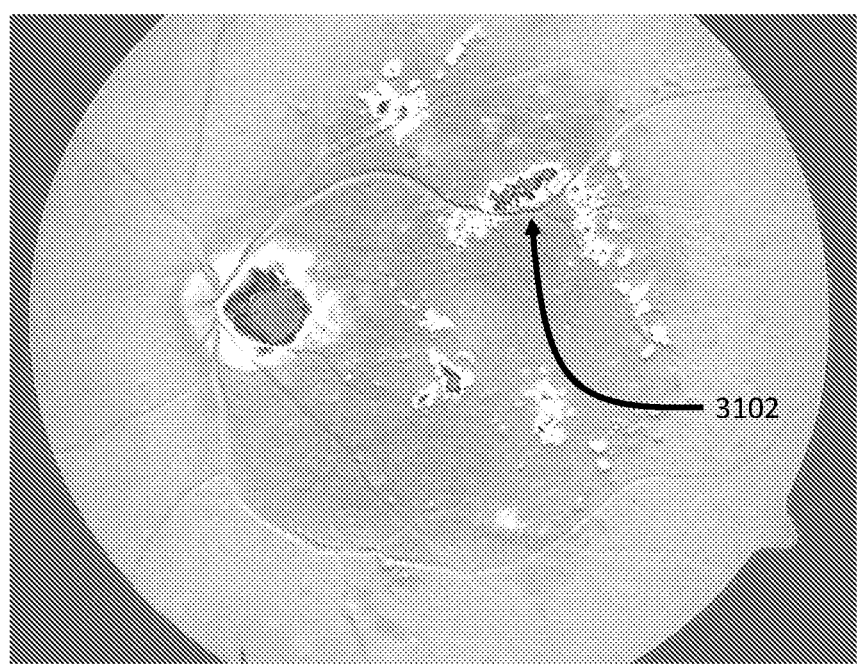
FIG. 31b shows the results after applying an exemplary local micro-contrast convergence algorithmic sequence to the original fundus image in FIG. 31a, in accordance with at least one embodiment of the present invention.

FIG. 31b shows the results after applying an exemplary local micro-contrast convergence algorithmic sequence to the original fundus image in FIG. 31a according to at least some embodiments of the invention and as further defined in FIG. 8u. This LMCC algorithm emphasizes patterns in an image and provides a "textured" appearance that helps separate materials/tissues in an image.

Embodiments of the invention regarding consistency of local micro-contrast convergence algorithm performance extends to use in additional modalities using multi-slice 3D imaging devices such as CT and MM scans.

Figure 32A:
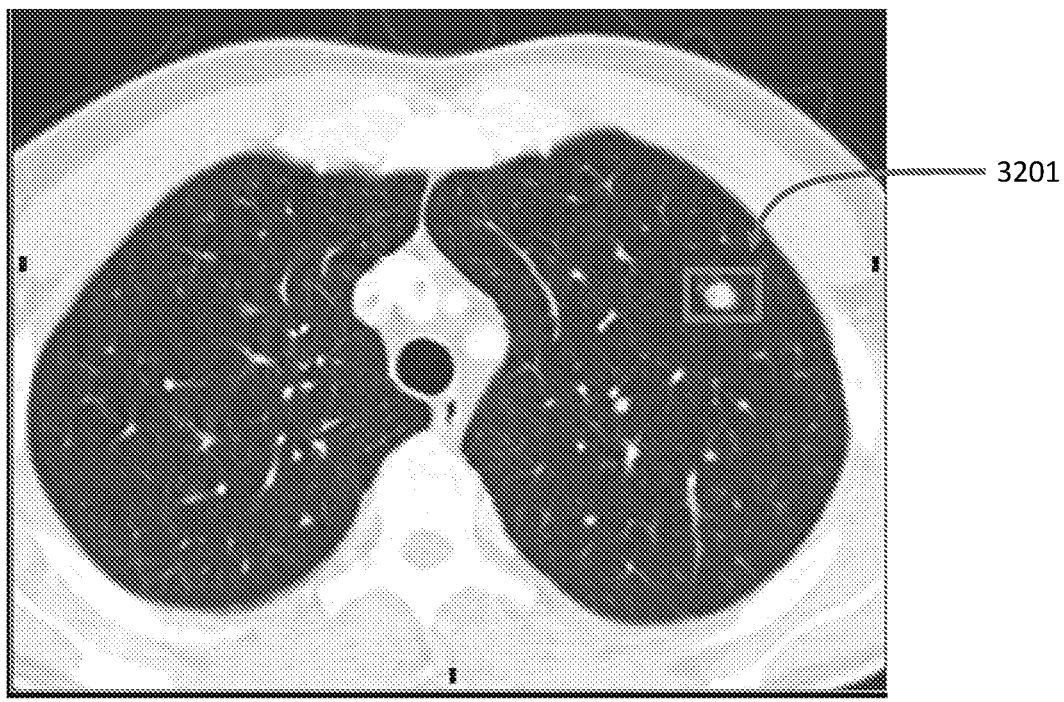
FIG. 32a is a first-generation CT scan of a patient with lung cancer, in accordance with at least one embodiment of the present invention.

FIG. 32a is a first-generation CT scan of a patient with lung cancer. The red rectangle 3201 indicates the location of a lung cancer nodule.

Figure 32B:
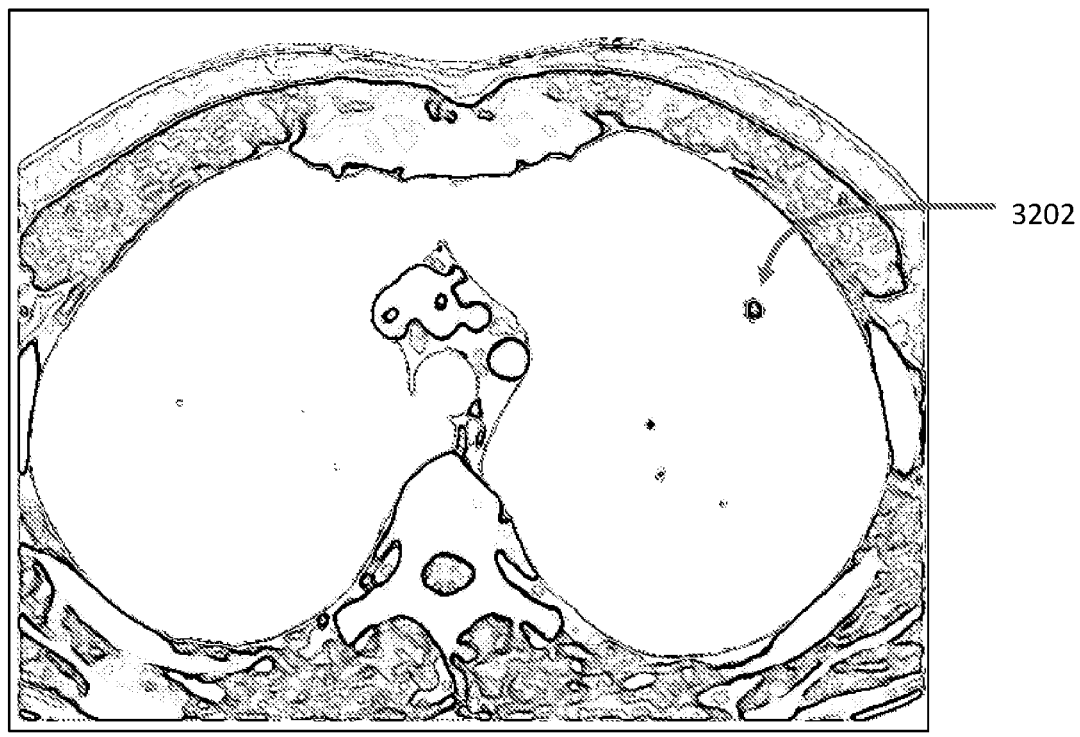
FIG. 32b shows the results after applying an exemplary local micro-contrast convergence algorithmic sequence to the original X-ray in FIG. 32a, in accordance with at least one embodiment of the present invention.

FIG. 32b shows the results after applying an exemplary local micro-contrast convergence algorithmic (CR) sequence to the original X-ray in FIG. 32a according to at least some embodiments of the invention and as further defined in FIG. 10w, then applying an edge detection filter. The lung cancer nodule 3202 remains as an object in the area of the lung while most of the other normal tissue structures such as blood vessels are no longer visible. Locating and characterizing lung cancer nodules in CT scans is a major problem for clinicians in the effort to determine the presence and extent of lung cancer in patients. Patterns within the lung nodules utilizing this LMCC algorithm can characterize structures, and their associated patterns within nodules, to provide geometric information to help distinguish normal from benign and benign from cancerous tissue structures.

Embodiments of the invention regarding consistency of local micro-contrast convergence algorithm performance can be applied to applications where the imaging modality is limited in its ability to differentiate tissue patterns when obscured by overlying or surrounding tissues such as tissues on top of tissues or for mapping the distribution and flow of fluids.

Figure 33A:
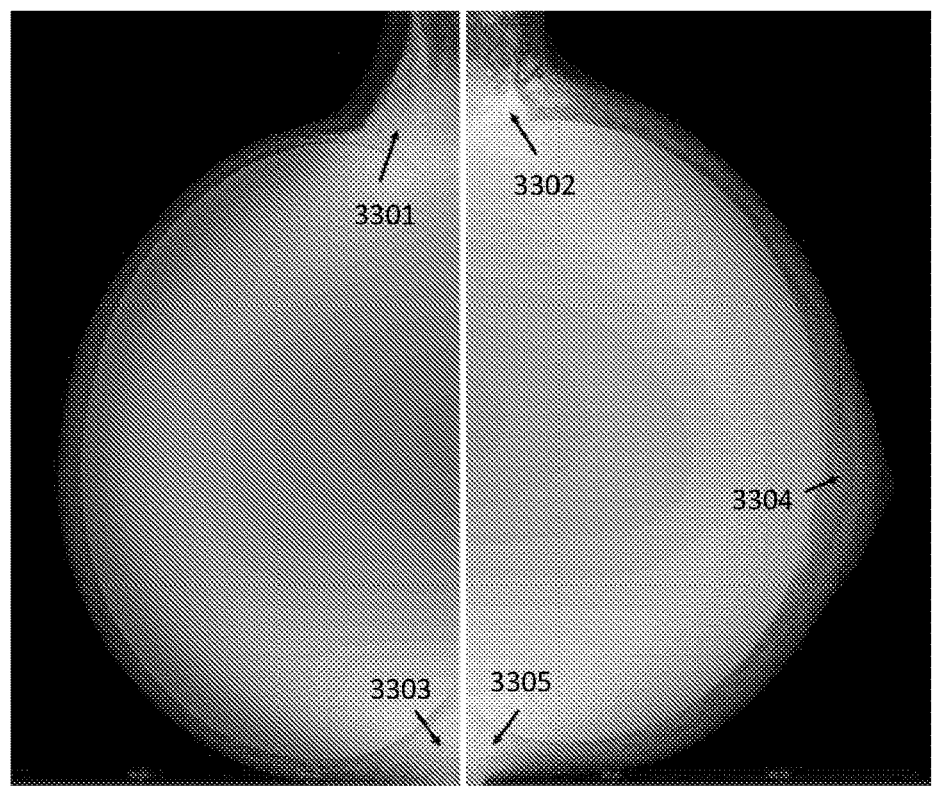
FIG. 33a shows a set of original X-ray mammographic images revealing both a left and right breast view, in accordance with at least one embodiment of the present invention.

FIG. 33a shows a set of original X-ray mammographic images revealing both a left and right breast view. The patient associated with this mammogram has had silicone breast implants. The implants were shown to be leaking into the surrounding breast tissue as seen at leaking areas 3301 to 3305. The high X-ray attenuating characteristics of the silicone make it difficult, and sometimes impossible, for clinicians to view the breast tissue, and possible presence of abnormalities hidden within the white opaque densities in the mammogram.

Figure 33B:
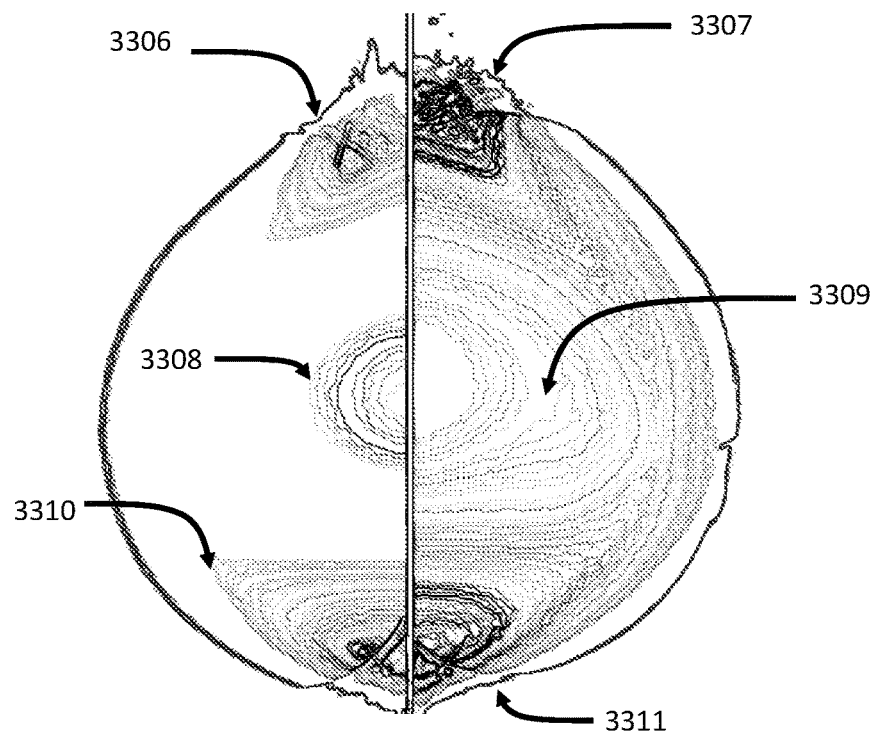
FIG. 33b shows the results after applying an exemplary local micro-contrast convergence algorithmic sequence to the original X-ray in FIG. 33a, in accordance with at least one embodiment of the present invention.

FIG. 33b shows the results after applying an exemplary local micro-contrast convergence algorithmic (CR) sequence to the original X-ray in FIG. 33a. This LMCC algorithm reveals the flow patterns 3306, 3307, 3310 and 3311 of the silicone material within the implant as a result of the leakage from the implant into the surrounding tissue.

There is no leakage indicated on the most lateral position of the right breast. The almost-circular pattern 3308 reveals the normal symmetry expected with a fluid that is no in dynamic flux. The silicone leakage 3304 as indicated in FIG. 33*a* has pulled fluid from within the interior of the left breast. The parabolic pattern 3309 of the breast shown in FIG. 33*b* indicates the flow outward of the silicone from within the implant.

Embodiments of the invention regarding consistency of local micro-contrast convergence algorithm performance can be applied to applications utilizing time-based imaging modalities used for functional analysis such as contrast-based MRI and a Positron Emission Tomography (PET) scans.

Figure 34A:
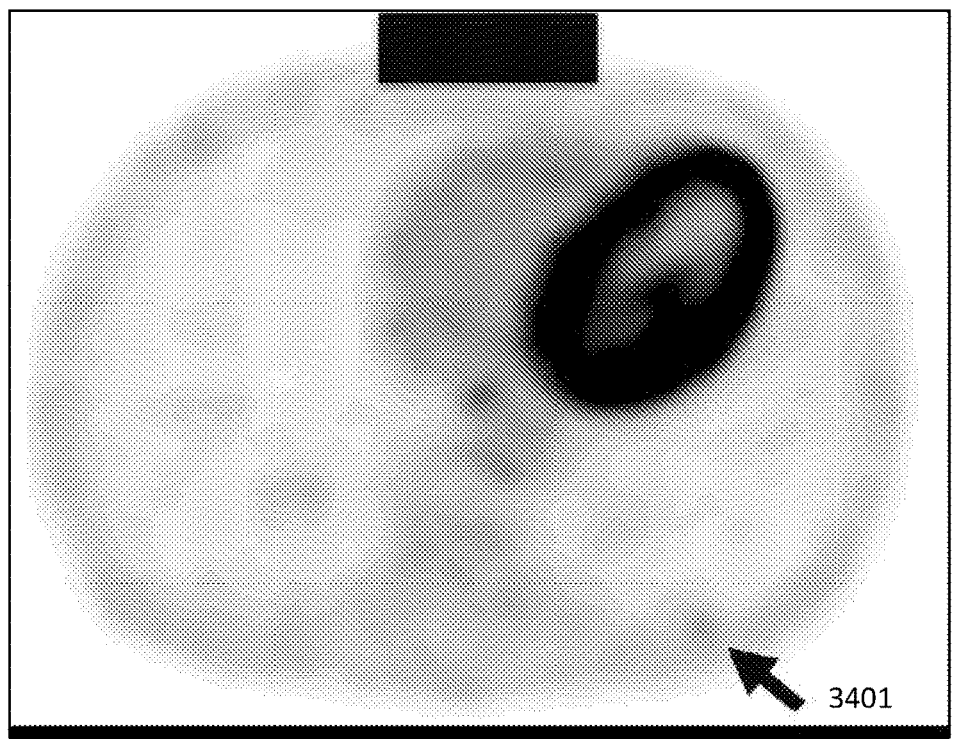
FIG. 34a shows a view of a patient's abdomen resulting from a Positron Emission Tomography (PET) exam, in accordance with at least one embodiment of the present invention.

FIG. 34*a* shows a view of a patient's abdomen resulting from a PET scan. A PET scan is useful in revealing or evaluating several conditions, including many cancers. The scan uses a special dye that has radioactive tracers. Abnormalities, such as cancers, can show up as spots in a captured image. This patient is known to have lung cancer with it at least one location indicated by a black arrow at possible lesion 3401.

Figure 34B:
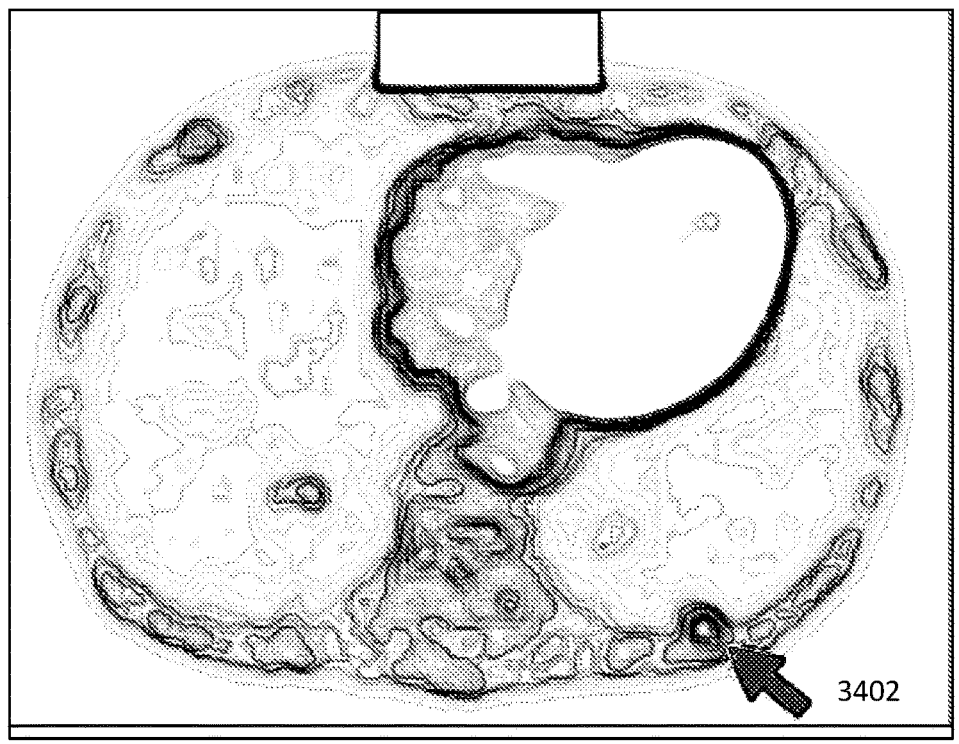
FIG. 34b shows the results after applying an exemplary local micro-contrast convergence algorithmic sequence to the original X-ray in FIG. 34a, in accordance with at least one embodiment of the present invention.

FIG. 34*b* shows the results after applying an exemplary local micro-contrast convergence algorithmic (CR) sequence to the original X-ray in FIG. 34*a*. The higher fractal dimensional disruptive pattern 3402 of the cancer is consistent with the pattern of cancer as seen in other tissues, using other imaging modalities as seen in FIGS. 30*d* and 32*b*.

Embodiments of the invention regarding consistency of local micro-contrast convergence algorithm performance can be applied to applications involving difficult to detect abnormalities in body parts where surgery has been the only diagnostic tool available to clinicians for applications in both human and animal medicine.

Figure 35A:
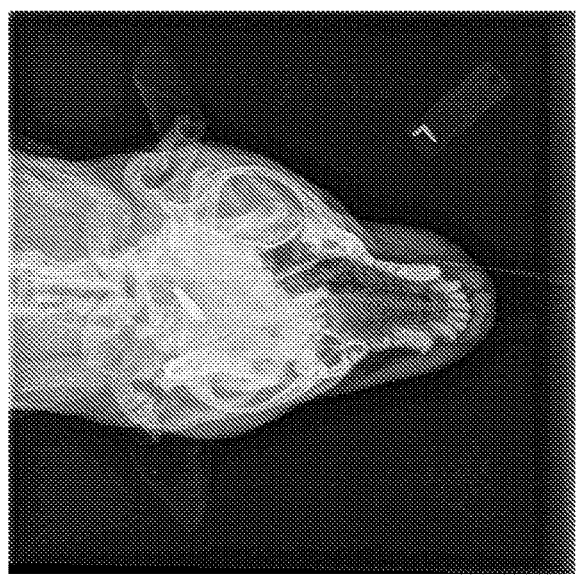
FIG. 35a is a first-generation X-ray image of the head of a dog, in accordance with at least one embodiment of the present invention.

FIG. 35*a* is a first-generation X-ray image of the head of a dog. The dog had recently developed what appeared to be sinus infections with accompanying nose bleeds.

Figure 35B:
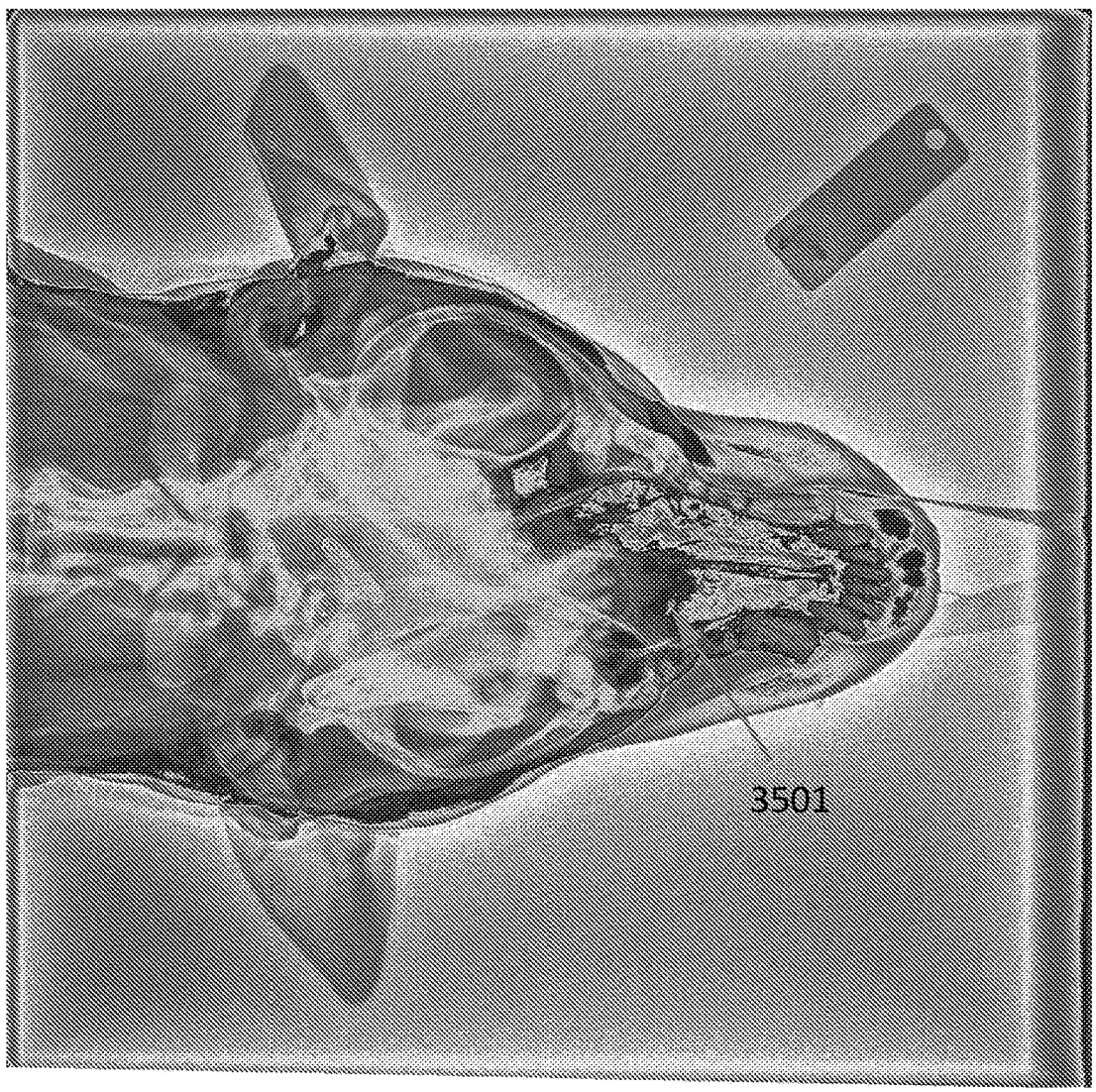
FIG. 35b was created by applying the LD algorithm illustrated in FIG. 35a, in accordance with at least one embodiment of the present invention.

FIG. 35*b* was created by applying the LD algorithm illustrated in FIG. 5*i* from step 501 to step 507 to the first-generation dual-energy X-ray shown in FIG. 35*a*. The end of the arrow pointing from lesion 3501 shows the presence of a nasal carcinoma. Normally, a veterinarian would perform exploratory surgery to identify the abnormality. This LMCC LD algorithm reveals both the presence and the extent of the cancer.

Embodiments of the local micro-contrast convergence algorithmic process can be employed in visualizing, characterizing, and analyzing a wide range of image types including those in scientific investigation in photo microscopy, material analysis in the aviation industry, and in astrophysics.

Figure 36A:
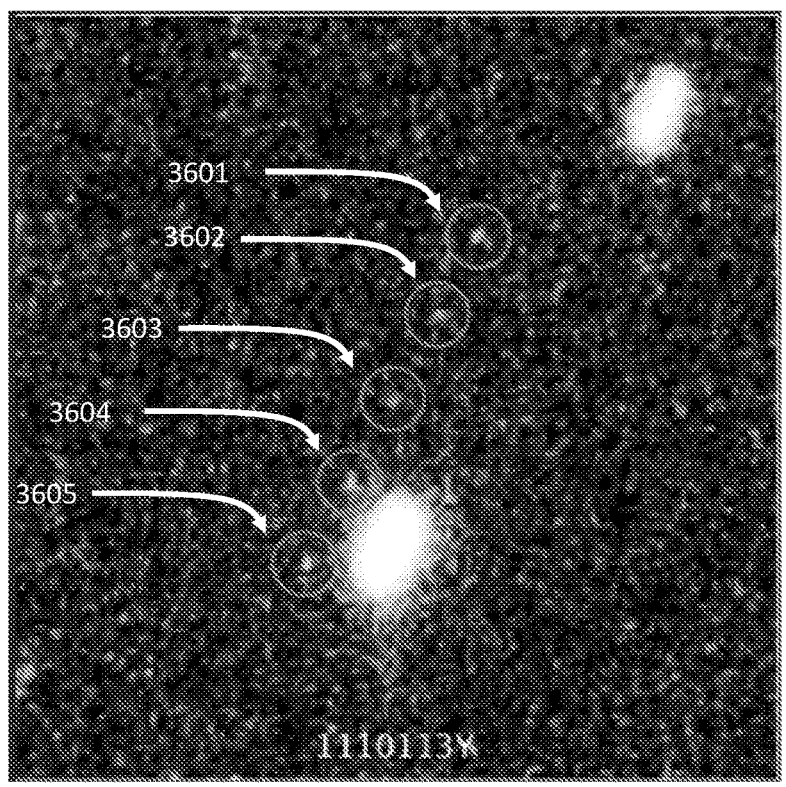
FIG. 36a is a set of multiple-exposure images created by the Hubble Space Telescope of a Kuiper Belt object 6.4 billion Km away from Earth, in accordance with at least one embodiment of the present invention.

FIG. 36*a* is a set of multiple-exposure images created by the Hubble Space Telescope of a Kuiper Belt Object (KBO) 6.4 billion Km away from Earth. The image was generated by the KBO Search Team. The circled white spots 3601 to 3605 show the transit of the object against the background star field over the multiple-exposure time periods.

Figure 36B:
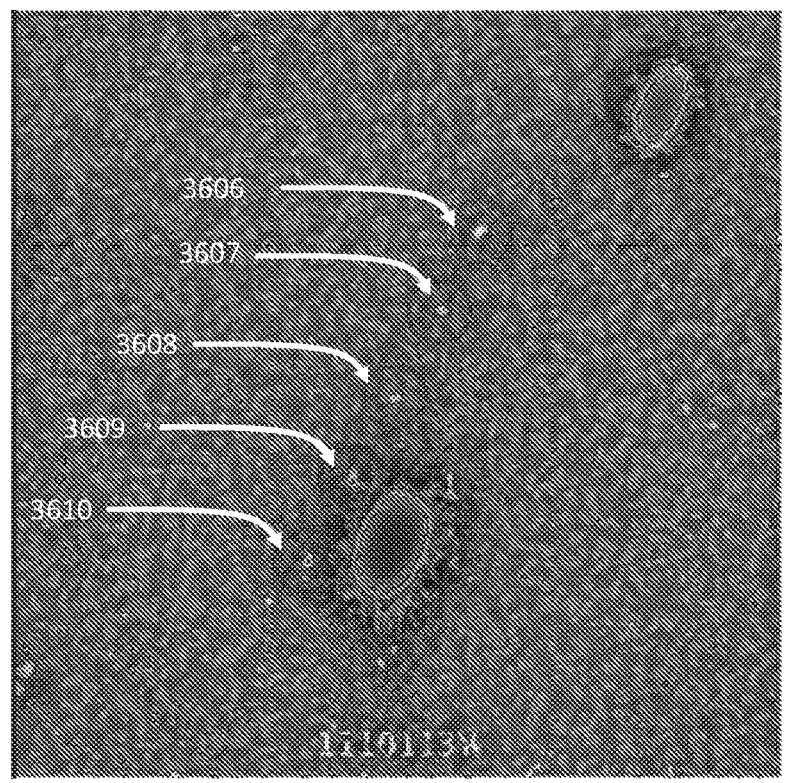
FIG. 36b shows the results after applying an exemplary local micro-contrast convergence algorithmic sequence to the original image in FIG. 36a, in accordance with at least one embodiment of the present invention.

FIG. 36*b* shows the results after applying an exemplary local micro-contrast convergence algorithmic sequence to the original image in FIG. 36*a* according to at least some embodiments of the invention. The LMCC algorithmic sequence first utilized the process defined in FIG. 4*k*. A second copy of the image shown in FIG. 36*a* was then processed using a high-pass filter. The two images were then merged where the lightest colors are subtracted from the darker colors. In the process, white inverts the base color and black produces no change. Finally, green and cyan colors are altered by having the image placed in HLS color space and desaturating those two tonal ranges. The result is to isolate the Kuiper Belt objects 3606 to 3610 visually from the rest of the small white objects.

Alternative Embodiments—Different Processing Combinations

While the preceding paragraphs describe different embodiments for image visualization of local micro-contrast convergence, one of ordinary skill in the art will appreciate that one or more of the processing steps performed in one embodiment may be applied in any order and/or to other embodiments, including, but not limited to: gamma level adjustment or leveling, convolution filtering, sharpening filters, smoothing filters, median filters, high-pass filters, low-pass filters, merging functions, image multiplication functions, image subtraction functions, image addition functions, image blending functions, wavelet functions, and image layering functions, among others described herein.

Alternative Embodiments—Different Modalities

Embodiments of the invention have applicability to a number of different fields, including, but not limited to: medical imaging (e.g., mammography, MRI, PET or CAT scans, ultrasound, 3-D Tomosynthesis), bomb detection, liquid explosive detection, satellite imaging, structural analysis, industrial, stress, quality control, weld and material analysis (e.g., checking for cracks or breaks in high-tension wires, airplane wings, pipes in nuclear power plants), printing standards analysis (e.g., money stamps), and forensics, among others. Thus, different imaging modalities (e.g., mammogram, x-ray, ultrasound, infra-red, ultra-violet, MRI, CT scans, PET scans, grayscale, color, visible light (e.g., photo microscopy), laser scans) may be processed using different visualization methodologies described herein. One of ordinary skill in the art would also appreciate that embodiments of the invention are not limited to the fields described herein, but instead are applicable to any field requiring pixel data analysis in an image, regardless of the imaging modality or energy source generating the images.

Alternative Embodiments—Cancer/Diseases

Embodiments of the invention have applicability to visualizing, characterizing, and detecting several different cancers including, but not limited to: prostate, kidney, liver, bone, lung, brain, and skin of both humans and animals. One of ordinary skill in the art would also appreciate that embodiments of the invention are not limited to the cancers described herein, but instead are applicable to other similar cancers.

Embodiments of the invention have applicability to detecting several different diseases including, but not limited to: cardiovascular diseases, detection of Alzheimer's disease in retinal scans, diseases of the eye, multiple sclerosis lesion mapping, photo microscopy. One of ordinary skill in the art would also appreciate that embodiments of the invention are not limited to the diseases described herein, but instead are applicable to other similar diseases.

Embodiments for improving false positive/false negative rates

Applying one or more of the micro-contrast convergence algorithms, described herein in medical applications for example, produce an image visualization that facilitates users (e.g., radiologists) with detecting structures of interest (e.g., cancer). As a result, the false positive rates and false negative rates are considerably reduced.

In some embodiments, the false positive rate for breast cancer detection in a mammogram image, where the breast includes at least a portion of dense breast tissue, over a series of 100 trials, is less than 10% as determined by a physician. In some embodiments, the false positive rate for breast cancer detection in a mammogram image, where the breast includes at least a portion of dense breast tissue, over a series of 100 trials, is less than 5% as determined by a physician. In some embodiments, the false positive rate for breast cancer detection in a mammogram image, where the breast includes at least a portion of dense breast tissue, over a series of 100 trials, is less than 1% as determined by a physician.

In some embodiments, the false negative rate for breast cancer detection in a mammogram image, where the breast includes at least a portion of dense breast tissue, over a series of 100 trials, is less than 60% as determined by a physician. In some embodiments, the false negative rate for breast cancer detection in a mammogram image, where the breast includes at least a portion of dense breast tissue, over a series of 100 trials, is less than 50% as determined by a physician. In some embodiments, the false negative rate for breast cancer detection in a mammogram image, where the breast includes at least a portion of dense breast tissue, over a series of 100 trials, is less than 45% as determined by a physician. In some embodiments, the false negative rate for breast cancer detection in a mammogram image, where the breast includes at least a portion of dense breast tissue, over a series of 100 trials, is less than 40% as determined by a physician. In some embodiments, the false negative rate for breast cancer detection in a mammogram image, where the breast includes at least a portion of dense breast tissue, over a series of 100 trials, is less than 35% as determined by a physician. In some embodiments, the false negative rate for breast cancer detection in a mammogram image, where the breast includes at least a portion of dense breast tissue, over a series of 100 trials, is less than 30% as determined by a physician. In some embodiments, the false negative rate for breast cancer detection in a mammogram image, where the breast includes at least a portion of dense breast tissue, over a series of 100 trials, is less than 25% as determined by a physician. In some embodiments, the false negative rate for breast cancer detection in a mammogram image, where the breast includes at least a portion of dense breast tissue, over a series of 100 trials, is less than 20% as determined by a physician. In some embodiments, the false negative rate for breast cancer detection in a mammogram image, where the breast includes at least a portion of dense breast tissue, over a series of 100 trials, is less than 15% as determined by a physician. In some embodiments, the false negative rate for breast cancer detection in a mammogram image, where the breast includes at least a portion of dense breast tissue, over a series of 100 trials, is less than 10% as determined by a physician. In some embodiments, the false negative rate for breast cancer detection in a mammogram image, where the breast includes at least a portion of dense breast tissue, over a series of 100 trials, is less than 5% as determined by a physician. In some embodiments, the false negative rate for breast cancer detection in a mammogram image, where the breast includes at least a portion of dense breast tissue, over a series of 100 trials, is less than 4% as determined by a physician. In some embodiments, the false negative rate for breast cancer detection in a mammogram image, where the breast includes at least a portion of dense breast tissue, over a series of 100 trials, is less than 3% as determined by a physician. In some embodiments, the false negative rate for breast cancer detection in a mammogram image, where the breast includes at least a portion of dense breast tissue, over a series of 100 trials, is less than 2% as determined by a physician. In some embodiments, the false negative rate for breast cancer detection in a mammogram image, where the breast includes at least a portion of dense breast tissue, over a series of 100 trials, is less than 1% as determined by a physician.

In some embodiments, the false negative rate for breast cancer detection in a mammogram image, where the breast includes normal breast tissue, over a series of 100 trials, is less than 16% as determined by a physician. In some embodiments, the false negative rate for breast cancer detection in a mammogram image, where the breast is normal breast tissue, over a series of 100 trials, is less than 15% as determined by a physician. In some embodiments, the false negative rate for breast cancer detection in a mammogram image, where the breast includes normal breast tissue, over a series of 100 trials, is less than 10% as determined by a physician. In some embodiments, the false negative rate for breast cancer detection in a mammogram image, where the breast includes normal breast tissue, over a series of 100 trials, is less than 5% as determined by a physician. In some embodiments, the false negative rate for breast cancer detection in a mammogram image, where the breast includes normal breast tissue, over a series of 100 trials, is less than 1% as determined by a physician.

Feature Extraction

By implementing embodiments of the invention, images are generated that visualize and characterize tissue structures in an enhanced manner that improves feature identification (e.g., by radiologists).

In some embodiments, processor 252 may implement one or more computer aided detection (CAD) techniques on one or more generated image visualizations to identify cancerous structures. Large-scale pattern recognition systems applicable to millions of informational features may include such features first, second, and third order image analysis any may employ image comparisons (e.g., between a known cancerous structure and portions of the image visualizations).

The process employed in this application using local micro-contrast convergence algorithmic approaches causes such tissue type in an image, such as a mammogram, to assume characteristics color and grayscale properties that uniquely characterize the tissues and their boundaries, making feature identification and extraction highly effective for accurate identification. These properties include, but are not limited to: morphology, geometry, color, texture, relationships among different tissue structures (such as correlating the presence of lesions with microcalcifications in breast tissue), shapes of lesion boundaries, presence of spiculations, edge-gradients, cumulative edge-gradient distributions, architectural distortions, distribution of colors within lesions, contrast, temporal stability (changes between mammographic exams), and correlation of features between different views (multiple view correlation between CC and MLO mammographic image views).

The Machine Learning process in the breast cancer detection domain begins by extracting features correlated with disease such as benign cysts, fibro adenomas, carcinomas, and invasive cancers. A training set of images is used to develop criteria for comparison between cancer and non-cancer areas of a mammogram.

Relevant features are extracted as clusters of pixel luminance and color values that have resulted in local micro-contrast convergence process tissue characterization patterns from a given coordinate area in each processed image. A multiplicity of local micro-contrast convergence processed images can be analyzed and features extracted from each of the separate images that have been created through one or more visualization algorithmic sequences, described herein. All processed images being examined may be superimposed so there is complete registration in areas of interest among the different processed images.

In some embodiments, processor 252 may generate one or more non-linear transfer functions to apply to an image to identify a feature of interest. In these embodiments, processor 252 may run different trials, with a different set of local micro-contrast convergence transfer functions used for each trial. In some embodiments, the local micro-contrast convergence transfer functions may be generated at random. In some embodiments, the local micro-contrast convergence transfer functions are generated based on default functions (e.g., trigonometric functions). Examples for generating local micro-contrast convergence transfer functions based on default functions are illustrated in FIG. 2*a*.

The range of luminance values available for mapping luminance values in this coordinate plot is unbounded. As a result of the trials, processor 252 may select a preferred set of non-linear transfer functions to apply to an image based on the lowest probability of a false positive and/or false negative.

Feature analysis may include high separability feature extraction (HSFE) from data, basing on both standard and advanced characteristics of images and time series, including: Co-Occurrences, Gabor, SIFT, LBP, Histograms of Oriented Gradients, Random Ferns and Hough Forests.

Machine learning, data mining, and statistical modeling techniques can be applied for real-time object recognition and localization in the processed images using such processes as Adaboost, genetic programming, support vector machines, neural networks, global optimization, and learning vector quantization.

There is no theoretical limit to the number of features that can be extracted or the number of correlations that can be created among them. Algorithmic development can be employed for Big Data applications using R, Pig, Storm, MySQL, MongoDB, and Hadoop.

In some embodiments, the functions utilized within a local micro-contrast convergence algorithmic sequence can be used to locate abnormalities, guide interventional procedures, tissue excisions, and monitor patient progress following the procedure thereby improving correct diagnoses by the clinician for the patient and improving prognoses for the patient. In one embodiment, patient monitoring can be accomplished by applying the local micro-contrast convergence algorithms to images taken of a patient undergoing cancer treatment to assist clinicians in determining if the chemo/radiation/hormone therapy regimes are effective, and if not, then change the procedure and perhaps move to surgical intervention. In another embodiment, multiple images generated in a stereotactic biopsy procedure can be processed by the local micro-contrast convergence algorithms to better identify the core of a cancerous lesion and be marked by the clinician for more precise 3-D location of the lesion and extraction of tissues.

In some embodiments, the functions utilized within a local micro-contrast convergence algorithmic sequence can be used to monitor the effectiveness of interventional medical procedures such as the use of nanotechnology. The capability of the local micro-contrast convergence algorithms to visualize and characterize abnormalities at very small sizes, can assist clinicians in first finding all the abnormalities (cancers), then monitor changes in not only the large lesions but the small lesions as well. Because the local micro-contrast convergence algorithms are effective at visualizing and characterizing cancer in different body parts using different imaging modalities, they can be employed to identify and characterize the distribution of lesions in other parts of the body where the cancer may have metastasized.

In some embodiments, the functions utilized within a local micro-contrast convergence algorithmic sequence can be used to monitor the effectiveness of interventional medical procedures, such as the use of nanotechnology and effectiveness of immunotherapy regimes. The effectiveness of measuring the effectiveness of immunotherapy regimes can be challenging because most therapies utilize the injection of drugs or materials systemically where, only a small percentage of the drug may reach the cancer area. The local micro-contrast convergence algorithms can reveal minute changes over time at the boundaries and internal structures of the cancer. Because the local micro-contrast convergence algorithms can characterize all tissues, not just the abnormalities, changes in the tumor micro environment (TME) surrounding the lesion can also be revealed to show either tumor shrinkage or a continuation of cancer growth into the surrounding tissues.

In some embodiments, the functions utilized within a local micro-contrast convergence algorithmic sequence can be used to assess the extent of cancer in breast tissue excision procedures to determine the extent of the cancer in a mammogram of the tissue before the tissue is examined microscopically for pathology. The boundaries of cancerous lesions are well defined in known patterns utilizing the local micro-contrast convergence algorithms and can be employed during the surgical procedure when the excised tissue is X-rayed and examined by the clinician after processing the image with local micro-contrast convergence algorithms.

In some embodiments, the functions utilized within a local micro-contrast convergence algorithmic sequence can be utilized to monitor changes in small lesions in medical images that may be difficult to see visually without processing with local micro-contrast convergence algorithms.

In some embodiments, the functions utilized within a local micro-contrast convergence algorithmic sequence can be used to visualize and characterize density and internal patterns within and at the boundaries of tissues and monitor changes of tissue growth when incubated in cultures.

In some embodiments, the functions utilized within a local micro-contrast convergence algorithmic sequence can form the basis for feature extraction of tissues/materials for machine learning and artificial intelligence by providing distinctive margins and tissue structure characterizations that are unique properties for objects of interest.

In a further embodiment, initial steps in a local micro-contrast convergence algorithmic sequence can characterize and visualize all materials/tissues, while subsequent steps in the algorithm can subtract out non-diagnostic tissues/materials to provide improved visual discrimination to important diagnostic areas of the image such as performing fat subtraction in a mammogram to further reveal microcalcifications in the image.

In a further embodiment, the functions utilized within multiple local micro-contrast convergence algorithmic sequences can create multiple visualizations expressing different characteristics in both the spatial and frequency domains of the same object of interest to achieve higher rates of sensitivity and specificity in machine learning applications.

In a further embodiment, the functions utilized within multiple local micro-contrast convergence algorithmic sequences can create multiple visualizations expressing different characteristics of the same object of interest with images from different imaging modalities to achieve higher rates of sensitivity and specificity in machine learning applications.

In at least one embodiment, there is included one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A method of visualizing and characterizing a feature comprising self-similar patterns in an image of an object, the method comprising:
   applying a first local micro-contrast convergence algorithm to a first image to produce a second image that is separate and distinct from the first image, wherein the second image includes a visualization of the self-similar patterns of the feature within a context of the object in the image,
   wherein applying the first local micro-contrast convergence algorithm includes applying one or more non-linear discontinuous transfer functions to the first image,
   wherein applying one or more non-linear discontinuous transfer functions to the first image includes utilizing one or more grayscale or color profile look up tables representative of the one or more non-linear discontinuous transfer functions.

2. The method of claim 1, further comprising:
   applying a second local micro-contrast convergence algorithm, separate and distinct from the first local micro-contrast convergence algorithm, to the first image to produce a third image that is separate and distinct from the first image and the second image.

3. The method of claim 2, further comprising:
   sequentially applying a third local micro-contrast convergence algorithm to the third image to generate a fourth image.

4. The method of claim 3, further comprising:
   combining one or more of the first, second, third or fourth images to produce a fifth image that is separate and distinct from the first, second, third or fourth images.

5. The method of claim 2, wherein the first image is a grayscale image having pixel values, the method further comprising:
   replicating the pixel values of the grayscale image in a first multi-dimensional color space where each dimension of the first multi-dimensional color space is a replicate of the pixel values of the grayscale image.

6. The method of claim 5, wherein the first multi-dimensional color space includes four dimensions including four different components: luminance, red, green, and blue, and wherein the second image is an RGB multi-dimensional color space including luminance and three different color dimensions including red, green, and blue.

7. The method of claim 5, further comprising applying the second local micro-contrast convergence algorithm to the first multi-dimensional color space to produce a second multi-dimensional color space that is separate and distinct from the first multi-dimensional color space.

8. The method of claim 7, further comprising:
   converting the second multi-dimensional color space to a single dimensional grayscale image.

9. The method of claim 8, wherein the second multi-dimensional color space includes a luminance dimension having luminance values corresponding to each pixel of the second multi-dimensional color space.

10. The method of claim 9, wherein converting the second multi-dimensional color space to a single dimensional grayscale image includes altering the luminance values corresponding to each pixel in the second multi-dimensional color space to convert to the grayscale image.

11. The method of claim 1, wherein the first image is an image generated by x-ray, ultrasound, infrared, ultraviolet, magnetic resonance imaging (MRI), computed tomography (CT) scan, positron emission tomography (PET) scan, grayscale, color, visible light, mm wave, or laser scan.

12. The method of claim 1, wherein the feature is a breast cancer, a prostate cancer, a kidney cancer, a liver cancer, a bone cancer, a lung cancer, a brain cancer, or a skin cancer.

13. The method of claim 1, wherein the feature is a biomarker for cardiovascular disease, Alzheimer's disease, eye disease, or multiple sclerosis lesion.

14. The method of claim 1, wherein the feature is a chemical marker for a solid or liquid organic compound.

15. The method of claim 1, wherein the feature is a structural defect.

16. The method of claim 12, wherein the feature is the breast cancer, and a false positive rate for the breast cancer is less than 10%.

17. The method of claim 12, wherein the feature is the breast cancer, and a false positive rate for the breast cancer is less than 5%.

18. The method of claim 12, wherein the feature is the breast cancer, and a false positive rate for the breast cancer is less than 1%.

19. The method of claim 1, further comprising displaying the second image, including displaying distinctive color patterns in the second image that define boundaries of abnormal tissue and reveal structures of normal tissue.

20. The method of claim 1, further comprising displaying the second image, including displaying characteristic pattern responses generated from the applying of the first local micro-contrast convergence algorithm to the first image, wherein the characteristic pattern responses including an edge, a boundary, an internal structure, a texture, a spiculation, a luminance value, or a color associated with a cancer response.

21. The method of claim 1, wherein the visualization of the self-similar patterns is a quantifiable visualization.

* * * * *